US010329578B2

(12) United States Patent
Bermudez et al.

(10) Patent No.: US 10,329,578 B2
(45) Date of Patent: Jun. 25, 2019

(54) GLYPHOSATE-N-ACETYLTRANSFERASE (GLYAT) SEQUENCES AND METHODS OF USE

(71) Applicant: PIONEER HI-BRED INTERNATIONAL, INC., Johnston, IA (US)

(72) Inventors: Ericka Bermudez, Aptos, CA (US); Linda A. Castle, Mountain View, CA (US); Kevin E. McBride, Davis, CA (US); Daniel Siehl, Menlo Park, CA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 68 days.

(21) Appl. No.: 15/029,783

(22) PCT Filed: Oct. 14, 2014

(86) PCT No.: PCT/US2014/060331
§ 371 (c)(1),
(2) Date: Apr. 15, 2016

(87) PCT Pub. No.: WO2015/057600
PCT Pub. Date: Apr. 23, 2015

(65) Prior Publication Data
US 2016/0257971 A1   Sep. 8, 2016

Related U.S. Application Data

(60) Provisional application No. 61/892,663, filed on Oct. 18, 2013.

(51) Int. Cl.
*C12N 15/82* (2006.01)
*C12N 9/10* (2006.01)
(52) U.S. Cl.
CPC ....... *C12N 15/8275* (2013.01); *C12N 9/1029* (2013.01); *C12N 9/1077* (2013.01); *C12Y 204/02* (2013.01)
(58) Field of Classification Search
None
See application file for complete search history.

(56) References Cited

U.S. PATENT DOCUMENTS 7,405,074 B2 *   7/2008   Castle ............... C12N 15/8275
                                              435/193
7,999,152 B2 *   8/2011   Castle ................. C12N 9/1029
                                              435/193
2008/0044904 A1   2/2008   Pal Malaiga

FOREIGN PATENT DOCUMENTS

| WO | 2002/36782 A2 | 5/2002 |
| WO | 2003/092360 A2 | 11/2003 |
| WO | 2005/012515 A2 | 2/2005 |
| WO | 2007/024782 A2 | 3/2007 |
| WO | 2007/024866 A2 | 3/2007 |
| WO | 2008/002872 A2 | 1/2008 |
| WO | 2008/112019 A2 | 9/2008 |
| WO | 2011/005823 A1 | 1/2011 |
| WO | 2012/071039 A1 | 5/2012 |
| WO | 2012/071040 A1 | 5/2012 |

OTHER PUBLICATIONS

Castle et al, Science (2004) 304:1151-1154.*
Linda A. Castle et al., Discovery and Directed Evolution of a Glyphosate Tolerance Gene, Science, May 21, 2004, pp. 1151-1154, vol. 304(5674).
International Search Report and Written Opinion—PCT/US2014/060331—dated Mar. 31, 2015.

* cited by examiner

Primary Examiner — Mykola V. Kovalenko

(57) ABSTRACT

Compositions and methods comprising polynucleotides and polypeptides having glyphosate-N-acetyltransferase (GLYAT) activity are provided. In specific embodiments, the sequence has an improved property, such as, but not limited to, an improved specificity for glyphosate when compared to an appropriate control resulting in decreased off target acetylation of, e.g. an amino acid such as aspartate. Further provided are nucleic acid constructs, plants, plant cells, explants, seeds and grain having the GLYAT sequences. Various methods of employing the GLYAT sequences are provided. Such methods include methods for producing a glyphosate tolerant plant, plant cell, explant or seed and methods of controlling weeds in a field containing a crop employing the plants and/or seeds disclosed herein.

23 Claims, 2 Drawing Sheets
Specification includes a Sequence Listing.

GLYPHOSATE-N-ACETYLTRANSFERASE (GLYAT) SEQUENCES AND METHODS OF USE

CROSS REFERENCE TO RELATED APPLICATION

This application claims the benefit of U.S. Provisional Application No. 61/892,663, filed Oct. 18, 2013, which is incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named 20141008_BB2152PCT_SeqListing.txt created on Oct. 8, 2014 and having a size of 223 kilobytes and is filed concurrently with the specification. The sequence listing contained in this ASCII formatted document is part of the specification and is herein incorporated by reference in its entirety.

FIELD

The field relates to the field of molecular biology. More specifically, it pertains to sequences that confer tolerance to glyphosate.

BACKGROUND

In the commercial production of crops, it is desirable to easily and quickly eliminate unwanted plants (i.e., "weeds") from a field of crop plants. A herbicide treatment could be applied to an entire field that would eliminate only the unwanted plants while leaving the crop plants unharmed. One such treatment system would involve the use of crop plants which are tolerant to an herbicide so that when the herbicide was sprayed on a field of herbicide-tolerant crop plants, the crop plants would continue to thrive while non-herbicide-tolerant weeds were killed or severely damaged.

Crop tolerance to specific herbicides can be conferred by engineering genes into crops which encode appropriate herbicide metabolizing enzymes and/or insensitive herbicide targets. In some cases these enzymes, and the nucleic acids that encode them, originate in a plant. In other cases, they are derived from other organisms, such as microbes. Indeed, transgenic plants have been engineered to express a variety of herbicide tolerance genes from a variety of organisms.

While a number of herbicide-tolerant crop plants are presently commercially available, improvements in every aspect of crop production, weed control options, extension of residual weed control, and improvement in crop yield are continuously in demand. Particularly, due to local and regional variation in dominant weed species as well as preferred crop species, a continuing need exists for customized systems of crop protection and weed management which can be adapted to the needs of a particular region, geography, and/or locality. A continuing need therefore exists for compositions and methods of crop protection and weed management.

SUMMARY

Compositions and methods comprising polynucleotides and polypeptides having glyphosate-N-acetyltransferase (GLYAT) activity are provided. In specific embodiments, the sequence has an improved property, such as, but not limited to, an improved specificity for glyphosate when compared to an appropriate control resulting in decreased non-specific acetylation. Further provided are nucleic acid constructs, plants, plant cells, explants, seeds and grain having the GLYAT sequences.

Various methods of employing the GLYAT sequences are provided. Such methods include methods for producing a glyphosate tolerant organisms, plant, plant cell, explant or seed and methods of controlling weeds in a field containing a crop employing the plants and/or seeds.

DETAILED DESCRIPTION

The present disclosure makes reference to the accompanying drawings, in which some, but not all embodiments and modifications thereof are shown. Indeed, the embodiments may exist in many different forms and should not be construed as limited to those set forth herein; rather, the embodiments are provided such that this disclosure will satisfy applicable legal requirements. Like numbers refer to like elements throughout.

Other embodiments and modifications thereof will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

I. Compositions

A. Glyphosate-N-acetyltransferase (GLYAT) Polynucleotides and Polypeptides

Figure 1:
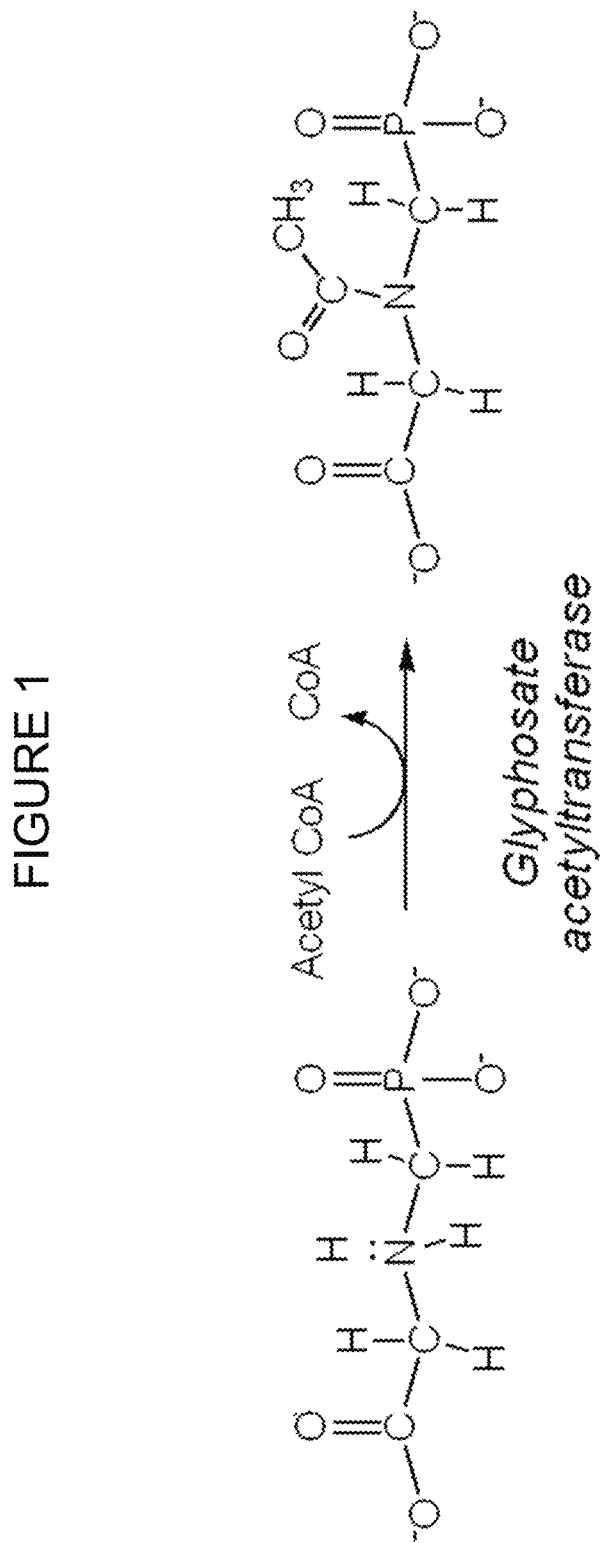
FIG. 1 depicts the N-acetylation of glyphosate catalyzed by a glyphosate-N-acetyltransferase ("GLYAT").

As used herein, a "glyphosate-N-acetyltransferase" or "GLYAT" polypeptide or enzyme comprises a polypeptide which has glyphosate-N-acetyltransferase activity ("GLYAT" activity), i.e., the ability to catalyze the acetylation of the secondary amine of glyphosate, as depicted in FIG. 1. In specific embodiments, a polypeptide having glyphosate-N-acetyltransferase activity can transfer the acetyl group from acetyl CoA to the secondary amine of glyphosate. In addition, one or more GLYAT polypeptides transfer the propionyl group of propionyl CoA to the secondary amine of glyphosate. One or more GLYAT polypeptides are also capable of catalyzing the acetylation of glyphosate analogs and/or glyphosate metabolites, e.g., aminomethylphosphonic acid. In addition, one or more GLYATs are also able to transfer the propionyl group of propionyl CoA to glyphosate, indicating that GLYAT is also an acyl transferase. As discussed in further detail elsewhere herein, the use of fragments and variants of GLYAT polynucleotides and polypeptides encoded thereby is also encompassed by the present disclosure.

Various methods and compositions are provided which employ polynucleotides and polypeptides having GLYAT activity. Such GLYAT polypeptides include those set forth in any one of SEQ ID NO: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, and/or 172 and biologically active variants and fragments thereof. Further provided are the polynucleotides encoding these various polypeptides and active variants and fragments thereof.

Further provided are a novel class of GLYAT polypeptides and polynucleotides encoding the same. Specifically, GLYAT polypeptides, and polynucleotides encoding the same, are provided which comprise at least one motif as set forth in SEQ ID NO:174. In further embodiments, the GLYAT polypeptides, and polynucleotides encoding the same, which comprise the motif set forth in SEQ ID NO:174, further comprises or encodes a sequence having at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to any GLYAT sequence including any one of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, and/or 172, and/or 173 or any GLYAT sequence found in U.S. Pat. Nos. 7,863,503 and 7,666,643, both of which are herein incorporated by reference.

Further provided are GLYAT polypeptides, and polynucleotides encoding the same, wherein the polypeptide has GLYAT activity and, wherein a) the amino acid residue in the encoded polypeptide that corresponds to amino acid position 3 of SEQ ID NO:2 comprises a serine or a cysteine; b) the amino acid residue in the encoded polypeptide that corresponds to amino acid position 6 of SEQ ID NO:2 comprises methionine; c) the amino acid residue in the encoded polypeptide that corresponds to amino acid position 8 of SEQ ID NO:2 comprises glycine; d) the amino acid residue in the encoded polypeptide that corresponds to amino acid position 23 of SEQ ID NO:2 comprises glycine, arginine, or lysine; e) the amino acid residue in the encoded polypeptide that corresponds to amino acid position 25 of SEQ ID NO:2 comprises serine; f) the amino acid residue in the encoded polypeptide that corresponds to amino acid position 26 of SEQ ID NO:2 comprises phenylalanine; g) the amino acid residue in the encoded polypeptide that corresponds to amino acid position 27 of SEQ ID NO:2 comprises serine or arginine; h) the amino acid residue in the encoded polypeptide that corresponds to amino acid position 28 of SEQ ID NO:2 comprises arginine or lysine; i) the amino acid residue in the encoded polypeptide that corresponds to amino acid position 29 of SEQ ID NO:2 comprises isoleucine; j) the amino acid residue in the encoded polypeptide that corresponds to amino acid position 31 of SEQ ID NO:2 comprises tryptophan; k) the amino acid residue in the encoded polypeptide that corresponds to amino acid position 39 of SEQ ID NO:2 comprises cysteine; l) the amino acid residue in the encoded polypeptide that corresponds to amino acid position 41 of SEQ ID NO:2 comprises serine; m) the amino acid residue in the encoded polypeptide that corresponds to amino acid position 42 of SEQ ID NO:2 comprises histidine; n) the amino acid residue in the encoded polypeptide that corresponds to amino acid position 46 of SEQ ID NO:2 comprises cysteine; o) the amino acid residue in the encoded polypeptide that corresponds to amino acid position 48 of SEQ ID NO:2 comprises alanine; p) the amino acid residue in the encoded polypeptide that corresponds to amino acid position 58 of SEQ ID NO:2 comprises glycine; q) the amino acid residue in the encoded polypeptide that corresponds to amino acid position 59 of SEQ ID NO:2 comprises cysteine; r) the amino acid residue in the encoded polypeptide that corresponds to amino acid position 60 of SEQ ID NO:2 comprises leucine; s) the amino acid residue in the encoded polypeptide that corresponds to amino acid position 63 of SEQ ID NO:2 comprises serine or arginine; t) the amino acid residue in the encoded polypeptide that corresponds to amino acid position 67 of SEQ ID NO:2 comprises cysteine; u) the amino acid residue in the encoded polypeptide that corresponds to amino acid position 68 of SEQ ID NO:2 comprises valine; v) the amino acid residue in the encoded polypeptide that corresponds to amino acid position 75 of SEQ ID NO:2 comprises alanine; w) the amino acid residue in the encoded polypeptide that corresponds to amino acid position 79 of SEQ ID NO:2 comprises glycine; x) the amino acid residue in the encoded polypeptide that corresponds to amino acid position 83 of SEQ ID NO:2 comprises asparagine; y) the amino acid residue in the encoded polypeptide that corresponds to amino acid position 85 of SEQ ID NO:2 comprises arginine; z) the amino acid residue in the encoded polypeptide that corresponds to amino acid position 87 of SEQ ID NO:2 comprises alanine; aa) the amino acid residue in the encoded polypeptide that corresponds to amino acid position 88 of SEQ ID NO:2 comprises arginine; bb) the amino acid residue in the encoded polypeptide that corresponds to amino acid position 89 of SEQ ID NO:2 comprises arginine or asparagine; cc) the amino acid residue in the encoded polypeptide that corresponds to amino acid position 90 of SEQ ID NO:2 comprises valine; dd) the amino acid residue in the encoded polypeptide that corresponds to amino acid position 91 of SEQ ID NO:2 comprises methionine; ee) the amino acid residue in the encoded polypeptide that corresponds to amino acid position 95 of SEQ ID NO:2 comprises glutamine; ff) the amino acid residue in the encoded polypeptide that corresponds to amino acid position 96 of SEQ ID NO:2 comprises aspartic acid; gg) the amino acid residue in the encoded polypeptide that corresponds to amino acid position 98 of SEQ ID NO:2 comprises methionine; hh) the amino acid residue in the encoded polypeptide that corresponds to amino acid position 99 of SEQ ID NO:2 comprises valine, alanine, or lysine; ii) the amino acid residue in the encoded polypeptide that corresponds to amino acid position 100 of SEQ ID NO:2 comprises alanine; jj) the amino acid residue in the encoded polypeptide that corresponds to amino acid position 101 of SEQ ID NO:2 comprises alanine, cysteine, leucine, or isoleucine; kk) the amino acid residue in the encoded polypeptide that corresponds to amino acid position 105 of SEQ ID NO:2 comprises threonine; ll) the amino acid residue in the encoded polypeptide that corresponds to amino acid position 109 of SEQ ID NO:2 comprises phenylalanine or glutamine; mm) the amino acid residue in the encoded polypeptide that corresponds to amino acid position 112 of SEQ ID NO:2 comprises valine, leucine, or methionine; nn) the amino acid residue in the encoded polypeptide that corresponds to amino acid position 125 of SEQ ID NO:2 comprises serine; oo) the amino acid residue in the encoded polypeptide that corresponds to amino acid position 128 of SEQ ID NO:2 comprises glycine, threonine, alanine, arginine, or cysteine; pp) the amino acid residue in the encoded polypeptide that corresponds to amino acid position 130 of SEQ ID NO:2 comprises tryptophan; qq) the amino acid residue in the encoded polypeptide that corresponds to amino acid position 131 of SEQ ID NO:2 comprises glutamine or arginine; rr) the amino acid residue in the encoded polypeptide that corresponds to amino acid position 132 of SEQ ID NO:2 comprises tyrosine; ss) the amino acid residue in the encoded polypeptide that corresponds to amino acid position 133 of SEQ ID NO:2 comprises lysine; tt) the amino acid residue in the encoded polypeptide that corresponds to amino acid position 137 of SEQ ID NO:2 comprises glutamic acid, alanine, arginine, or serine; and/or uu) the amino acid residue in the encoded polypeptide that corresponds to amino acid position 142 of SEQ ID NO:2 comprises valine or cysteine. In still further embodiments, the GLYAT polypeptide described above further comprises at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% to any one of SEQ ID NOS: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, and/or 173.

The GLYAT polypeptides and active variants and fragments thereof disclosed herein may have improved enzymatic activity when compared to previously identified GLYAT polypeptides. The GLYAT polypeptides disclosed herein can have a lower capacity for acetylation of an amino acid, such as aspartate, when compared to previously known GLYAT enzymes, while still retaining the ability to acetylate glyphosate. For example, the GLYAT polypeptides or active variants thereof can have a decrease in $k_{cat}/K_M$ for aspartate. By "decrease" is intended any statistically significant reduction in measured activity when compared to an appropriate control. In some embodiments, an appropriate control is a previously known GLYAT sequence, such as that set forth in SEQ ID NO:2. In some embodiments, the decrease in the $k_{cat}/K_M$ for aspartate when compared to SEQ ID NO:2 can comprise about a 1, 3, 5, 6, 7, 8, 9, 10, 11, 12, 12.5, 13, 14, 15, 16, 17, 18, 19, 20, 25, 30, 35, 40, 45, 50 fold or greater reduction in the $k_{cat}/K_M$ for aspartate. In still further embodiments, a decrease in the $k_{cat}/K_M$ for aspartate can include, for example, a $k_{cat}/K_M$ for aspartate of less than about 5.0, 1.0, 1.0, 0.5, 0.1, 0.05, 0.01 min$^{-1}$mM$^{-1}$, or less.

In still further embodiments, the GLYAT polypeptides having a lower capacity for acetylation of aspartate also have an improved specificity for acetylating glyphosate. By "improved specificity for glyphosate" is intended the $k_{cat}/K_M$ for aspartate divided by the $k_{cat}/K_M$ for glyphosate, expressed as a percent, is decreased when compared to an appropriate control. In some embodiments, an appropriate control is a previously known GLYAT sequence, such as that set forth in SEQ ID NO:2. In some embodiments, the improved specificity for glyphosate when compared to SEQ ID NO:2 comprises about a 1, 5, 10, 20, 30, 40, 50, 100 or more fold reduction in $[(k_{cat}/K_M)_{asp}/(k_{cat}/K_M)_{gly}]\times100$. A decrease in the $[(k_{cat}/KM)_{asp}/(k_{cat}/K_M)_{gly}]\times100$ can include, for example, a value of less than about 0.01%.

While the various GLYAT sequences and active variants and fragments thereof disclosed herein can have any one or more of the characteristics discussed above, each of the GLYAT sequences disclosed herein and active variants or fragments thereof also have "glyphosate-N-acetyltransferase activity" or "GLYAT" activity. Enzymatic activity can be characterized using the conventional kinetic parameters $k_{cat}$, $K_M$, and $k_{cat}/K_M$. $k_{cat}$ is the number of moles of substrate transformed per minute per mole of enzyme under optimal conditions, which includes saturating substrate concentration; $K_M$ is a measure of the affinity of the GLYAT enzyme for its substrates (e.g., acetyl CoA, propionyl CoA and glyphosate); and $k_{cat}/K_M$ is a measure of catalytic efficiency that takes both substrate affinity and catalytic rate into account. $k_{cat}/K_M$ is relevant in the situation where the concentration of a substrate is at least partially rate-limiting. In general, a GLYAT with a higher $k_{cat}$ or $k_{cat}/K_M$ is a more efficient catalyst than another GLYAT with a lower $k_{cat}$ or $k_{cat}/K_M$. A GLYAT with a lower $K_M$ (for glyphosate) is a more efficient catalyst than another GLYAT with a higher $K_M$. Thus, to determine whether one GLYAT is more effective than another, one can compare kinetic parameters for the two enzymes. The relevance of $k_{cat}$, $k_{cat}/K_M$ and $K_M$ will vary depending upon the context in which the GLYAT will be expected to function, e.g., the anticipated effective concentration of glyphosate relative to the $K_M$ for glyphosate. GLYAT activity can also be characterized in terms of any of a number of functional characteristics, including but not limited to stability, susceptibility to inhibition, or activation by other molecules.

Thus, for example, the GLYAT polypeptide may have a lower $K_M$ for glyphosate, for example, less than 1 mM, 0.9 mM, 0.8 mM, 0.7 mM, 0.6 mM, 0.5 mM, 0.4 mM, 0.3 mM, 0.2 mM, 0.1 mM, 0.05 mM, or less. The GLYAT polypeptide may have a higher $k_{cat}$ for glyphosate than previously identified enzymes, for example, a $k_{cat}$ of at least 500 $min^{-1}$, 1000 $min^{-1}$, 1100 $min^{-1}$, 1200 $min^{-1}$, 1250 $min^{-1}$, 1300 $min^{-1}$, 1400 $min^{-1}$, 1500 $min^{-1}$, 1600 $min^{-1}$, 1700 $min^{-1}$, 1800 $min^{-1}$, 1900 $min^{-1}$, or 2000 $min^{-1}$ or higher. GLYAT polypeptides as described in this disclosure may have a higher $k_{cat}/K_M$ for glyphosate than previously identified enzymes, for example, a $k_{cat}/K_M$ of at least 1000 $mM^{-1}min^{-1}$, 2000 $mM^{-1}min^{-1}$, 3000 $mM^{-1}min^{-1}$, 4000 $mM^{-1}min^{-1}$, 5000 $mM^{-1}min^{-1}$, 6000 $mM^{-1}min^{-1}$, 7000 $mM^{-1}min^{-1}$, or 8000 $mM^{-1}min^{-1}$, or higher. The activity of GLYAT enzymes is affected by, for example, pH and salt concentration; and appropriate assay methods and conditions are known in the art (see, e.g., WO2005012515). Such improved enzymes may find particular use in methods of growing a crop in a field where the crop exhibits increased crop tolerance against a particular herbicide or combination of herbicides and/or other agricultural chemicals.

As used herein, an "isolated" or "purified" polynucleotide or polypeptide, or biologically active portion thereof, is substantially free from components that normally accompany or interact with the polynucleotide or polypeptide as found in its naturally occurring environment. Thus, an isolated or purified polynucleotide or polypeptide is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For purposes of this disclosure, "isolated" or "recombinant" when used to refer to nucleic acid molecules excludes isolated unmodified chromosomes. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein. When the polypeptide of the disclosure or a biologically active portion thereof is recombinantly produced, optimally culture medium represents less than about 30%, 20%, 10%, 5%, or 1% (by dry weight) of chemical precursors or non-protein-of-interest chemicals.

As used herein, a "recombinant" polynucleotide comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or active variant or fragment thereof such that an additional chemically linked nucleic acid segment is located either 5', 3' or internal to the polynucleotide of interest. Alternatively, the chemically-linked nucleic acid segment of the recombinant polynucleotide can be formed by the deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides are disclosed herein, including, for example, by chemical synthesis or by the manipulation of isolated segments of polynucleotides by genetic engineering techniques. In specific embodiments, the recombinant polynucleotide can comprise a recombinant DNA sequence or a recombinant RNA sequence.

A "recombinant polynucleotide construct" comprises two or more operably linked nucleic acid segments which are not found operably linked in nature. Non-limiting examples of recombinant polynucleotide constructs include a polynucleotide of interest or active variant or fragment thereof operably linked to heterologous sequences which aid in the expression, autologous replication, and/or genomic insertion of the sequence of interest. Such heterologous and operably linked sequences include, for example, promoters, termination sequences, enhancers, etc, or any component of an expression cassette; a plasmid, cosmid, virus, autonomously replicating sequence, phage, or linear or circular single-stranded or double-stranded DNA or RNA nucleotide sequence; and/or sequences that encode heterologous polypeptides.

A "recombinant polypeptide" comprises a combination of two or more chemically linked amino acid segments which are not found directly joined in nature. In specific embodiments, the recombinant polypeptide comprises an additional chemically linked amino acid segment that is located either at the N-terminal, C-terminal or internal to the recombinant polypeptide. Alternatively, the chemically-linked amino acid segment of the recombinant polypeptide can be formed by deletion of at least one amino acid. The additional chemically linked amino acid segment or the deleted chemically linked amino acid segment can be of any length, including for example, 1, 2, 3, 4, 5, 6, 7, 8, 9, 10, 15, 20 or amino acids.

B. Active Fragments and Variants of GLYAT Sequences

Methods and compositions are provided which employ polynucleotides and polypeptides having glyphosate-N-acetyltransferase activity. Moreover, any given variant or fragment of a GLYAT sequence may further comprise an improved specificity for glyphosate when compared to an appropriate control resulting in decreased non-specific acetylation of, e.g. an amino acid such as aspartate.

i. Polynucleotide and Polypeptide Fragments

Fragments and variants of GLYAT polynucleotides and polypeptides are also encompassed by the present disclosure. By "fragment" is intended a portion of the polynucleotide or a portion of the amino acid sequence and hence protein encoded thereby. Fragments of a polynucleotide may encode protein fragments that retain GLYAT activity, and in specific embodiments, can further comprise an improved specificity for glyphosate when compared to an appropriate control resulting in decreased non-specific acetylation of, e.g. an amino acid such as aspartate. Alternatively, fragments of a polynucleotide that are useful as hybridization probes or PCR primers generally do not encode fragment proteins retaining biological activity. In specific embodiments, a fragment of a recombinant polynucleotide or a recombinant polynucleotide construct comprises at least one junction of the two or more chemically linked or operably linked nucleic acid segments which are not found directly joined in nature. Thus, fragments of a nucleotide sequence may range from at least about 20 nucleotides, about 50 nucleotides, about 100 nucleotides, and up to the full-length polynucleotide encoding the GLYAT polypeptides. A fragment of a GLYAT polynucleotide that encodes a biologically active portion of a GLYAT protein of the disclosure will encode at least 25, 50, 75, 100, 125, 147 contiguous amino acids, or up to the total number of amino acids present in a full-length GLYAT polypeptide.

Thus, a fragment of a GLYAT polynucleotide may encode a biologically active portion of a GLYAT polypeptide, or it may be a fragment that can be used as a hybridization probe or PCR primer using methods disclosed below. A biologically active portion of a GLYAT polypeptide can be prepared by isolating a portion of one of the GLYAT polynucleotides, expressing the encoded portion of the GLYAT polypeptides (e.g., by recombinant expression in vitro), and assessing the activity of the GLYAT portion of the GLYAT protein. Polynucleotides that are fragments of a GLYAT nucleotide sequence comprise at least 16, 20, 50, 75, 100, 150, 200, 250, 300, 350, 400, 450 contiguous nucleotides, or up to the number of nucleotides present in a full-length GLYAT polynucleotide disclosed herein.

Fragments of a polypeptide may encode protein fragments that retain GLYAT activity, and in specific embodiments, can further comprise an improved specificity for glyphosate when compared to an appropriate control resulting in decreased non-specific acetylation of, e.g. an amino acid such as aspartate. A fragment of a GLYAT polypeptide disclosed herein will encode at least 25, 50, 75, 100, 125, 147 contiguous amino acids, or up to the total number of amino acids present in a full-length GLYAT polypeptide. In specific embodiments, such polypeptide fragments are active fragments, and in still other embodiments, the polypeptide fragment comprises a recombinant polypeptide fragment. As used herein, a fragment of a recombinant polypeptide comprises at least one of a combination of two or more chemically linked amino acid segments which are not found directly joined in nature.

ii. Polynucleotide and Polypeptide Variants

"Variant" protein is intended to mean a protein derived from the protein by deletion (i.e., truncation at the 5' and/or 3' end) and/or a deletion or addition of one or more amino acids at one or more internal sites in the native protein and/or substitution of one or more amino acids at one or more sites in the native protein. Variant proteins encompassed are biologically active, that is they continue to possess the desired biological activity, that is, have GLYAT activity. Moreover, any given variant or fragment may further comprise an improved specificity for glyphosate when compared to an appropriate control resulting in decreased non-specific acetylation of, e.g. an amino acid such as aspartate. Such variants may result from, for example, genetic polymorphism or from human manipulation.

"Variants" is intended to mean substantially similar sequences. For polynucleotides, a variant comprises a polynucleotide having a deletion (i.e., truncations) at the 5' and/or 3' end and/or a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the GLYAT polypeptides of the disclosure. Naturally occurring variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis or gene synthesis but which still encode a GLYAT polypeptide.

Biologically active variants of a GLYAT polypeptide (and the polynucleotide encoding the same) will have at least about 85%, 90%, 91%, 92%, 93%, 93.5%, 94%, 94.5%, 95%, 95.5%, 96%, 96.5%, 97%, 97.5%, 98%, 98.5%, 99%, 99.5%, or more sequence identity to the polypeptide of any one of SEQ ID NO: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, and/or 172 as determined by sequence alignment programs and parameters described elsewhere herein.

In specific embodiments, the biologically active variants of a GLYAT polypeptide (and polynucleotide encoding the same) will have at least 94.5% sequence identity to the full length of SEQ ID NO:3; at least 96.6% sequence identity to the full length of SEQ ID NO:4; at least 93.8% sequence identity to the full length of SEQ ID NO:5; at least 92.4% sequence identity to the full length of SEQ ID NO:6; at least 91.8% sequence identity to the full length of SEQ ID NO:7; at least 93.1% sequence identity to the full length of SEQ ID NO:8; at least 93.8% sequence identity to the full length of SEQ ID NO:9; at least 93.8% sequence identity to the full length of SEQ ID NO:10; at least 93.1% sequence identity to the full length of SEQ ID NO:11; at least 92.5% sequence identity to the full length of SEQ ID NO:12; at least 93.2% sequence identity to the full length of SEQ ID NO:13; at least 93.2% sequence identity to the full length of SEQ ID NO:14; at least 95.9% sequence identity to the full length of SEQ ID NO:15; at least 92.5% sequence identity to the full length of SEQ ID NO:16; at least 90.4% sequence identity to the full length of SEQ ID NO:17; at least 93.2% sequence identity to the full length of SEQ ID NO:18; at least 93.8% sequence identity to the full length of SEQ ID NO:19; at least 92.5% sequence identity to the full length of SEQ ID NO:20; at least 95.9% sequence identity to the full length of SEQ ID NO:21; at least 91.7% sequence identity to the full length of SEQ ID NO:22; at least 92.5% sequence identity to the full length of SEQ ID NO:23; at least 90.4% sequence identity to the full length of SEQ ID NO:24; at least 89.7% sequence identity to the full length of SEQ ID NO:25; at least 92.4% sequence identity to the full length of SEQ ID NO:26; at least 91.7% sequence identity to the full length of SEQ ID NO:27; at least 87.6% sequence identity to the full length of SEQ ID NO:28; at least 88.3% sequence identity to the full length of SEQ ID NO:29; at least 89% sequence identity to the full length of SEQ ID NO:30; at least 87.6% sequence identity to the full length of SEQ ID NO:31; at least 91.7% sequence identity to the full length of SEQ ID NO:32; at least 89.7% sequence identity to the full length of SEQ ID NO:33; at least 89% sequence identity to the full length of SEQ ID NO:34; at least 86.9% sequence identity to the full length of SEQ ID NO:35; at least 89% sequence identity to the full length of SEQ ID NO:36; at least 89.7% sequence identity to the full length of SEQ ID NO:37; at least 87.6% sequence identity to the full length of SEQ ID NO:38; at least 89.7% sequence identity to the full length of SEQ ID NO:39; at least 89.7% sequence identity to the full length of SEQ ID NO:40; at least 89.7% sequence identity to the full length of SEQ ID NO:41; at least 89.7% sequence identity to the full length of SEQ ID NO:42; at least 89.7% sequence identity to the full length of SEQ ID NO:43; at least 88.3% sequence identity to the full length of SEQ ID NO:44; at least 88.3% sequence identity to the full length of SEQ ID NO:45; at least 89.7% sequence identity to the full length of SEQ ID NO:46; at least 89% sequence identity to the full length of SEQ ID NO:47; at least 88.3% sequence identity to the full length of SEQ ID NO:48; at least 88.3% sequence identity to the full length of SEQ ID NO:49; at least 89.7% sequence identity to the full length of SEQ ID NO:50; at least 89.7% sequence identity to the full length of SEQ ID NO:51; at least 88.3% sequence identity to the full length of SEQ ID NO:52; at least 89% sequence identity to the full length of SEQ ID NO:53; at least 87.6% sequence identity to the full length of SEQ ID NO:54; at least 91.7% sequence identity to the full length of SEQ ID NO:55; at least 87.6% sequence identity to the full length of SEQ ID NO:56; at least 91% sequence identity to the full length of SEQ ID NO:57; at least 89% sequence identity to the full length of SEQ ID NO:58; at least 90.3% sequence identity to the full length of SEQ ID NO:59; at least 89% sequence identity to the full length of SEQ ID NO:60; at least 87.6% sequence identity to the full length of SEQ ID NO:61; at least 89.7% sequence identity to the full length of SEQ ID NO:62; at least 89% sequence identity to the full length of SEQ ID NO:63; at least 89% sequence identity to the full length of SEQ ID NO:64; at least 90.3% sequence identity to the full length of SEQ ID NO:65; at least 89.7% sequence identity to the full length of SEQ ID NO:66; at least 89% sequence identity to the full length of SEQ ID NO:67; at least 88.3% sequence identity to the full length of SEQ ID NO:68; at least 90.3% sequence identity to the full length of SEQ ID NO:69; at least 89% sequence identity to the full length of SEQ ID NO:70; at least 89% sequence identity to the full length of SEQ ID NO:71; at least 88.3% sequence identity to the full length of SEQ ID NO:72; at least 89% sequence identity to the full length of SEQ ID NO:73; at least 89.7% sequence identity to the full length of SEQ ID NO:74; at least 88.3% sequence identity to the full length of SEQ ID NO:75; at least 88.3% sequence identity to the full length of SEQ ID NO:76; at least 89% sequence identity to the full length of SEQ ID NO:77; at least 91% sequence identity to the full length of SEQ ID NO:78; at least 90.3% sequence identity to the full length of SEQ ID NO:79; at least 90.3% sequence identity to the full length of SEQ ID NO:80; at least 89% sequence identity to the full length of SEQ ID NO:81; at least 89% sequence identity to the full length of SEQ ID NO:82; at least 89.7% sequence identity to the full length of SEQ ID NO:83; at least 89.7% sequence identity to the full length of SEQ ID NO:84; at least 89% sequence identity to the full length of SEQ ID NO:85; at least 89.7% sequence identity to the full length of SEQ ID NO:86; at least 88.3% sequence identity to the full length of SEQ ID NO:87; at least 90.3% sequence identity to the full length of SEQ ID NO:88; at least 90.3% sequence identity to the full length of SEQ ID NO:89; at least 89% sequence identity to the full length of SEQ ID NO:90; at least 87.6% sequence identity to the full length of SEQ ID NO:91; at least 89% sequence identity to the full length of SEQ ID NO:92; at least 89.7% sequence identity to the full length of SEQ ID NO:93; at least 90.3% sequence identity to the full length of SEQ ID NO:94; at least 89.7% sequence identity to the full length of SEQ ID NO:95; at least 89% sequence identity to the full length of SEQ ID NO:96; at least 89% sequence identity to the full length of SEQ ID NO:97; at least 89% sequence identity to the full length of SEQ ID NO:98; at least 91% sequence identity to the full length of SEQ ID NO:99; at least 88.3% sequence identity to the full length of SEQ ID NO:100; at least 89% sequence identity to the full length of SEQ ID NO:101; at least 91.7% sequence identity to the full length of SEQ ID NO: 102; at least 91.7% sequence identity to the full length of SEQ ID NO: 103; at least 93% sequence identity to the full length of SEQ ID NO: 104; at least 91.7% sequence identity to the full length of SEQ ID NO: 105; at least 91.7% sequence identity to the full length of SEQ ID NO: 106; at least 91.7% sequence identity to the full length of SEQ ID NO:107; at least 91.7% sequence identity to the full length of SEQ ID NO: 108; at least 91.7% sequence identity to the full length of SEQ ID NO:109; at least 91.7% sequence identity to the full length of SEQ ID NO:110; at least 91.7% sequence identity to the full length of SEQ ID NO:111; at least 91.7% sequence identity to the full length of SEQ ID NO:112; at least 91.7% sequence identity to the full length of SEQ ID NO:113; at least 91.7% sequence identity to the full length of SEQ ID NO:114; at least 91.7% sequence identity to the full length of SEQ ID NO:115; at least 92.4% sequence identity to the full length of SEQ ID NO:116; at least 92.4% sequence identity to the full length of SEQ ID NO:117; at least 93.1% sequence identity to the full length of SEQ ID NO:118; at least 91.7% sequence identity to the full length of SEQ ID NO:119; at least 91.7% sequence identity to the full length of SEQ ID NO:120; at least 91.7% sequence identity to the full length of SEQ ID NO:121; at least 91.7% sequence identity to the full length of SEQ ID NO:122; at least 91.7% sequence identity to the full length of SEQ ID NO:123; at least 91.7% sequence identity to the full length of SEQ ID NO:124; at least 91.7% sequence identity to the full length of SEQ ID NO:125; at least 91.7% sequence identity to the full length of SEQ ID NO:126; at least 91.7% sequence identity to the full length of SEQ ID NO:127; at least 91.7% sequence identity to the full length of SEQ ID NO:128; at least 92.4% sequence identity to the full length of SEQ ID NO:129; at least 91.7% sequence identity to the full length of SEQ ID NO:130; at least 91.7% sequence identity to the full length of SEQ ID NO:131; at least 91.7% sequence identity to the full length of SEQ ID NO: 132; at least 91.7% sequence identity to the full length of SEQ ID NO:133; at least 91.7% sequence identity to the full length of SEQ ID NO: 134; at least 91.7% sequence identity to the full length of SEQ ID NO:135; at least 91.7% sequence identity to the full length of SEQ ID NO: 136; at least 91.7% sequence identity to the full length of SEQ ID NO: 137; at least 91.7% sequence identity to the full length of SEQ ID NO: 138; at least 92.4% sequence identity to the full length of SEQ ID NO:139; at least 91.7% sequence identity to the full length of SEQ ID NO:140; at least 91.7% sequence identity to the full length of SEQ ID NO:141; at least 91.7% sequence identity to the full length of SEQ ID NO:142; at least 91.7% sequence identity to the full length of SEQ ID NO:143; at least 91.7% sequence identity to the full length of SEQ ID NO:144; at least 91.7% sequence identity to the full length of SEQ ID NO:145; at least 91.7% sequence identity to the full length of SEQ ID NO:146; at least 91.7% sequence identity to the full length of SEQ ID NO:147; at least 91.7% sequence identity to the full length of SEQ ID NO:148; at least 91.7% sequence identity to the full length of SEQ ID NO:149; at least 92.4% sequence identity to the full length of SEQ ID NO: 150; at least 91.7% sequence identity to the full length of SEQ ID NO:151; at least 91.7% sequence identity to the full length of SEQ ID NO:152; at least 91.7% sequence identity to the full length of SEQ ID NO: 153; at least 91.7% sequence identity to the full length of SEQ ID NO:154; at least 91.7% sequence identity to the full length of SEQ ID NO:155; at least 91% sequence identity to the full length of SEQ ID NO:156; at least 91.7% sequence identity to the full length of SEQ ID NO: 157; at least 91.7% sequence identity to the full length of SEQ ID NO: 158; at least 91.7% sequence identity to the full length of SEQ ID NO: 159; at least 91.7% sequence identity to the full length of SEQ ID NO:160; at least 91.7% sequence identity to the full length of SEQ ID NO:161; at least 91.7% sequence identity to the full length of SEQ ID NO:162; at least 92.4% sequence identity to the full length of SEQ ID NO:163; at least 92.4% sequence identity to the full length of SEQ ID NO:164; at least 91.7% sequence identity to the full length of SEQ ID NO:165; at least 91.7% sequence identity to the full length of SEQ ID NO:166; at least 91.7% sequence identity to the full length of SEQ ID NO:167; at least 91.7% sequence identity to the full length of SEQ ID NO:168; at least 91.7% sequence identity to the full length of SEQ ID NO:169; at least 91.7% sequence identity to the full length of SEQ ID NO:170; at least 91.7% sequence identity to the full length of SEQ ID NO:171; and/or at least 91.7% sequence identity to the full length of SEQ ID NO:172; wherein percent identity is determined using the BLAST alignment used the BLOSUM62 substitution matrix, a gap existence penalty of 11, and a gap extension penalty of 1.

In other embodiments, variants of a GLYAT polypeptide (and the polynucleotides encoding the same) will have a similarity score of at least 650, 660, 670, 680, 690, 700, 710, 720, 725, 730, 731, 735, 740, 745, 750, 755, 760, 761, 762, 765, 770, 775, 780, 785, 790, 795, 800, 805, 810, 815, 820, 825, 830, 835, 840, 845, 850, 855, 860, 865, 870, 875, 880, 885, 890, 895, 900, 920, 950, 975, 1000, or greater as determined by parameters described elsewhere herein to a polynucleotide encoding any one of SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, and/or 172. In specific embodiments, the biologically active GLYAT variant (and polynucleotide encoding the same) comprises a polypeptide having glyphosate-N-acetyltransferase (GLYAT) activity and further comprising an amino acid sequence having: a similarity score of at least 760 with SEQ ID NO:3; a similarity score of at least 762 with SEQ ID NO:4; a similarity score of at least 744 with SEQ ID NO:5; a similarity score of at least 738 with SEQ ID NO:6; a similarity score of at least 728 with SEQ ID NO:7; a similarity score of at least 746 with SEQ ID NO:8; a similarity score of at least 747 with SEQ ID NO:9; a similarity score of at least 740 with SEQ ID NO:10; a similarity score of at least 747 with SEQ ID NO:11; a similarity score of at least 746 with SEQ ID NO:12; a similarity score of at least 746 with SEQ ID NO:13; a similarity score of at least 740 with SEQ ID NO:14; a similarity score of at least 756 with SEQ ID NO:15; a similarity score of at least 736 with SEQ ID NO:16; a similarity score of at least 721 with SEQ ID NO:17; a similarity score of at least 744 with SEQ ID NO:18; a similarity score of at least 744 with SEQ ID NO:19; a similarity score of at least 737 with SEQ ID NO:20; a similarity score of at least 753 with SEQ ID NO:21; a similarity score of at least 727 with SEQ ID NO:22; a similarity score of at least 742 with SEQ ID NO:23; a similarity score of at least 718 with SEQ ID NO:24; a similarity score of at least 703 with SEQ ID NO:25; a similarity score of at least 738 with SEQ ID NO:26; a similarity score of at least 731 with SEQ ID NO:27; a similarity score of at least 708 with SEQ ID NO:28; a similarity score of at least 707 with SEQ ID NO:29; a similarity score of at least 707 with SEQ ID NO:30; a similarity score of at least 700 with SEQ ID NO:31; a similarity score of at least 726 with SEQ ID NO:32; a similarity score of at least 714 with SEQ ID NO:33; a similarity score of at least 703 with SEQ ID NO:34; a similarity score of at least 694 with SEQ ID NO:35; a similarity score of at least 720 with SEQ ID NO:36; a similarity score of at least 721 with SEQ ID NO:37; a similarity score of at least 694 with SEQ ID NO:38; a similarity score of at least 714 with SEQ ID NO:39; a similarity score of at least 722 with SEQ ID NO:40; a similarity score of at least 718 with SEQ ID NO:41; a similarity score of at least 721 with SEQ ID NO:42; a similarity score of at least 717 with SEQ ID NO:43; a similarity score of at least 707 with SEQ ID NO:44; a similarity score of at least 709 with SEQ ID NO:45; a similarity score of at least 717 with SEQ ID NO:46; a similarity score of at least 714 with SEQ ID NO:47; a similarity score of at least 704 with SEQ ID NO:48; a similarity score of at least 709 with SEQ ID NO:49; a similarity score of at least 717 with SEQ ID NO:50; a similarity score of at least 719 with SEQ ID NO:51; a similarity score of at least 707 with SEQ ID NO:52; a similarity score of at least 712 with SEQ ID NO:53; a similarity score of at least 704 with SEQ ID NO:54; a similarity score of at least 733 with SEQ ID NO:55; a similarity score of at least 694 with SEQ ID NO:56; a similarity score of at least 722 with SEQ ID NO:57; a similarity score of at least 707 with SEQ ID NO:58; a similarity score of at least 718 with SEQ ID NO:59; a similarity score of at least 708 with SEQ ID NO:60; a similarity score of at least 700 with SEQ ID NO:61; a similarity score of at least 714 with SEQ ID NO:62; a similarity score of at least 708 with SEQ ID NO:63; a similarity score of at least 714 with SEQ ID NO:64; a similarity score of at least 724 with SEQ ID NO:65; a similarity score of at least 713 with SEQ ID NO:66; a similarity score of at least 710 with SEQ ID NO:67; a similarity score of at least 710 with SEQ ID NO:68; a similarity score of at least 720 with SEQ ID NO:69; a similarity score of at least 709 with SEQ ID NO:70; a similarity score of at least 714 with SEQ ID NO:71; a similarity score of at least 703 with SEQ ID NO:72; a similarity score of at least 709 with SEQ ID NO:73; a similarity score of at least 720 with SEQ ID NO:74; a similarity score of at least 708 with SEQ ID NO:75; a similarity score of at least 700 with SEQ ID NO:76; a similarity score of at least 715 with SEQ ID NO:77; a similarity score of at least 722 with SEQ ID NO:78; a similarity score of at least 724 with SEQ ID NO:79; a similarity score of at least 723 with SEQ ID NO:80; a similarity score of at least 709 with SEQ ID NO:81; a similarity score of at least 709 with SEQ ID NO:82; a similarity score of at least 716 with SEQ ID NO:83; a similarity score of at least 721 with SEQ ID NO:84; a similarity score of at least 711 with SEQ ID NO:85; a similarity score of at least 717 with SEQ ID NO:86; a similarity score of at least 705 with SEQ ID NO:87; a similarity score of at least 720 with SEQ ID NO:88; a similarity score of at least 728 with SEQ ID NO:89; a similarity score of at least 717 with SEQ ID NO:90; a similarity score of at least 703 with SEQ ID NO:91; a similarity score of at least 710 with SEQ ID NO:92; a similarity score of at least 716 with SEQ ID NO:93; a similarity score of at least 723 with SEQ ID NO:94; a similarity score of at least 715 with SEQ ID NO:95; a similarity score of at least 716 with SEQ ID NO:96; a similarity score of at least 709 with SEQ ID NO:97; a similarity score of at least 718 with SEQ ID NO:98; a similarity score of at least 726 with SEQ ID NO:99; a similarity score of at least 705 with SEQ ID NO:100; a similarity score of at least 709 with SEQ ID NO:101; a similarity score of at least 736 with SEQ ID NO:102; a similarity score of at least 734 with SEQ ID NO:103; a similarity score of at least 729 with SEQ ID NO:104; a
similarity score of at least 736 with SEQ ID NO:105; a
similarity score of at least 730 with SEQ ID NO:106; a
similarity score of at least 730 with SEQ ID NO:107; a
similarity score of at least 733 with SEQ ID NO:108; a
similarity score of at least 732 with SEQ ID NO:109; a
similarity score of at least 730 with SEQ ID NO:110; a
similarity score of at least 732 with SEQ ID NO:111; a
similarity score of at least 731 with SEQ ID NO:112; a
similarity score of at least 733 with SEQ ID NO:113; a
similarity score of at least 734 with SEQ ID NO:114; a
similarity score of at least 733 with SEQ ID NO:115; a
similarity score of at least 731 with SEQ ID NO:116; a
similarity score of at least 733 with SEQ ID NO:117; a
similarity score of at least 732 with SEQ ID NO:118; a
similarity score of at least 735 with SEQ ID NO:119; a
similarity score of at least 732 with SEQ ID NO:120; a
similarity score of at least 732 with SEQ ID NO:121; a
similarity score of at least 731 with SEQ ID NO:122; a
similarity score of at least 729 with SEQ ID NO:123; a
similarity score of at least 732 with SEQ ID NO:124; a
similarity score of at least 730 with SEQ ID NO:125; a
similarity score of at least 732 with SEQ ID NO:126; a
similarity score of at least 734 with SEQ ID NO:127; a
similarity score of at least 733 with SEQ ID NO:128; a
similarity score of at least 732 with SEQ ID NO:129; a
similarity score of at least 732 with SEQ ID NO:130; a
similarity score of at least 735 with SEQ ID NO:131; a
similarity score of at least 734 with SEQ ID NO:132; a
similarity score of at least 732 with SEQ ID NO:133; a
similarity score of at least 735 with SEQ ID NO:134; a
similarity score of at least 736 with SEQ ID NO:135; a
similarity score of at least 732 with SEQ ID NO:136; a
similarity score of at least 733 with SEQ ID NO:137; a
similarity score of at least 736 with SEQ ID NO:138; a
similarity score of at least 736 with SEQ ID NO:139; a
similarity score of at least 736 with SEQ ID NO:140; a
similarity score of at least 736 with SEQ ID NO:141; a
similarity score of at least 731 with SEQ ID NO:142; a
similarity score of at least 735 with SEQ ID NO:143; a
similarity score of at least 733 with SEQ ID NO:144; a
similarity score of at least 734 with SEQ ID NO:145; a
similarity score of at least 733 with SEQ ID NO:146; a
similarity score of at least 730 with SEQ ID NO:147; a
similarity score of at least 728 with SEQ ID NO:148; a
similarity score of at least 734 with SEQ ID NO:149; a
similarity score of at least 735 with SEQ ID NO:150; a
similarity score of at least 733 with SEQ ID NO:151; a
similarity score of at least 731 with SEQ ID NO:152; a
similarity score of at least 734 with SEQ ID NO:153; a
similarity score of at least 732 with SEQ ID NO:154; a
similarity score of at least 734 with SEQ ID NO:155; a
similarity score of at least 726 with SEQ ID NO:156; a
similarity score of at least 733 with SEQ ID NO:157; a
similarity score of at least 730 with SEQ ID NO:158; a
similarity score of at least 733 with SEQ ID NO:159; a
similarity score of at least 733 with SEQ ID NO:160; a
similarity score of at least 728 with SEQ ID NO:161; a
similarity score of at least 733 with SEQ ID NO:162; a
similarity score of at least 735 with SEQ ID NO:163; a
similarity score of at least 733 with SEQ ID NO:164; a
similarity score of at least 734 with SEQ ID NO:165; a
similarity score of at least 731 with SEQ ID NO:166; a
similarity score of at least 732 with SEQ ID NO:167; a
similarity score of at least 732 with SEQ ID NO:168; a
similarity score of at least 729 with SEQ ID NO:169; a
similarity score of at least 736 with SEQ ID NO:170; a
similarity score of at least 732 with SEQ ID NO:171; and/or a similarity score of at least 729 with SEQ ID NO:172; wherein said similarity score is generated using the BLAST alignment program, with the BLOSUM62 substitution matrix, a gap existence penalty of 11, and a gap extension penalty of 1.

In still further embodiments, a biologically active variant of a GLYAT protein may differ from that protein by 75, 70, 65, 60, 55, 50, 45, 40, 35, 30, 25, 20, 19, 18, 17, 16 amino acid residues, as few as 1-15 amino acid residues, as few as 1-10, such as 6-10, as few as 10, 9, 8, 7, 6, 5, as few as 4, 3, 2, or even 1 amino acid residue.

The GLYAT polypeptide and the active variants and fragments thereof may be altered in various ways including amino acid substitutions, deletions, truncations, and insertions. Methods for such manipulations are generally known in the art. For example, amino acid sequence variants and fragments of the GLYAT proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

The mutations that will be made in the DNA encoding the variant must not place the sequence out of reading frame and optimally will not create complementary regions that could produce secondary mRNA structure. See, EP Patent Application Publication No. 75,444.

In general, methods to modify or alter the host genomic DNA are available. For example, a pre-existing GLYAT sequence in a host plant can be modified or altered in a site-specific fashion using one or more site-specific engineering system. This includes altering the host DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein, is generated using "custom" or engineered endonucleases such as meganucleases produced to modify plant genomes (see e.g., WO 2009/114321; Gao et al. (2010) *Plant Journal* 1:176-187). Another site-directed engineering is through the use of zinc finger domain recognition coupled with the restriction properties of restriction enzyme. See e.g., Urnov, et al., (2010) *Nat Rev Genet.* 11(9):636-46; Shukla, et al., (2009) *Nature* 459 (7245):437-41. A transcription activator-like (TAL) effector-DNA modifying enzyme (TALE or TALEN) is also used to engineer changes in plant genome. See e.g., US20110145940, Cermak et al., (2011) *Nucleic Acids Res.* 39(12) and Boch et al., (2009), *Science* 326(5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), *Plant Methods* 9: 39; The CRISPR/Cas system allows targeted cleavage of genomic DNA guided by a customizable small noncoding RNA. Based on the disclosure of the FC coding sequences, polypeptide sequences of the orthologs/homologs and the genomic DNA sequences, site-directed mutagenesis can be readily performed to generate plants expressing a higher level of the endogenous FC polypeptide or an ortholog thereof.

Variant polynucleotides and proteins also encompass sequences and proteins derived from a mutagenic and recombinogenic procedure such as DNA shuffling. With such a procedure, one or more different GLYAT coding sequences can be manipulated to create a new GLYAT possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the GLYAT sequences disclosed herein and other known GLYAT genes to obtain a new gene coding for a protein with an improved property of interest, such as an improvement in GLYAT activity and/or an improved specificity for glyphosate when compared to an appropriate control resulting in decreased non-specific acetylation of, e.g. an amino acid such as aspartate.

D. Sequence Comparisons

The following terms are used to describe the sequence relationships between two or more polynucleotides or polypeptides: "reference sequence", "comparison window", "sequence identity", and, "percent sequence identity."

As used herein, "reference sequence" is a predetermined sequence used as a basis for sequence comparison. A reference sequence may be a subset or the entirety of a specified sequence; for example, as a segment of a full-length cDNA or gene sequence, or the complete cDNA or gene sequence or protein sequence.

As used herein, "comparison window" makes reference to a contiguous and specified segment of a polypeptide sequence, wherein the polypeptide sequence in the comparison window may comprise additions or deletions (i.e., gaps) compared to the reference sequence (which does not comprise additions or deletions) for optimal alignment of the two polypeptides. Generally, the comparison window is at least 5, 10, 15, or 20 contiguous amino acids in length, or it can be 30, 40, 50, 100, or longer. Those of skill in the art understand that to avoid a high similarity to a reference sequence due to inclusion of gaps in the polypeptide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the disclosure. BLAST protein searches can be performed with the BLASTX program, score=50, wordlength=3, to obtain amino acid sequences homologous to a protein or polypeptide of the disclosure. BLASTP protein searches can be performed using default parameters. See, blast.ncbi.nlm.nih.gov/Blast.cgi.

To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTP for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity). When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percent sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percent sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percent sequence identity.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acids substitution matrices and their use in quantifying the similarity between two sequences are well-known in the art and described, e.g., in Dayhoff et al. (1978) "A model of evolutionary change in proteins." In "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) *Proc. Natl. Acad. Sci. USA* 89:10915-10919. The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score.

While optimal alignment and scoring can be accomplished manually, the process is facilitated by the use of a computer-implemented alignment algorithm, e.g., gapped BLAST 2.0, described in Altschul et al, (1997) Nucleic Acids Res. 25:3389-3402, and made available to the public at the National Center for Biotechnology Information Website. Optimal alignments, including multiple alignments, can be prepared using, e.g., PSI-BLAST described by Altschul et al, (1997) Nucleic Acids Res. 25:3389-3402.

As used herein, similarity score and bit score is determined employing the BLAST alignment used the BLOSUM62 substitution matrix, a gap existence penalty of 11, and a gap extension penalty of 1. For the same pair of sequences, if there is a numerical difference between the scores obtained when using one or the other sequence as query sequences, a greater value of similarity score is selected.

E. Plants and Other Host Cells of Interest

Further provided are engineered host cells that are transduced (transformed or transfected) with one or more GLYAT sequences or active variants or fragments thereof. The GLYAT polypeptides or variants and fragments thereof can be expressed in any organism, including in non-animal cells such as plants, yeast, fungi, bacteria and the like. Details regarding non-animal cell culture can be found in Payne et al. (1992) *Plant Cell and Tissue Culture in Liquid Systems*, John Wiley & Sons, Inc. New York, N.Y.; Gamborg and Phillips (eds.) (1995) *Plant Cell, Tissue and Organ Culture*; Fundamental Methods Springer Lab Manual, Springer-Verlag (Berlin, Heidelberg, New York); and Atlas and Parks (eds.) *The Handbook of Microbiological Media* (1993) CRC Press, Boca Raton, Fla.

Plants, plant cells, plant parts and seeds, and grain having the GLYAT sequences disclosed herein are also provided. In specific embodiments, the plants and/or plant parts have stably incorporated at least one heterologous GLYAT polypeptide disclosed herein or an active variant or fragment thereof. Thus, plants, plant cells, plant parts and seeds are provided which comprise at least one heterologous GLYAT sequences of any one or more of SEQ ID NOS: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, or a biologically active fragment and/or variant thereof.

In other embodiments, plants, plant cells, plant parts and seeds are provided which comprise at least one heterologous GLYAT polypeptides (or polynucleotides encoding the same) which comprise at least one motif as set forth in SEQ ID NO:174. In further embodiments, the plants, plant cells, plant parts and seeds comprise a nucleotide sequence which encodes the motif set forth in SEQ ID NO:174 and further encodes a sequence having at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to any GLYAT sequence including any one of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, and/or 173 or any GLYAT sequence found in U.S. Pat. Nos. 7,863,503 and 7,666,643, both of which are herein incorporated by reference.

Further provided are plants, plant cells, plant parts and seeds comprising at least one heterologous GLYAT polypeptide (or polynucleotide encoding the same), wherein the polypeptide has GLYAT activity and, wherein a) the amino acid residue in the encoded polypeptide that corresponds to amino acid position 3 of SEQ ID NO:2 comprises a serine or a cysteine; b) the amino acid residue in the encoded polypeptide that corresponds to amino acid position 6 of SEQ ID NO:2 comprises methionine; c) the amino acid residue in the encoded polypeptide that corresponds to amino acid position 8 of SEQ ID NO:2 comprises glycine; d) the amino acid residue in the encoded polypeptide that corresponds to amino acid position 23 of SEQ ID NO:2 comprises glycine, arginine, or lysine; e) the amino acid residue in the encoded polypeptide that corresponds to amino acid position 25 of SEQ ID NO:2 comprises serine; f) the amino acid residue in the encoded polypeptide that corresponds to amino acid position 26 of SEQ ID NO:2 comprises phenylalanine; g) the amino acid residue in the encoded polypeptide that corresponds to amino acid position 27 of SEQ ID NO:2 comprises serine or arginine; h) the amino acid residue in the encoded polypeptide that corresponds to amino acid position 28 of SEQ ID NO:2 comprises arginine or lysine; i) the amino acid residue in the encoded polypeptide that corresponds to amino acid position 29 of SEQ ID NO:2 comprises isoleucine; j) the amino acid residue in the encoded polypeptide that corresponds to amino acid position 31 of SEQ ID NO:2 comprises tryptophan; k) the amino acid residue in the encoded polypeptide that corresponds to amino acid position 39 of SEQ ID NO:2 comprises cysteine; l) the amino acid residue in the encoded polypeptide that corresponds to amino acid position 41 of SEQ ID NO:2 comprises serine; m) the amino acid residue in the encoded polypeptide that corresponds to amino acid position 42 of SEQ ID NO:2 comprises histidine; n) the amino acid residue in the encoded polypeptide that corresponds to amino acid position 46 of SEQ ID NO:2 comprises cysteine; o) the amino acid residue in the encoded polypeptide that corresponds to amino acid position 48 of SEQ ID NO:2 comprises alanine; p) the amino acid residue in the encoded polypeptide that corresponds to amino acid position 58 of SEQ ID NO:2 comprises glycine; q) the amino acid residue in the encoded polypeptide that corresponds to amino acid position 59 of SEQ ID NO:2 comprises cysteine; r) the amino acid residue in the encoded polypeptide that corresponds to amino acid position 60 of SEQ ID NO:2 comprises leucine; s) the amino acid residue in the encoded polypeptide that corresponds to amino acid position 63 of SEQ ID NO:2 comprises serine or arginine; t) the amino acid residue in the encoded polypeptide that corresponds to amino acid position 67 of SEQ ID NO:2 comprises cysteine; u) the amino acid residue in the encoded polypeptide that corresponds to amino acid position 68 of SEQ ID NO:2 comprises valine; v) the amino acid residue in the encoded polypeptide that corresponds to amino acid position 75 of SEQ ID NO:2 comprises alanine; w) the amino acid residue in the encoded polypeptide that corresponds to amino acid position 79 of SEQ ID NO:2 comprises glycine; x) the amino acid residue in the encoded polypeptide that corresponds to amino acid position 83 of SEQ ID NO:2 comprises asparagine; y) the amino acid residue in the encoded polypeptide that corresponds to amino acid position 85 of SEQ ID NO:2 comprises arginine; z) the amino acid residue in the encoded polypeptide that corresponds to amino acid position 87 of SEQ ID NO:2 comprises alanine; aa) the amino acid residue in the encoded polypeptide that corresponds to amino acid position 88 of SEQ ID NO:2 comprises arginine; bb) the amino acid residue in the encoded polypeptide that corresponds to amino acid position 89 of SEQ ID NO:2 comprises arginine or asparagine; cc) the amino acid residue in the encoded polypeptide that corresponds to amino acid position 90 of SEQ ID NO:2 comprises valine; dd) the amino acid residue in the encoded polypeptide that corresponds to amino acid position 91 of SEQ ID NO:2 comprises methionine; ee) the amino acid residue in the encoded polypeptide that corresponds to amino acid position 95 of SEQ ID NO:2 comprises glutamine; ff) the amino acid residue in the encoded polypeptide that corresponds to amino acid position 96 of SEQ ID NO:2 comprises aspartic acid; gg) the amino acid residue in the encoded polypeptide that corresponds to amino acid position 98 of SEQ ID NO:2 comprises methionine; hh) the amino acid residue in the encoded polypeptide that corresponds to amino acid position 99 of SEQ ID NO:2 comprises valine, alanine, or lysine; ii) the amino acid residue in the encoded polypeptide that corresponds to amino acid position 100 of SEQ ID NO:2 comprises alanine; jj) the amino acid residue in the encoded polypeptide that corresponds to amino acid position 101 of SEQ ID NO:2 comprises alanine, cysteine, leucine, or isoleucine; kk) the amino acid residue in the encoded polypeptide that corresponds to amino acid position 105 of SEQ ID NO:2 comprises threonine; ll) the amino acid residue in the encoded polypeptide that corresponds to amino acid position 109 of SEQ ID NO:2 comprises phenylalanine or glutamine; mm) the amino acid residue in the encoded polypeptide that corresponds to amino acid position 112 of SEQ ID NO:2 comprises valine, leucine, or methionine; nn) the amino acid residue in the encoded polypeptide that corresponds to amino acid position 125 of SEQ ID NO:2 comprises serine; oo) the amino acid residue in the encoded polypeptide that corresponds to amino acid position 128 of SEQ ID NO:2 comprises glycine, threonine, alanine, arginine, or cysteine; pp) the amino acid residue in the encoded polypeptide that corresponds to amino acid position 130 of SEQ ID NO:2 comprises tryptophan; qq) the amino acid residue in the encoded polypeptide that corresponds to amino acid position 131 of SEQ ID NO:2 comprises glutamine or arginine; rr) the amino acid residue in the encoded polypeptide that corresponds to amino acid position 132 of SEQ ID NO:2 comprises tyrosine; ss) the amino acid residue in the encoded polypeptide that corresponds to amino acid position 133 of SEQ ID NO:2 comprises lysine; tt) the amino acid residue in the encoded polypeptide that corresponds to amino acid position 137 of SEQ ID NO:2 comprises glutamic acid, alanine, arginine, or serine; and/or uu) the amino acid residue in the encoded polypeptide that corresponds to amino acid position 142 of SEQ ID NO:2 comprises valine or cysteine. In still further embodiments, the GLYAT polypeptide described above further comprises at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% to any one of SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, and/or 173.

In specific embodiments, the GLYAT sequence or active variants and fragments thereof have GLYAT activity. In further embodiments, the sequence has GLYAT activity and has an improved specificity for glyphosate when compared to an appropriate control resulting in decreased non-specific acetylation of, e.g. an amino acid such as aspartate.

In addition, the plants or organism of interest can comprise multiple GLYAT polynucleotides (i.e., at least 1, 2, 3, 4, 5, 6 or more). It is recognized that if multiple GLYAT polynucleotides are employed, the GLYAT polynucleotides may encode GLYAT polypeptides having (1) different kinetic parameters, i.e., a GLYAT variant having a lower $K_M$ can be combined with one having a higher $k_{cat}$; (2) different specificity for glyphosate when compared to an appropriate control; and/or (3) different capacity for acetylation of an amino acid, such as aspartate, when compared to an appropriate control.

In specific embodiments, the heterologous polynucleotide in the plant or plant part is operably linked to a constitutive, tissue-preferred, or other promoter for expression in plants.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the disclosure, provided that these parts comprise the introduced polynucleotides.

The GLYAT sequences and active variants and fragments thereof disclosed herein may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, conifers, turf grasses (including cool seasonal grasses and warm seasonal grasses).

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing that which is disclosed include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*), and Poplar and *Eucalyptus*. In specific embodiments, plants of the present disclosure are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

A "subject plant or plant cell" is one in which genetic alteration, such as transformation, has been affected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

In specific embodiments, the glyphosate tolerant plants express a GLYAT polypeptide, i.e., a polypeptide having glyphosate-N-acetyltransferase activity wherein the acetyl group from acetyl CoA is transferred to the secondary amine of glyphosate. Thus, plants of the disclosure that have been treated with glyphosate can contain the metabolite N-acetyl-glyphosate ("NAG"). Methods to detect glyphosate and NAG are described for example in U.S. Pat. No. 8,003,398, which is hereby incorporated by reference.

Additional host cells of interest can be a eukaryotic cell, an animal cell, a protoplast, a tissue culture cell, prokaryotic cell, a bacterial cell, such as *E. coli, B. subtilis, Streptomyces, Salmonella typhimurium*, a gram positive bacteria, a purple bacteria, a green sulfur bacteria, a green non-sulfur bacteria, a cyanobacteria, a spirochetes, a thermatogale, a flavobacteria, bacteroides; a fungal cell, such as *Saccharomyces cerevisiae, Pichia pastoris*, and *Neurospora crassa*; an insect cell such as *Drosophila* and *Spodoptera frugiperda*; a mammalian cell such as CHO, COS, BHK, HEK 293 or Bowes melanoma, archaebacteria (i.e., Korarchaeota, Thermoproteus, Pyrodictium, Thermococcales, Methanogens, Archaeoglobus, and extreme Halophiles) and others.

F. Polynucleotide Constructs

The use of the term "polynucleotide" is not intended to limit a polynucleotide of the disclosure to a polynucleotide comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the disclosure also encompass all forms of sequences including, but not limited to, single-stranded forms, double-stranded forms, hairpins, stem-and-loop structures, and the like.

The GLYAT polynucleotides disclosed herein can be provided in expression cassettes for expression in the plant of interest or any organism of interest. The cassette can include 5' and 3' regulatory sequences operably linked to a GLYAT polynucleotide or active variant or fragment thereof. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the GLYAT polynucleotide or active variant or fragment thereof to be under the transcriptional regulation of the regulatory regions. The expression cassette may additionally contain selectable marker genes.

The expression cassette can include in the 5'-3' direction of transcription, a transcriptional and translational initiation region (i.e., a promoter), a GLYAT polynucleotide or active variant or fragment thereof, and a transcriptional and translational termination region (i.e., termination region) functional in plants. The regulatory regions (i.e., promoters, transcriptional regulatory regions, and translational termination regions) and/or the GLYAT polynucleotide or active variant or fragment thereof may be native/analogous to the host cell or to each other. Alternatively, the regulatory regions and/or the GLYAT polynucleotide of or active variant or fragment thereof may be heterologous to the host cell or to each other.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The termination region may be native with the transcriptional initiation region or active variant or fragment thereof, may be native with the plant host, or may be derived from another source (i.e., foreign or heterologous) to the promoter, the GLYAT polynucleotide or active fragment or variant thereof, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (*Maize* Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385. See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used to express the various GLYAT sequences disclosed herein, including the native promoter of the polynucleotide sequence of interest. The promoters can be selected based on the desired outcome. Such promoters include, for example, constitutive, inducible, tissue-preferred, or other promoters for expression in plants or in any organism of interest.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced GLYAT expression within a particular plant tissue. Tissue-preferred promoters include those described in Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2): 157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Synthetic promoters can be used to express GLYAT sequences or biologically active variants and fragments thereof.

Alternatively, a plant promoter may be under environmental control. Such promoters are referred to here as "inducible" promoters. Examples of environmental conditions that may affect transcription by inducible promoters include pathogen attack, anaerobic conditions, or the presence of light. In particular, examples of inducible promoters are the Adh1 promoter which is inducible by hypoxia or cold stress, the Hsp70 promoter which is inducible by heat stress, and the PPDK promoter which is inducible by light. Also useful are promoters which are chemically inducible.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners; the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters. See, for example, the glucocorticoid-inducible promoter in Schena et al. (1991) *Proc. Natl. Acad. Sci. USA* 88:10421-10425 and McNellis et al. (1998) *Plant J.* 14(2):247-257 and the tetracycline-inducible and tetracycline-repressible promoters for example, Gatz et al. (1991) *Mol. Gen. Genet.* 227:229-237, and U.S. Pat. Nos. 5,814,618 and 5,789,156, herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, sulfonylureas, dicamba, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the context of the present disclosure, including for example, DsRed.

In another aspect, the GLYAT sequences disclosed herein or active variants or fragments thereof can also be used as a selectable marker gene. In this embodiment, the presence of the GLYAT polynucleotide in a cell or organism confers upon the cell or organism the detectable phenotypic trait of glyphosate resistance, thereby allowing one to select for cells or organisms that have been transformed with a gene of interest linked to the GLYAT polynucleotide. Thus, for example, the GLYAT polynucleotide can be introduced into a nucleic acid construct, e.g., a vector, thereby allowing for the identification of a host (e.g., a cell or transgenic plant) containing the nucleic acid construct by growing the host in the presence of glyphosate and selecting for the ability to survive and/or grow at a rate that is discernibly greater than a host lacking the nucleic acid construct would survive or grow. A GLYAT polynucleotide can be used as a selectable marker in a wide variety of hosts that are sensitive to glyphosate, including plants, most bacteria (including *E. coli*), actinomycetes, yeasts, algae and fungi. One benefit of using herbicide resistance as a marker in plants, as opposed to conventional antibiotic resistance, is that it obviates the concern of some members of the public that antibiotic resistance might escape into the environment.

In bacterial systems, a number of expression vectors may be selected depending upon the use intended for the GLYAT polypeptide. For example, when large quantities of GLYAT polypeptide or fragments thereof are needed for commercial production or for induction of antibodies, vectors which direct high level expression of fusion proteins that are readily purified can be desirable. Such vectors include, but are not limited to, multifunctional *E. coli* cloning and expression vectors such as BLUESCRIPT (Stratagene), in which the GLYAT polypeptide coding sequence may be ligated into the vector in-frame with sequences for the amino-terminal Met and the subsequent 7 residues of beta-galactosidase so that a hybrid protein is produced; pIN vectors (Van Heeke & Schuster (1989) *J Biol Chem* 264: 5503-5509); pET vectors (Novagen, Madison Wis.); and the like.

Similarly, in the yeast *Saccharomyces cerevisiae* a number of vectors containing constitutive or inducible promoters such as alpha factor, alcohol oxidase and PGH may be used for production of the GLYAT polypeptides of the disclosure. For reviews, see Ausubel (supra) and Grant et al. (1987) *Methods in Enzymology* 153:516-544.

In mammalian host cells, a variety of expression systems, including viral-based systems, may be utilized. In cases where an adenovirus is used as an expression vector, a coding sequence, e.g., of a GLYAT polypeptide, is optionally ligated into an adenovirus transcription/translation complex consisting of the late promoter and tripartite leader sequence. Insertion of a GLYAT polypeptide coding region into a nonessential E1 or E3 region of the viral genome will result in a viable virus capable of expressing a GLYAT in infected host cells (Logan and Shenk (1984) *Proc Natl Acad Sci USA* 81:3655-3659). In addition, transcription enhancers, such as the rous sarcoma virus (RSV) enhancer, may be used to increase expression in mammalian host cells.

In specific embodiments, the GLYAT polypeptides and active variants and fragments thereof, and polynucleotides encoding the same, further comprise a chloroplast transit peptide. As used herein, the term "chloroplast transit peptide" will be abbreviated "CTP" and refers to the N-terminal portion of a chloroplast precursor protein that directs the latter into chloroplasts and is subsequently cleaved off by the chloroplast processing protease. When a CTP is operably linked to the N-terminus of a polypeptide, the polypeptide is translocated into the chloroplast. Removal of the CTP from a native protein reduces or abolishes the ability of the native protein from being transported into the chloroplast. An operably linked chloroplast transit peptide is found at the N-terminus of the protein to be targeted to the chloroplast and is located upstream and immediately adjacent to the transit peptide cleavage site that separates the transit peptide from the mature protein to be targeted to the chloroplast.

The term "chloroplast transit peptide cleavage site" refers to a site between two amino acids in a chloroplast-targeting sequence at which the chloroplast processing protease acts. Chloroplast transit peptides target the desired protein to the chloroplast and can facilitate the proteins translocation into the organelle. This is accompanied by the cleavage of the transit peptide from the mature polypeptide or protein at the appropriate transit peptide cleavage site by a chloroplast processing protease, native to the chloroplast. Accordingly, a chloroplast transit peptide further comprises a suitable cleavage site for the correct processing of the pre-protein to the mature polypeptide contained within the chloroplast.

As used herein, a "heterologous" CTP comprises a transit peptide sequence which is foreign to the polypeptide it is operably linked to. Such heterologous chloroplast transit peptides are known, including but not limited to those derived from *Pisum* (JP 1986224990; E00977), carrot (Luo et al. (1997) *Plant Mol. Biol.*, 33 (4), 709-722 (Z33383), *Nicotiana* (Bowler et al., EP 0359617; A09029), *Oryza* (de Pater et al. (1990) *Plant Mol. Biol.*, 15 (3), 399-406 (X51911), as well as synthetic sequences such as those provided in EP 0189707; U.S. Pat. No. 5,728,925; U.S. Pat. No. 5,717,084 (A10396 and A10398). In one embodiment, the heterologous chloroplast transit peptide is from the ribulose-1,5-bisphosphate carboxylase (Rubisco) small subunit precursor protein isolated from any plant. The Rubisco small subunit is well characterized from a variety of plants and the transit peptide from any of them will be suitable for use disclosed herein. See for example, *Physcomitrella* (Quatrano et al., AW599738); *Lotus* (Poulsen et al., AW428760); *Citrullus* (J. S. Shin, A1563240); *Nicotiana* (Appleby et al. (1997) *Heredity* 79(6), 557-563); alfalfa (Khoudi et al. (1997) *Gene*, 197(1/2), 343-351); potato and tomato (Fritz et al. (1993) *Gene*, 137(2), 271-4); wheat (Galili et al. (1991) *Theor. Appl. Genet.* 81(1), 98-104); and rice (Xie et al. (1987) *Sci. Sin.*, Ser. B (Engl. Ed.), 30(7), 706-19). For example, transit peptides may be derived from the Rubisco small subunit isolated from plants including but not limited to, soybean, rapeseed, sunflower, cotton, corn, tobacco, alfalfa, wheat, barley, oats, *sorghum*, rice, *Arabidopsis*, sugar beet, sugar cane, canola, millet, beans, peas, rye, flax, and forage grasses. Preferred for use in the present disclosure is the Rubisco small subunit precursor protein from, for example, *Arabidopsis* or tobacco.

G. Stacking Other Traits of Interest

In some embodiments, the GLYAT polynucleotides or active variants and fragments thereof disclosed herein are engineered into a molecular stack. Thus, the various host cells, plants, plant cells and seeds disclosed herein can further comprise one or more traits of interest, and in more specific embodiments, the host cell, plant, plant part or plant cell is stacked with any combination of polynucleotide sequences of interest in order to create plants with a desired combination of traits. As used herein, the term "stacked" includes having the multiple traits present in the same plant or organism of interest. In one non-limiting example, "stacked traits" comprise a molecular stack where the sequences are physically adjacent to each other. A trait, as used herein, refers to the phenotype derived from a particular sequence or groups of sequences. In one embodiment, the molecular stack comprises at least one additional polynucleotide that also confers tolerance to at least one sequence that confers tolerance to glyphosate by the same and/or different mechanism and/or at least one additional polynucleotide that confers tolerance to a second herbicide.

Thus, in one embodiment, the host cells, plants, plant cells or plant part having the GLYAT polynucleotide or active variants or fragments thereof disclosed herein is stacked with at least one other GLYAT sequence. Such GLYAT sequence include the GLYAT sequence and variants and fragment thereof disclosed herein, as well as other GLYAT sequence, which include but are not limited to, the GLYAT sequences set forth in WO02/36782, US Publication 2004/0082770 and WO 2005/012515, U.S. Pat. Nos. 7,462,481, 7,405,074, each of which is herein incorporated by reference.

In some embodiments, the host cells, plants or plant cells having the GLYAT polynucleotides or active variants or fragments thereof may be stacked with other herbicide-tolerance traits to create a transgenic plant of the disclosure with further properties. Thus the mechanism of glyphosate resistance conferred by GLYAT can be combined with other modes of glyphosate resistance known in the art. Glyphosate-tolerance traits which confer tolerance to glyphosate via a different mechanism than GLYAT include a sequence that encodes a glyphosate oxido-reductase enzyme as described more fully in U.S. Pat. Nos. 5,776,760 and 5,463,175, each of which is incorporated by reference. Other traits include polynucleotides that confer on the plant the capacity to produce a higher level or glyphosate insensitive 5-enolpyruvylshikimate-3-phosphate synthase (EPSPS), for example, as more fully described in U.S. Pat. Nos. 6,248,876 B1; 5,627,061; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and U.S. Pat. No. 5,491,288; and international publications WO 97/04103; WO 00/66746; WO 01/66704; WO 00/66747, WO2007064828, WO2006110586, WO2007146765, WO2008002964, US App. Pubs. 2009/0307802, 201/0197499, 2009/0209427, and U.S. Pat. Nos. 8,436,159 and 6,040,497.

The mechanism of glyphosate resistance produced by the GLYAT sequences disclosed herein may be combined with other modes of herbicide resistance to provide host cells, plants, plant explants and plant cells that are resistant to glyphosate and one or more other herbicides. For example, the plant or plant cell or plant part having the GLYAT sequence or an active variant or fragment thereof is stacked with, for example, a sequence which confers tolerance to an ALS inhibitor. As used herein, an "ALS inhibitor-tolerant polypeptide" comprises any polypeptide which when expressed in a plant confers tolerance to at least one ALS inhibitor. A variety of ALS inhibitors are known and include, for example, sulfonylurea, imidazolinone, triazolopyrimidines, pryimidinyloxy(thio)benzoates, and/or sulfonylaminocarbonyltriazolinone herbicides. Additional ALS inhibitors are known and are disclosed elsewhere herein. It is known in the art that ALS mutations fall into different classes with regard to tolerance to sulfonylureas, imidazolinones, triazolopyrimidines, and pyrimidinyl(thio)benzoates, including mutations having the following characteristics: (1) broad tolerance to all four of these groups; (2) tolerance to imidazolinones and pyrimidinyl(thio)benzoates; (3) tolerance to sulfonylureas and triazolopyrimidines; and (4) tolerance to sulfonylureas and imidazolinones.

Various ALS inhibitor-tolerant polypeptides can be employed. In some embodiments, the ALS inhibitor-tolerant polynucleotides contain at least one nucleotide mutation resulting in one amino acid change in the ALS polypeptide. In specific embodiments, the change occurs in one of seven substantially conserved regions of acetolactate synthase. See, for example, Hattori et al. (1995) *Molecular Genetics and Genomes* 246:419-425; Lee et al. (1998) *EMBO Journal* 7:1241-1248; Mazur et al. (1989) *Ann. Rev. Plant Phys.* 40:441-470; and U.S. Pat. No. 5,605,011, each of which is incorporated by reference in their entirety. The ALS inhibitor-tolerant polypeptide can be encoded by, for example, the SuRA or SuRB locus of ALS. In specific embodiments, the ALS inhibitor-tolerant polypeptide comprises the C3 ALS mutant, the HRA ALS mutant, the S4 mutant or the S4/HRA mutant or any combination thereof. Different mutations in ALS are known to confer tolerance to different herbicides and groups (and/or subgroups) of herbicides; see, e.g., Tranel and Wright (2002) *Weed Science* 50:700-712. See also, U.S. Pat. Nos. 5,605,011, 5,378,824, 5,141,870, and 5,013,659, each of which is herein incorporated by reference in their entirety. The soybean, maize, and *Arabidopsis* HRA sequences are disclosed, for example, in WO2007/024782, herein incorporated by reference.

In some embodiments, the ALS inhibitor-tolerant polypeptide confers tolerance to sulfonylurea and/or imidazolinone herbicides. The production of sulfonylurea-tolerant plants and imidazolinone-tolerant plants is described more fully in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference in their entireties for all purposes. In specific embodiments, the ALS inhibitor-tolerant polypeptide comprises a sulfonamide-tolerant acetolactate synthase (otherwise known as a sulfonamide-tolerant acetohydroxy acid synthase) or an imidazolinone-tolerant acetolactate synthase (otherwise known as an imidazolinone-tolerant acetohydroxy acid synthase).

In still other embodiments, plants, plant cells, explants and expression cassettes comprising the GLYAT sequences or active variants and fragments thereof are stacked with a sequence that confers tolerance to an HPPD inhibitor. For example, a P450 sequence could be employed which provides tolerance to HPPD-inhibitors by metabolism of the herbicide. Such sequences including, but are not limited to, the NSF1 gene. See, US 2007/0214515 and US 2008/0052797, both of which are herein incorporated by reference in their entirety. In other embodiments, the plants, plant cells, explants and expression cassettes can comprise a GLYAT sequence or active variant or fragment thereof stacked with an HPPD sequence or variants and fragments thereof which confers tolerance to an HPPD inhibitor. See, for example, US App. Pub. 2012-0042413 and U.S. Pat. Nos. 6,245,968 B1; 6,268,549; and 6,069,115; and international publication WO 99/23886, U.S. Pat. Nos. 6,245,968 B1; and 6,268,549, each of which is herein incorporated by reference.

In still other embodiments, the plant or plant cell or plant part having the GLYAT sequence or an active variants or fragments thereof may be stacked with, for example, aryloxyalkanoate dioxygenase (AAD) polynucleotides (which confer tolerance to 2,4-D and other phenoxy auxin herbicides as well as to aryloxyphenoxypropionate herbicides as described, for example, in WO2005/107437) and dicamba-tolerance polynucleotides as described, for example, in Herman et al. (2005) *J. Biol. Chem.* 280: 24759-24767 and U.S. Pat. No. 8,629,328, auxin polypeptides, acetyl coenzyme A carboxylase (ACCase) polypeptides, and methyl transferases that provide tolerance to auxin herbicides (e.g, US20130109075, Feng et al.).

In other embodiments, plants, plant cells, explants and expression cassettes comprising the GLYAT sequences or active variants and fragments thereof are stacked with a sequence that confers tolerance to an inhibitor of Glutamine synthetase (GS). GS appears to be an essential enzyme necessary for the development and life of most plant cells. Inhibitors of GS are toxic to plant cells. Glufosinate herbicides have been developed based on the toxic effect due to the inhibition of GS in plants. These herbicides are nonselective. They inhibit growth of all the different species of plants present, causing their total destruction. The development of plants containing an exogenous phosphinothricin acetyl transferase is described in U.S. Pat. Nos. 5,969,213; 5,489,520; 5,550,318; 5,874,265; 5,919,675; 5,561,236; 5,648,477; 5,646,024; 6,177,616 B1; and 5,879,903, which are incorporated herein by reference in their entireties for all purposes.

Other examples of herbicide-tolerance traits that could be combined with the plant or plant cell or plant part having the GLYAT sequence or an active variant or fragment thereof include those conferred by polynucleotides encoding an exogenous phosphinothricin acetyltransferase, as described in U.S. Pat. Nos. 5,969,213; 5,489,520; 5,550,318; 5,874,265; 5,919,675; 5,561,236; 5,648,477; 5,646,024; 6,177,616; and 5,879,903. Plants containing an exogenous phosphinothricin acetyltransferase can exhibit improved tolerance to glufosinate herbicides, which inhibit the enzyme glutamine synthase. Other examples of herbicide-tolerance traits that could be combined with the plants or plant cell or plant part having the GLYAT sequence or an active variant or fragment thereof include those conferred by polynucleotides conferring altered protoporphyrinogen oxidase (protox) activity, as described in U.S. Pat. Nos. 6,288,306 B1; 6,282,837 B1; and 5,767,373; and international publication WO 01/12825. Plants containing such polynucleotides can exhibit improved tolerance to any of a variety of herbicides which target the protox enzyme (also referred to as "protox inhibitors").

Other examples of herbicide-tolerance traits that could be combined with the plants or plant cell or plant part having the GLYAT sequence or an active variant or fragment thereof include those conferring tolerance to at least one herbicide in a plant such as, for example, a maize plant or horseweed. Herbicide-tolerant weeds are known in the art, as are plants that vary in their tolerance to particular herbicides. See, e.g., Green and Williams (2004) "Correlation of Corn (*Zea mays*) Inbred Response to Nicosulfuron and Mesotrione," poster presented at the WSSA Annual Meeting in Kansas City, Mo., Feb. 9-12, 2004; Green (1998) *Weed Technology* 12: 474-477; Green and Ulrich (1993) *Weed Science* 41: 508-516. The trait(s) responsible for these tolerances can be combined by breeding or via other methods with the plants or plant cell or plant part having the GLYAT sequence or an active variant or fragment thereof to provide a plant of the disclosure as well as methods of use thereof.

In still further embodiments, the GLYAT sequences can be stacked with at least one polynucleotide encoding a homogentisate solanesyltransferase (HST). See, for example, WO2010023911 herein incorporated by reference in its entirety. In such embodiments, classes of herbicidal compounds—which act wholly or in part by inhibiting HST can be applied over the plants having the HTS polypeptide.

The plant or plant cell or plant part having the GLYAT sequence or an active variant or fragment thereof can also be combined with at least one other trait to produce plants that further comprise a variety of desired trait combinations including, but not limited to, traits desirable for animal feed such as high oil content (e.g., U.S. Pat. No. 6,232,529); balanced amino acid content (e.g., hordothionins (U.S. Pat. Nos. 5,990,389; 5,885,801; 5,885,802; and 5,703,409; U.S. Pat. No. 5,850,016); barley high lysine (Williamson et al. (1987) *Eur. J. Biochem.* 165: 99-106; and WO 98/20122) and high methionine proteins (Pedersen et al. (1986) *J. Biol. Chem.* 261: 6279; Kirihara et al. (1988) *Gene* 71: 359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference. Desired trait combinations also include LLNC (low linolenic acid content; see, e.g., Dyer et al. (2002) *Appl. Microbiol. Biotechnol.* 59: 224-230) and OLCH (high oleic acid content; see, e.g., Fernandez-Moya et al. (2005) *J. Agric. Food Chem.* 53: 5326-5330).

The plant or plant cell or plant part having the GLYAT sequence or an active variant or fragment thereof can also be combined with other desirable traits such as, for example, fumonisim detoxification genes (U.S. Pat. No. 5,792,931), avirulence and disease resistance genes (Jones et al. (1994) *Science* 266: 789; Martin et al. (1993) *Science* 262: 1432; Mindrinos et al. (1994) *Cell* 78: 1089), and traits desirable for processing or process products such as modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine herbicide-tolerant polynucleotides with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

In still further embodiments, the plant, plant cell, explant or seed comprises a GLYAT sequence disclosed herein stacked with a sequence that confers tolerance to glyphosate via a different mechanism that GLYAT and a sequence that confers tolerance to an additional herbicide. In specific embodiments, plants, plant cells, explants or seeds comprise a GLYAT sequence disclosed herein or an active variant or fragment thereof stacked with a sequence encoding a glyphosate tolerant EPSPS and further stacked with an sequence encoding an ALS-inhibitor tolerant sequence. In specific embodiments, the ALS-inhibitor tolerant sequence is HRA.

In other embodiments, the plant or plant cell or plant part having the GLYAT sequence or an active variant or fragment thereof may be stacked with any other polynucleotides encoding polypeptides having pesticidal and/or insecticidal activity, such as *Bacillus thuringiensis* toxic proteins (described in U.S. Pat. Nos. 5,366,892; 5,747,450; 5,737,514; 5,723,756; 5,593,881; Geiser et al. (1986) *Gene* 48: 109; Lee et al. (2003) *Appl. Environ. Microbiol.* 69: 4648-4657

(Vip3A); Galitzky et al. (2001) *Acta Crystallogr. D. Biol. Crystallogr.* 57: 1101-1109 (Cry3Bb1); and Herman et al. (2004) *J. Agric. Food Chem.* 52: 2726-2734 (Cry1F)), lectins (Van Damme et al. (1994) *Plant Mol. Biol.* 24: 825, pentin (described in U.S. Pat. No. 5,981,722), and the like. The combinations generated can also include multiple copies of any one of the polynucleotides of interest.

In another embodiment, the plant or plant cell or plant part having the GLYAT sequence or an active variant or fragment thereof can also be combined with a plant disease resistance gene such as but not limited to the Rcg1 sequence or a biologically active variant or fragment thereof. The Rcg1 sequence is an anthracnose stalk rot resistance gene in corn. See, for example, U.S. patent application Ser. Nos. 11/397,153, 11/397,275, and 11/397,247, each of which is herein incorporated by reference.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Any plant having at GLYAT sequence disclosed herein or an active variant or fragment thereof can be used to make a food or a feed product. Such methods comprise obtaining a plant, explant, seed, plant cell, or cell comprising the GLYAT sequence or active variant or fragment thereof and processing the plant, explant, seed, plant cell, or cell to produce a food or feed product.

H. Method of Introducing

Various methods can be used to introduce a sequence of interest into a host cell, plant or plant part. "Introducing" is intended to mean presenting to the host cell, plant, plant cell or plant part the polynucleotide or polypeptide in such a manner that the sequence gains access to the interior of a cell of the plant or organism. The methods of the disclosure do not depend on a particular method for introducing a sequence into an organism or a plant or plant part, only that the polynucleotide or polypeptides gains access to the interior of at least one cell of the organism or the plant. Methods for introducing polynucleotide or polypeptides into various organisms, including plants, are known in the art including, but not limited to, stable transformation methods, transient transformation methods, and virus-mediated methods.

"Stable transformation" is intended to mean that the nucleotide construct introduced into a plant integrates into the genome of the plant or organism of interest and is capable of being inherited by the progeny thereof. "Transient transformation" is intended to mean that a polynucleotide is introduced into the plant or organism of interest and does not integrate into the genome of the plant or organism or a polypeptide is introduced into a plant or organism.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Nat. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the GLYAT sequences or active variants or fragments thereof can be provided to a plant using a variety of transient transformation methods. Such transient transformation methods include, but are not limited to, the introduction of the GLYAT protein or active variants and fragments thereof directly into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107: 775-784, all of which are herein incorporated by reference.

In other embodiments, the GLYAT polynucleotide disclosed herein or active variants and fragments thereof may be introduced into plants by contacting plants with a virus or viral nucleic acids. Generally, such methods involve incorporating a nucleotide construct of the disclosure within a DNA or RNA molecule. It is recognized that the GLYAT sequence may be initially synthesized as part of a viral polyprotein, which later may be processed by proteolysis in vivo or in vitro to produce the desired recombinant protein.

Further, it is recognized that promoters disclosed herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide disclosed herein can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome. Other methods to target polynucleotides are set forth in WO 2009/114321 (herein incorporated by reference), which describes "custom" meganucleases produced to modify plant genomes, in particular the genome of maize. See, also, Gao et al. (2010) *Plant Journal* 1:176-187.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a polynucleotide disclosed herein, for example, as part of an expression cassette, stably incorporated into their genome.

Transformed plant cells which are derived by plant transformation techniques, including those discussed above, can be cultured to regenerate a whole plant which possesses the transformed genotype (i.e., a GLYAT polynucleotide), and thus the desired phenotype, such as acquired resistance (i.e., tolerance) to glyphosate or a glyphosate analog. For transformation and regeneration of maize see, Gordon-Kamm et al., *The Plant Cell*, 2:603-618 (1990). Plant regeneration from cultured protoplasts is described in Evans et al. (1983) *Protoplasts Isolation and Culture, Handbook of Plant Cell Culture*, pp 124-176, Macmillan Publishing Company, New York; and Binding (1985) *Regeneration of Plants, Plant Protoplasts* pp 21-73, CRC Press, Boca Raton. Regeneration can also be obtained from plant callus, explants, organs, or parts thereof. Such regeneration techniques are described generally in Klee et al. (1987) *Ann Rev of Plant Phys* 38:467. See also, e.g., Payne and Gamborg.

One of skill will recognize that after the expression cassette containing the GLYAT gene is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included, provided that these parts comprise cells comprising the GLYAT nucleic acid. Progeny and variants, and mutants of the regenerated plants are also included, provided that these parts comprise the introduced nucleic acid sequences.

In one embodiment, a homozygous transgenic plant can be obtained by sexually mating (selfing) a heterozygous transgenic plant that contains a single added heterologous nucleic acid, germinating some of the seed produced and analyzing the resulting plants produced for altered cell division relative to a control plant (i.e., native, non-transgenic). Back-crossing to a parental plant and out-crossing with a non-transgenic plant are also contemplated.

Animal and lower eukaryotic (e.g., yeast) host cells are competent or rendered competent for transfection by various means. There are several well-known methods of introducing DNA into animal cells. These methods include: calcium phosphate precipitation; fusion of the recipient cells with bacterial protoplasts containing the DNA; treatment of the recipient cells with liposomes containing the DNA; DEAE dextran; electroporation; biolistics; and micro-injection of the DNA directly into the cells. The transfected cells are cultured by means well known in the art. See, Kuchler, R. J., *Biochemical Methods in Cell Culture and Virology*, Dowden, Hutchinson and Ross, Inc. (1977).

II. Methods of Use

A. Methods for Increasing Expression and/or Activity Level of at Least One GLYAT Sequence or an Active Variant or Fragment Therefore in an Host Cell of Interest, a Plant or Plant Part Various methods are provided for the expression of a GLYAT sequence or active variant or fragment thereof in a host cell of interest. For example, the host cell of interest is transformed with the GLYAT sequence and the cells are cultured under conditions which allow for the expression of the GLYAT sequence. In some embodiments, the cells are harvested by centrifugation, disrupted by physical or chemical means, and the resulting crude extract retained for further purification. Microbial cells employed in the expression of proteins can be disrupted by any convenient method, including freeze-thaw cycling, sonication, mechanical disruption, or use of cell lysing agents, or other methods, which are well known to those skilled in the art.

As noted, many references are available for the culture and production of many cells, including cells of bacterial, plant, animal (especially mammalian) and archebacterial origin. See e.g., Sambrook, Ausubel, and Berger (all supra), as well as Freshney (1994) *Culture of Animal Cells, a Manual of Basic Technique*, $3^{rd}$ Ed., Wiley-Liss, New York and the references cited therein; Doyle and Griffiths (1997) *Mammalian Cell Culture: Essential Techniques* John Wiley and Sons, NY; Humason (1979) *Animal Tissue Techniques*, $4^{th}$ Ed. W. H. Freeman and Company; and Ricciardelli, et al., (1989) *In vitro Cell Dev. Biol.* 25:1016-1024. For plant cell culture and regeneration see, Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture*; Fundamental Methods Springer Lab Manual, Springer-Verlag (Berlin, Heidelberg, New York); Jones, ed. (1984) *Plant Gene Transfer and Expression Protocols*, Humana Press, Totowa, N.J.; and *Plant Molecular Biology* (1993) R. R. D. Croy, ed. Bios Scientific Publishers, Oxford, U.K. ISBN 0 12 198370 6. Cell culture media in general are set forth in Atlas and Parks (eds.) *The Handbook of Microbiological Media* (1993) CRC Press, Boca Raton, Fla. Additional information for cell culture is found in available commercial literature such as the *Life Science Research Cell Culture Catalogue* (1998) from Sigma-Aldrich, Inc. (St Louis, Mo.) ("Sigma-LSRCCC") and, e.g., *The Plant Culture Catalogue* and supplement (1997) also from Sigma-Aldrich, Inc. (St Louis, Mo.) ("Sigma-PCCS").

A method for increasing the activity of a GLYAT polypeptide disclosed herein or an active variant or fragment thereof in a plant, plant cell, plant part, explant, and/or seed is provided. In further embodiments, the activity of the GLYAT polypeptide is increased in a plant or plant part by at least 10%, 20%, 30%, 40%, 50%, 60%, 70%, 80%, 90%, 100%, 200%, 500%, 1000%, 5000%, or 10,000% relative to an appropriate control plant, plant part, or cell. In still other embodiments, the activity level of the GLYAT polypeptide in the plant or plant part is increased by 10, 20, 30, 40, 50, 60, 70, 80, 90, 100 fold or more relative to an appropriate control plant, plant part, or cell. Such an increase in the activity of the GLYAT polypeptide in the cell can be achieved in a variety of ways including, for example, by the expression of multiple copies of one or more GLYAT polypeptide, by employing a promoter to drive higher levels of expression of the sequence, or by employing a GLYAT sequence having an increased level of activity.

In specific embodiments, the polypeptide or the GLYAT polynucleotide or active variant or fragment thereof is introduced into the plant, plant cell, explant or plant part. Subsequently, a plant cell having an introduced sequence disclosed herein is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the temporal or spatial expression of polypeptides disclosed herein in the plant. Plant forming conditions are well known in the art and discussed briefly elsewhere herein.

In one embodiment, a method of producing a glyphosate tolerant plant cell is provided and comprises transforming a plant cell with the polynucleotide encoding a GLYAT polypeptide or active variant or fragment thereof. In specific embodiments, the method further comprises selecting a plant cell which is resistant or tolerant to a glyphosate by growing the plant cells in a sufficient concentration of glyphosate, such that the herbicide kills the plant cells which do not comprise the GLYAT polypeptide of interest.

B. Method of Producing Crops and Controlling Weeds

Methods for controlling weeds in an area of cultivation, preventing the development or the appearance of herbicide resistant weeds in an area of cultivation, producing a crop, and increasing crop safety are provided. The term "controlling," and derivations thereof, for example, as in "controlling weeds" refers to one or more of inhibiting the growth, germination, reproduction, and/or proliferation of; and/or killing, removing, destroying, or otherwise diminishing the occurrence and/or activity of a weed.

As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc.

As used herein, by "selectively controlled" it is intended that the majority of weeds in an area of cultivation are significantly damaged or killed, while if crop plants are also present in the field, the majority of the crop plants are not significantly damaged. Thus, a method is considered to selectively control weeds when at least 55%, 60%, 65%, 70%, 75%, 80%, 85%, 90%, 95%, or more of the weeds are significantly damaged or killed, while if crop plants are also present in the field, less than 10%, 5%, or 1% of the crop plants are significantly damaged or killed.

Methods provided comprise planting the area of cultivation with a plant having a GLYAT sequence or active variant or fragment thereof disclosed herein or transgenic seed derived therefrom, and in specific embodiments, applying to the crop, seed, weed or area of cultivation thereof an effective amount of a herbicide of interest. It is recognized that the herbicide can be applied before or after the crop is planted in the area of cultivation. Such herbicide applications can include an application of glyphosate.

Accordingly, the term "glyphosate" should be considered to include any herbicidally effective form of N-phosphonomethylglycine (including any salt thereof) and other forms which result in the production of the glyphosate anion in planta.

In specific methods, glyphosate is applied to the plants having the GLYAT sequence or active variant or fragment thereof or their area of cultivation. In specific embodiments, the glyphosate is in the form of a salt, such as, ammonium, isopropylammonium, potassium, sodium (including sesquisodium) or trimesium (alternatively named sulfosate). In still further embodiments, a mixture of a synergistically effective amount of a combination of glyphosate and an ALS inhibitor (such as a sulfonylurea) is applied to the plants or their area of cultivation.

Generally, the effective amount of herbicide applied to the field is sufficient to selectively control the weeds without significantly affecting the crop. It is important to note that it is not necessary for the crop to be totally insensitive to the herbicide, so long as the benefit derived from the inhibition of weeds outweighs any negative impact of the glyphosate or glyphosate analog on the crop or crop plant.

"Weed" as used herein refers to a plant which is not desirable in a particular area. Conversely, a "crop plant" as used herein refers to a plant which is desired in a particular area, such as, for example, a maize or soy plant. Thus, in some embodiments, a weed is a non-crop plant or a non-crop species, while in some embodiments, a weed is a crop species which is sought to be eliminated from a particular area, such as, for example, an inferior and/or non-transgenic soy plant in a field planted with a plant having the GLYAT sequence disclosed herein or an active variant or fragment thereof.

Accordingly, the current disclosure provides methods for selectively controlling weeds in a field containing a crop that involve planting the field with crop seeds or plants which are glyphosate-tolerant as a result of being transformed with a gene encoding a glyphosate-N-acetyltransferase disclosed herein or an active variant or fragment thereof, and applying to the crop and weeds in the field a sufficient amount of glyphosate to control the weeds without significantly affecting the crop.

Further provided are methods for controlling weeds in a field and preventing the emergence of glyphosate resistant weeds in a field containing a crop which involve planting the field with crop seeds or plants that are glyphosate tolerant as a result of being transformed with a gene encoding a glyphosate-N-acetyltransferase and a gene encoding a polypeptide imparting glyphosate tolerance by another mechanism, such as, a glyphosate-tolerant 5-enolpyruvylshikimate-3-phosphate synthase and/or a glyphosate-tolerant glyphosate oxido-reductase and applying to the crop and the weeds in the field a sufficient amount of glyphosate to control the weeds without significantly affecting the crop. Various plants that can be used in this method are discussed in detail elsewhere herein.

In further embodiments, the current disclosure provides methods for controlling weeds in a field and preventing the emergence of herbicide resistant weeds in a field containing a crop which involve planting the field with crop seeds or plants that are glyphosate tolerant as a result of being transformed with a gene encoding a glyphosate-N-acetyltransferase, a gene encoding a polypeptide imparting glyphosate tolerance by another mechanism, such as, a glyphosate-insensitive 5-enolpyruvylshikimate-3-phosphate synthase and/or a glyphosate oxido-reductase and a gene encoding a polypeptide imparting tolerance to an additional herbicide, such as, a mutated hydroxyphenylpyruvatedioxygenase, a sulfonylurea-tolerant acetolactate synthase, a sulfonylurea-tolerant acetohydroxy acid synthase, a sulfonamide-tolerant acetolactate synthase, a sulfonamide-tolerant acetohydroxy acid synthase, an imidazolinone-tolerant acetolactate synthase, an imidazolinone-tolerant acetohydroxy acid synthase, a phosphinothricin acetyl transferase and a mutated protoporphyrinogen oxidase and applying to the crop and the weeds in the field a sufficient amount of glyphosate and an additional herbicide, such as, a hydroxyphenylpyruvatedioxygenase inhibitor, sulfonamide, imidazolinone, bialaphos, phosphinothricin, azafenidin, butafenacil, sulfosate, glufosinate, and a protox inhibitor to control the weeds without significantly affecting the crop. Various plants and seeds that can be used in this method are discussed in detail elsewhere herein.

Further provided are methods for controlling weeds in a field and preventing the emergence of herbicide resistant weeds in a field containing a crop which involve planting the field with crop seeds or plants that are glyphosate tolerant as a result of being transformed with a gene encoding a glyphosate-N-acetyltransferase and a gene encoding a polypeptide imparting tolerance to an additional herbicide, such as, a mutated hydroxyphenylpyruvatedioxygenase, a sulfonamide-tolerant acetolactate synthase, a sulfonamide-tolerant acetohydroxy acid synthase, an imidazolinone-tolerant acetolactate synthase, an imidazolinone-tolerant acetohydroxy acid synthase, a phosphinothricin acetyl transferase and a mutated protoporphyrinogen oxidase and applying to the crop and the weeds in the field a sufficient amount of glyphosate and an additional herbicide, such as, a hydroxyphenylpyruvatedioxygenase inhibitor, sulfonamide, imidazolinone, bialaphos, phosphinothricin, azafenidin, butafenacil, sulfosate, glufosinate, and a protox inhibitor to control the weeds without significantly affecting the crop. Various plants and seeds that can be used in this method are discussed in detail elsewhere herein.

Further provided is a method for producing a crop by growing a crop plant that is tolerant to glyphosate as a result of being transformed with a GLYAT polynucleotide or active variant or fragment thereof disclosed herein, under conditions such that the crop plant produces a crop, and harvesting the crop. Preferably, the glyphosate is applied to the plant, or in the vicinity of the plant, at a concentration effective to control weeds without preventing the transgenic crop plant from growing and producing the crop. The application of the glyphosate can be before planting, or at any time after planting up to and including the time of harvest. Glyphosate can be applied once or multiple times. The timing of glyphosate application, amount applied, mode of application, and other parameters will vary based upon the specific nature of the crop plant and the growing environment, and can be readily determined by one of skill in the art. A crop produced by this method is also provided.

Further provided are methods for the propagation of a plant containing a GLYAT polypeptide or active variant or fragment thereof. The plant can be, for example, a monocot or a dicot. In one aspect, propagation entails crossing a plant containing a GLYAT polynucleotide transgene with a second plant, such that at least some progeny of the cross display glyphosate tolerance.

The methods herein further allow for the development of herbicide applications to be used with the plants having the GLYAT sequence or active variants or fragments thereof. In such methods, the environmental conditions in an area of cultivation are evaluated. Environmental conditions that can be evaluated include, but are not limited to, ground and surface water pollution concerns, intended use of the crop, crop tolerance, soil residuals, weeds present in area of cultivation, soil texture, pH of soil, amount of organic matter in soil, application equipment, and tillage practices. Upon the evaluation of the environmental conditions, an effective amount of a combination of herbicides can be applied to the crop, crop part, and seed of the crop or area of cultivation.

Any herbicide or combination of herbicides can be applied to the plant having the GLYAT sequence or active variant or fragment thereof disclosed herein or transgenic seed derived there from, crop part, or the area of cultivation containing the crop plant. By "treated with a combination of" or "applying a combination of" herbicides to a crop, area of cultivation or field" it is intended that a particular field, crop or weed is treated with each of the herbicides and/or chemicals indicated to be part of the combination so that a desired effect is achieved, i.e., so that weeds are selectively controlled while the crop is not significantly damaged. The application of each herbicide and/or chemical may be simultaneous or the applications may be at different times (sequential), so long as the desired effect is achieved. Furthermore, the application can occur prior to the planting of the crop.

Classifications of herbicides (i.e., the grouping of herbicides into classes and subclasses) are well-known in the art and include classifications by HRAC (Herbicide Resistance Action Committee) and WSSA (the Weed Science Society of America) (see also, Retzinger and Mallory-Smith (1997) *Weed Technology* 11: 384-393). An abbreviated version of the HRAC classification (with notes regarding the corresponding WSSA group) is set forth below in Table 1.

Herbicides can be classified by their mode of action and/or site of action and can also be classified by the time at which they are applied (e.g., preemergent or postemergent), by the method of application (e.g., foliar application or soil application), or by how they are taken up by or affect the plant or by their structure. "Mode of action" generally refers to the metabolic or physiological process within the plant that the herbicide inhibits or otherwise impairs, whereas "site of action" generally refers to the physical location or biochemical site within the plant where the herbicide acts or directly interacts. Herbicides can be classified in various ways, including by mode of action and/or site of action (see, e.g., Table 1).

Often, an herbicide-tolerance gene that confers tolerance to a particular herbicide or other chemical on a plant expressing it will also confer tolerance to other herbicides or chemicals in the same class or subclass, for example, a class or subclass set forth in Table 1. Thus, in some embodiments, a transgenic plant is tolerant to more than one herbicide or chemical in the same class or subclass, such as, for example, an HPPD inhibitor, glyphosate, an ALS chemistry, an inhibitor of PPO, a sulfonylurea, and/or a synthetic auxin.

Typically, the plants of the present disclosure can tolerate treatment with different types of herbicides (i.e., herbicides having different modes of action and/or different sites of action) thereby permitting improved weed management strategies that are recommended in order to reduce the incidence and prevalence of herbicide-tolerant weeds.

TABLE 1

Abbreviated version of HRAC Herbicide Classification

I. ALS Inhibitors (WSSA Group 2)
   A. Sulfonylureas
      1. Azimsulfuron
      2. Chlorimuron-ethyl
      3. Metsulfuron-methyl
      4. Nicosulfuron
      5. Rimsulfuron
      6. Sulfometuron-methyl
      7. Thifensulfuron-methyl
      8. Tribenuron-methyl
      9. Amidosulfuron
      10. Bensulfuron-methyl
      11. Chlorsulfuron
      12. Cinosulfuron
      13. Cyclosulfamuron
      14. Ethametsulfuron-methyl
      15. Ethoxysulfuron
      16. Flazasulfuron
      17. Flupyrsulfuron-methyl
      18. Foramsulfuron
      19. Imazosulfuron
      20. Iodosulfuron-methyl
      21. Mesosulfuron-methyl
      22. Oxasulfuron
      23. Primisulfuron-methyl
      24. Prosulfuron
      25. Pyrazosulfuron-ethyl
      26. Sulfosulfuron
      27. Triasulfuron
      28. Trifloxysulfuron
      29. Triflusulfuron-methyl
      30. Tritosulfuron
      31. Halosulfuron-methyl
      32. Flucetosulfuron
   B. Sulfonylaminocarbonyltriazolinones
      1. Flucarbazone
      2. Procarbazone
   C. Triazolopyrimidines
      1. Cloransulam-methyl
      2. Flumetsulam
      3. Diclosulam
      4. Florasulam
      5. Metosulam
      6. Penoxsulam
      7. Pyroxsulam
   D. Pyrimidinyloxy(thio)benzoates
      1. Bispyribac
      2. Pyriftalid
      3. Pyribenzoxim
      4. Pyrithiobac
      5. Pyriminobac-methyl
   E. Imidazolinones
      1. Imazapyr
      2. Imazethapyr
      3. Imazaquin
      4. Imazapic
      5. Imazamethabenz-methyl
      6. Imazamox
II. Other Herbicides--Active Ingredients/Additional Modes of Action
   A. Inhibitors of Acetyl CoA carboxylase (ACCase) (WSSA Group 1)
      1. Aryloxyphenoxypropionates ('FOPs')
         a. Quizalofop-P-ethyl
         b. Diclofop-methyl
         c. Clodinafop-propargyl
         d. Fenoxaprop-P-ethyl
         e. Fluazifop-P-butyl
         f. Propaquizafop
         g. Haloxyfop-P-methyl
         h. Cyhalofop-butyl
         i. Quizalofop-P-ethyl
      2. Cyclohexanediones ('DIMs')
         a. Alloxydim
         b. Butroxydim
         c. Clethodim
         d. Cycloxydim
         e. Sethoxydim
         f. Tepraloxydim
         g. Tralkoxydim
   B. Inhibitors of Photosystem II - HRAC Group C1/WSSA Group 5
      1. Triazines
         a. Ametryne
         b. Atrazine
         c. Cyanazine
         d. Desmetryne
         e. Dimethametryne
         f. Prometon
         g. Prometryne
         h. Propazine
         i. Simazine
         j. Simetryne
         k. Terbumeton
         l. Terbuthylazine
         m. Terbutryne
         n. Trietazine
      2. Triazinones
         a. Hexazinone
         b. Metribuzin
         c. Metamitron
      3. Triazolinone
         a. Amicarbazone
      4. Uracils
         a. Bromacil
         b. Lenacil
         c. Terbacil
      5. Pyridazinones
         a. Pyrazon
      6. Phenyl carbamates
         a. Desmedipham
         b. Phenmedipham
   C. Inhibitors of Photosystem II--HRAC Group C2/WSSA Group 7
      1. Ureas
         a. Fluometuron
         b. Linuron
         c. Chlorbromuron
         d. Chlorotoluron
         e. Chloroxuron
         f. Dimefuron
         g. Diuron
         h. Ethidimuron
         i. Fenuron
         j. Isoproturon TABLE 1-continued Abbreviated version of HRAC Herbicide Classification k. Isouron
    l. Methabenzthiazuron
    m. Metobromuron
    n. Metoxuron
    o. Monolinuron
    p. Neburon
    q. Siduron
    r. Tebuthiuron
  2. Amides
    a. Propanil
    b. Pentanochlor
D. Inhibitors of Photosystem II--HRAC Group C3/WSSA Group 6
  1. Nitriles
    a. Bromofenoxim
    b. Bromoxynil
    c. Ioxynil
  2. Benzothiadiazinone (Bentazon)
    a. Bentazon
  3. Phenylpyridazines
    a. Pyridate
    b. Pyridafol
E. Photosystem-I-electron diversion (Bipyridyliums) (WSSA Group 22)
  1. Diquat
  2. Paraquat
F. Inhibitors of PPO (protoporphyrinogen oxidase) (WSSA Group 14)
  1. Diphenylethers
    a. Acifluorfen-Na
    b. Bifenox
    c. Chlomethoxyfen
    d. Fluoroglycofen-ethyl
    e. Fomesafen
    f. Halosafen
    g. Lactofen
    h. Oxyfluorfen
  2. Phenylpyrazoles
    a. Fluazolate
    b. Pyraflufen-ethyl
  3. N-phenylphthalimides
    a. Cinidon-ethyl
    b. Flumioxazin
    c. Flumiclorac-pentyl
  4. Thiadiazoles
    a. Fluthiacet-methyl
    b. Thidiazimin
  5. Oxadiazoles
    a. Oxadiazon
    b. Oxadiargyl
  6. Triazolinones
    a. Carfentrazone-ethyl
    b. Sulfentrazone
  7. Oxazolidinediones
    a. Pentoxazone
  8. Pyrimidindiones
    a. Benzfendizone
    b. Butafenicil
  9. Others
    a. Pyrazogyl
    b. Profluazol
G. Bleaching: Inhibition of carotenoid biosynthesis at the phytoene desaturase step (PDS) (WSSA Group 12)
  1. Pyridazinones
    a. Norflurazon
  2. Pyridinecarboxamides
    a. Diflufenican
    b. Picolinafen
  3. Others
    a. Beflubutamid
    b. Fluridone
    c. Flurochloridone
    d. Flurtamone
H. Bleaching: Inhibition of 4-hydroxphenyl-pyruvate-dioxygenase (4-HPPD) (WSSA Group 28)
  1. Triketones
    a. Mesotrione
    b. Sulcotrione
    c. topramezone
    d. tembotrione
  2. Isoxazoles
    a. Pyrasulfotole
    b. Isoxaflutole
  3. Pyrazoles
    a. Benzofenap
    b. Pyrazoxyfen
    c. Pyrazolynate
  4. Others
    a. Benzobicyclon
I. Bleaching: Inhibition of carotenoid biosynthesis (unknown target) (WSSA Group 11 and 13)
  1. Triazoles (WSSA Group 11)
    a. Amitrole
  2. Isoxazolidinones (WSSA Group 13)
    a. Clomazone
  3. Ureas
    a. Fluometuron
  3. Diphenylether
    a. Aclonifen
J. Inhibition of EPSP Synthase
  1. Glycines (WSSA Group 9)
    a. Glyphosate
    b. Sulfosate
K. Inhibition of glutamine synthetase
  1. Phosphinic Acids
    a. Glufosinate-ammonium
    b. Bialaphos
L. Inhibition of DHP (dihydropteroate) synthase (WSSA Group 18)
  1 Carbamates
    a. Asulam
M. Microtubule Assembly Inhibition (WSSA Group 3)
  1. Dinitroanilines
    a. Benfluralin
    b. Butralin
    c. Dinitramine
    d. Ethalfluralin
    e. Oryzalin
    f. Pendimethalin
    g. Trifluralin
  2. Phosphoroamidates
    a. Amiprophos-methyl
    b. Butamiphos
  3. Pyridines
    a. Dithiopyr
    b. Thiazopyr
  4. Benzamides
    a. Pronamide
    b. Tebutam
  5. Benzenedicarboxylic acids
    a. Chlorthal-dimethyl
N. Inhibition of mitosis/microtubule organization WSSA Group 23)
  1. Carbamates
    a. Chlorpropham
    b. Propham
    c. Carbetamide
O. Inhibition of cell division (Inhibition of very long chain fatty acids as proposed mechanism; WSSA Group 15)
  1. Chloroacetamides
    a. Acetochlor
    b. Alachlor
    c. Butachlor

TABLE 1-continued

Abbreviated version of HRAC Herbicide Classification d. Dimethachlor
        e. Dimethanamid
        f. Metazachlor
        g. Metolachlor
        h. Pethoxamid
        i. Pretilachlor
        j. Propachlor
        k. Propisochlor
        l. Thenylchlor
    2. Acetamides
        a. Diphenamid
        b. Napropamide
        c. Naproanilide
    3. Oxyacetamides
        a. Flufenacet
        b. Mefenacet
    4. Tetrazolinones
        a. Fentrazamide
    5. Others
        a. Anilofos
        b. Cafenstrole
        c. Indanofan
        d. Piperophos
P. Inhibition of cell wall (cellulose) synthesis
    1. Nitriles (WSSA Group 20)
        a. Dichlobenil
        b. Chlorthiamid
    2. Benzamides (isoxaben (WSSA Group 21))
        a. Isoxaben
    3. Triazolocarboxamides (flupoxam)
        a. Flupoxam
Q. Uncoupling (membrane disruption): (WSSA Group 24)
    1. Dinitrophenols
        a. DNOC
        b. Dinoseb
        c. Dinoterb
R. Inhibition of Lipid Synthesis by other than ACC inhibition
    1. Thiocarbamates (WSSA Group 8)
        a. Butylate
        b. Cycloate
        c. Dimepiperate
        d. EPTC
        e. Esprocarb
        f. Molinate
        g. Orbencarb
        h. Pebulate
        i. Prosulfocarb
        j. Benthiocarb
        k. Tiocarbazil
        l. Triallate
        m. Vernolate
    2. Phosphorodithioates
        a. Bensulide
    3. Benzofurans
        a. Benfuresate
        b. Ethofumesate
    4. Halogenated alkanoic acids (WSSA Group 26)
        a. TCA
        b. Dalapon
        c. Flupropanate
S. Synthetic auxins (IAA-like) (WSSA Group 4)
    1. Phenoxycarboxylic acids
        a. Clomeprop
        b. 2,4-D
        c. Mecoprop
    2. Benzoic acids
        a. Dicamba
        b. Chloramben
        c. TBA
    3. Pyridine carboxylic acids
        a. Clopyralid
        b. Fluroxypyr
        c. Picloram
        d. Tricyclopyr
    4. Quinoline carboxylic acids
        a. Quinclorac
        b. Quinmerac
    5. Others (benazolin-ethyl)
        a. Benazolin-ethyl
T. Inhibition of Auxin Transport
    1. Phthalamates; semicarbazones (WSSA Group 19)
        a. Naptalam
        b. Diflufenzopyr-Na
U. Other Mechanism of Action
    1. Arylaminopropionic acids
        a. Flamprop-M-methyl/-isopropyl
    2. Pyrazolium
        a. Difenzoquat
    3. Organoarsenicals
        a. DSMA
        b. MSMA
    4. Others
        a. Bromobutide
        b. Cinmethylin
        c. Cumyluron
        d. Dazomet
        e. Daimuron-methyl
        f. Dimuron
        g. Etobenzanid
        h. Fosamine
        i. Metam
        j. Oxaziclomefone
        k. Oleic acid
        l. Pelargonic acid
        m. Pyributicarb In still further methods, glyphosate can be applied alone or in combination with another herbicide of interest and can be applied to the plants having the GLYAT sequence as disclosed herein or their area of cultivation.

Additional herbicide treatment that can be applied over the plants or seeds having the GLYAT polypeptides or active variants and fragments thereof include, but are not limited to: acetochlor, acifluorfen and its sodium salt, aclonifen, acrolein (2-propenal), alachlor, alloxydim, ametryn, amicarbazone, amidosulfuron, aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clethodim, clodinafop-propargyl, clomazone, clomeprop, clopyralid, clopyralid-olamine, cloransulam-methyl, CUH-35 (2-methoxyethyl 2-[[[4-chloro-2-fluoro-5-[(1-methyl-2-propynyl)oxy]phenyl](3-fluorobenzoyl)amino]carbonyl]-1-cyclohexene-1-carboxylate), cumyluron, cyanazine, cycloate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethofumesate, ethoxyfen, ethoxysulfuron, etobenzanid, fenoxaprop-ethyl, fenoxaprop-P-ethyl, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glyphosate and its salts such as ammonium, isopropylammonium, potassium, sodium (including sesquisodium) and trimesium (alternatively named sulfosate) (See, WO2007/024782, herein incorporated by reference), halosulfuron-methyl, haloxyfop-etotyl, haloxyfop-methyl, hexazinone, HOK-201 (N-(2,4-difluorophenyl)-1,5-dihydro-N-(1-methylethyl)-5-oxo-1-[(tetrahydro-2H-pyran-2-yl)methyl]-4H-1,2,4-triazole-4-carboxamide), imazamethabenz-methyl, imazamox, imazapic, imazapyr, imazaquin, imazaquin-ammonium, imazethapyr, imazethapyr-ammonium, imazosulfuron, indanofan, iodosulfuron-methyl, ioxynil, ioxynil octanoate, ioxynil-sodium, isoproturon, isouron, isoxaben, isoxaflutole, pyrasulfotole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, naptalam, neburon, nicosulfuron, norflurazon, orbencarb, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxyamid, phenmedipham, picloram, picloram-potassium, picolinafen, pinoxaden, piperofos, pretilachlor, prim isulfuron-methyl, prodiamine, profoxydim, prometon, prometryn, propachlor, propanil, propaquizafop, propazine, propham, propisochlor, propoxycarbazone, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxsulam, quinclorac, quinmerac, quinoclamine, quizalofop-ethyl, quizalofop-P-ethyl, quizalofop-P-tefuryl, rimsulfuron, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiocarbazil, topramezone, tralkoxydim, tri-allate, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron and vernolate.

Additional herbicides include those that are applied over plants having homogentisate solanesyltransferase (HST) polypeptide such as those described in WO2010029311 (A2), herein incorporated by reference it its entirety.

Other herbicides that can be used when an HPPD inhibitor tolerant sequence is present in the plant (in addition to a GLYAT sequence disclosed herein) include, but are not limited to, triketones (such as, mesotrione, sulcotrione, topremezone, and tembotrione) including agriculturally suitable salts (e.g., sodium salts) thereof; isoxazoles (such as, pyrasulfotole and isoxaflutole) including agriculturally suitable salts (e.g., sodium salts) thereof; pyrazoles (such as, benzofenap, pyrazoxyfen, and pyrazolynate) including agriculturally suitable salts (e.g., sodium salts) thereof; and benzobicyclon, including agriculturally suitable salts (e.g., sodium salts) thereof. See, WO2005/053407. In specific embodiments, a combination of two or more HPPD inhibitors is applied.

In some embodiments, topical application of polynucleotides (e.g., dsRNA, ssRNA, constructs expressing hairpin dsRNA, RNA molecules comprising synthetic nucleotides) to control weeds in crop growing field include crop plants expressing GLYAT sequences disclosed herein. Such weed control options include RNA suppression techniques that target one or more specific endogenous transcripts present in weeds, but do not substantially impact the crop plants that are tolerant to glyphosate.

Other suitable herbicides and agricultural chemicals are known in the art, such as, for example, those described in WO 2005/041654. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub. Combinations of various herbicides can result in a greater-than-additive (i.e., synergistic) effect on weeds and/or a less-than-additive effect (i.e. safening) on crops or other desirable plants. In certain instances, combinations of glyphosate with other herbicides having a similar spectrum of control but a different mode of action will be particularly advantageous for preventing the development of resistant weeds.

The time at which a herbicide is applied to an area of interest (and any plants therein) may be important in optimizing weed control. The time at which a herbicide is applied may be determined with reference to the size of plants and/or the stage of growth and/or development of plants in the area of interest, e.g., crop plants or weeds growing in the area.

Ranges of the effective amounts of herbicides can be found, for example, in various publications from University Extension services. See, for example, Bernards et al. (2006) *Guide for Weed Management in Nebraska* (www.ianrpubs.url.edu/sendlt/ec130); Regher et al. (2005) *Chemical Weed Control for Fields Crops, Pastures, Rangeland, and Non-cropland*, Kansas State University Agricultural Extension Station and Corporate Extension Service; Zollinger et al. (2006) *North Dakota Weed Control Guide*, North Dakota Extension Service, and the Iowa State University Extension at www.weeds.iastate.edu, each of which is herein incorporated by reference.

Many plant species can be controlled (i.e., killed or damaged) by the herbicides described herein. Accordingly, the methods of the disclosure are useful in controlling these plant species where they are undesirable (i.e., where they are weeds). These plant species include crop plants as well as species commonly considered weeds, including but not limited to species such as: blackgrass (*Alopecurus myosuroides*), giant foxtail (*Setaria faberi*), large crabgrass (*Digitaria sanguinalis*), Surinam grass (*Brachiaria decumbens*), wild oat (*Avena fatua*), common cocklebur (*Xanthium pensylvanicum*), common lambsquarters (*Chenopodium album*), morning glory (*Ipomoea coccinea*), pigweed (*Amaranthus* spp.), velvetleaf (*Abutilion theophrasti*), common barnyardgrass (*Echinochloa crusgalli*), bermudagrass (*Cynodon dactylon*), downy brome (*Bromus tectorum*), goosegrass (*Eleusine indica*), green foxtail (*Setaria viridis*), Italian ryegrass (*Lolium multiflorum*), Johnsongrass (*Sorghum halepense*), lesser canarygrass (*Phalaris minor*), windgrass (*Apera spica-venti*), wooly cupgrass (*Erichloa villosa*), yellow nutsedge (*Cyperus esculentus*), common chickweed (*Stellaria media*), common ragweed (*Ambrosia artemisiifolia*), *Kochia scoparia*, horseweed (*Conyza canadensis*), rigid ryegrass (*Lolium rigidum*), goosegrass (*Eleucine indica*), hairy fleabane (*Conyza bonariensis*), buckhorn plantain (*Plantago lanceolata*), tropical spiderwort (*Commelina benghalensis*), field bindweed (*Convolvulus arvensis*), purple nutsedge (*Cyperus rotundus*), redvine (*Brunnichia ovata*), hemp *sesbania* (*Sesbania exaltata*), sicklepod (*Senna obtusifolia*), Texas blueweed (*Helianthus ciliaris*), and Devil's claws (*Proboscidea louisianica*). In other embodiments, the weed comprises a herbicide-resistant ryegrass, for example, a glyphosate resistant ryegrass, a paraquat resistant ryegrass, a ACCase-inhibitor resistant ryegrass, and a non-selective herbicide resistant ryegrass.

In some embodiments, a plant having the GLYAT sequence disclosed herein or active variants and fragments thereof is not significantly damaged by treatment with the glyphosate applied to that plant, whereas an appropriate control plant is significantly damaged by the same treatment.

Generally, the glyphosate is applied to a particular field (and any plants growing in it) no more than 1, 2, 3, 4, 5, 6, 7, or 8 times a year, or no more than 1, 2, 3, 4, or 5 times per growing season.

Thus, methods of the disclosure encompass applications of herbicide which are "preemergent," "postemergent," "preplant incorporation" and/or which involve seed treatment prior to planting.

In one embodiment, methods are provided for coating seeds. The methods comprise coating a seed with an effective amount of a herbicide or a combination of herbicides (as disclosed elsewhere herein). The seeds can then be planted in an area of cultivation. Further provided are seeds having a coating comprising an effective amount of a herbicide or a combination of herbicides (as disclosed elsewhere herein). In other embodiments, the seeds can be coated with at least one fungicide and/or at least one insecticide and/or at least one herbicide or any combination thereof.

"Preemergent" refers to a herbicide which is applied to an area of interest (e.g., a field or area of cultivation) before a plant emerges visibly from the soil. "Postemergent" refers to a herbicide which is applied to an area after a plant emerges visibly from the soil. In some instances, the terms "preemergent" and "postemergent" are used with reference to a weed in an area of interest, and in some instances these terms are used with reference to a crop plant in an area of interest. When used with reference to a weed, these terms may apply to only a particular type of weed or species of weed that is present or believed to be present in the area of interest. While any herbicide may be applied in a preemergent and/or postemergent treatment, some herbicides are known to be more effective in controlling a weed or weeds when applied either preemergence or postemergence. For example, rimsulfuron has both preemergence and postemergence activity, while other herbicides have predominately preemergence (metolachlor) or postemergence (glyphosate) activity. These properties of particular herbicides are known in the art and are readily determined by one of skill in the art. Further, one of skill in the art would readily be able to select appropriate herbicides and application times for use with the transgenic plants disclosed herein and/or on areas in which the transgenic plants are to be planted. "Preplant incorporation" involves the incorporation of compounds into the soil prior to planting.

Thus, improved methods of growing a crop and/or controlling weeds such as, for example, "pre-planting burn down," are provided wherein an area is treated with herbicides prior to planting the crop of interest in order to better control weeds. The disclosure also provides methods of growing a crop and/or controlling weeds which are "no-till" or "low-till" (also referred to as "reduced tillage"). In such methods, the soil is not cultivated or is cultivated less frequently during the growing cycle in comparison to traditional methods; these methods can save costs that would otherwise be incurred due to additional cultivation, including labor and fuel costs.

The term "safener" refers to a substance that when added to a herbicide formulation eliminates or reduces the phytotoxic effects of the herbicide to certain crops. One of ordinary skill in the art would appreciate that the choice of safener depends, in part, on the crop plant of interest and the particular herbicide or combination of herbicides. Exemplary safeners suitable for use with the presently disclosed herbicide compositions include, but are not limited to, those disclosed in U.S. Pat. Nos. 4,808,208; 5,502,025; 6,124,240 and U.S. Patent Application Publication Nos. 2006/0148647; 2006/0030485; 2005/0233904; 2005/0049145; 2004/0224849; 2004/0224848; 2004/0224844; 2004/0157737; 2004/0018940; 2003/0171220; 2003/0130120; 2003/0078167, the disclosures of which are incorporated herein by reference in their entirety. The methods of the disclosure can involve the use of herbicides in combination with herbicide safeners such as benoxacor, BCS (1-bromo-4-[(chloromethyl) sulfonyl]benzene), cloquintocet-mexyl, cyometrinil, dichlormid, 2-(dichloromethyl)-2-methyl-1,3-dioxolane (MG 191), fenchlorazole-ethyl, fenclorim, flurazole, fluxofenim, furilazole, isoxadifen-ethyl, mefenpyr-diethyl, methoxyphenone ((4-methoxy-3-methylphenyl)(3-methylphenyl)-methanone), naphthalic anhydride (1,8-naphthalic anhydride) and oxabetrinil to increase crop safety. Antidotally effective amounts of the herbicide safeners can be applied at the same time as the compounds disclosed herein, or applied as seed treatments. Therefore an aspect of the present disclosure relates to the use of a mixture comprising glyphosate, at least one other herbicide, and an antidotally effective amount of a herbicide safener.

Seed treatment is useful for selective weed control, because it physically restricts antidoting to the crop plants. Therefore in one embodiment, a method for selectively controlling the growth of weeds in a field comprising treating the seed from which the crop is grown with an antidotally effective amount of safener and treating the field with an effective amount of herbicide to control weeds.

An antidotally effective amount of a safener is present where a desired plant is treated with the safener so that the effect of a herbicide on the plant is decreased in comparison to the effect of the herbicide on a plant that was not treated with the safener; generally, an antidotally effective amount of safener prevents damage or severe damage to the plant treated with the safener. One of skill in the art is capable of determining whether the use of a safener is appropriate and determining the dose at which a safener should be administered to a crop.

As used herein, an "adjuvant" is any material added to a spray solution or formulation to modify the action of an agricultural chemical or the physical properties of the spray solution. See, for example, Green and Foy (2003) "Adjuvants: Tools for Enhancing Herbicide Performance," in *Weed Biology and Management*, ed. Inderjit (Kluwer Academic Publishers, The Netherlands). Adjuvants can be categorized or subclassified as activators, acidifiers, buffers, additives, adherents, antiflocculants, antifoamers, defoamers, antifreezes, attractants, basic blends, chelating agents, cleaners, colorants or dyes, compatibility agents, cosolvents, couplers, crop oil concentrates, deposition agents, detergents, dispersants, drift control agents, emulsifiers, evaporation reducers, extenders, fertilizers, foam markers, formulants, inerts, humectants, methylated seed oils, high load COCs, polymers, modified vegetable oils, penetrators, repellants, petroleum oil concentrates, preservatives, rainfast agents, retention aids, solubilizers, surfactants, spreaders, stickers, spreader stickers, synergists, thickeners, translocation aids, uv protectants, vegetable oils, water conditioners, and wetting agents.

In addition, methods of the disclosure can comprise the use of a herbicide or a mixture of herbicides, as well as, one or more other insecticides, fungicides, nematocides, bactericides, acaricides, growth regulators, chemosterilants, semiochemicals, repellents, attractants, pheromones, feeding stimulants or other biologically active compounds or entomopathogenic bacteria, virus, or fungi to form a multicomponent mixture giving an even broader spectrum of agricultural protection. Examples of such agricultural protectants which can be used in methods of the disclosure include: insecticides such as abamectin, acephate, acetamiprid, amidoflumet (S-1955), avermectin, azadirachtin, azinphos-methyl, bifenthrin, bifenazate, buprofezin, carbofuran, cartap, chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyriprole, pyriproxyfen, rotenone, ryanodine, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametpyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *Aizawai*, *Bacillus thuringiensis* subsp. *Kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

The methods of controlling weeds can further include the application of a biologically effective amount of a herbicide of interest or a mixture of herbicides, and an effective amount of at least one additional biologically active compound or agent and can further comprise at least one of a surfactant, a solid diluent or a liquid diluent. Examples of such biologically active compounds or agents are: insecticides such as abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenyl-amino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), flumorf/flumorlin (SYP-L190), fluoxastrobin (HEC 5725), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metominostrobin/fenominostrobin (SSF-126), metrafenone (AC375839), myclobutanil, neo-asozin (ferric methanearsonate), nicobifen (BAS 510), orysastrobin, oxadixyl, penconazole, pencycuron, probenazole, prochloraz, propamocarb, propiconazole, proquinazid (DPX-KQ926), prothioconazole (JAU 6476), pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *Aizawai*, *Bacillus thuringiensis* subsp. *Kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV. Methods of the disclosure may also comprise the use of plants genetically transformed to express proteins (such as *Bacillus thuringiensis* delta-endotoxins) toxic to invertebrate pests. In such embodiments, the effect of exogenously applied invertebrate pest control compounds may be synergistic with the expressed toxin proteins. General references for these agricultural protectants include *The Pesticide Manual*, 13th *Edition*, C. D. S. Tomlin, Ed., British Crop Protection Council, Farnham, Surrey, U.K., 2003 and *The BioPesticide Manual*, $2^{nd}$ *Edition*, L. G. Copping, Ed., British Crop Protection Council, Farnham, Surrey, U.K., 2001.

In certain instances, combinations with other invertebrate pest control compounds or agents having a similar spectrum of control but a different mode of action will be particularly advantageous for resistance management. Thus, compositions of the present disclosure can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of this disclosure can also provide a broader spectrum of plant protection and be advantageous for resistance management.

Thus, methods of controlling weeds can employ a herbicide or herbicide combination and may further comprise the use of insecticides and/or fungicides, and/or other agricultural chemicals such as fertilizers. The use of such combined treatments disclosed herein can broaden the spectrum of activity against additional weed species and suppress the proliferation of any resistant biotypes.

Methods can further comprise the use of plant growth regulators such as aviglycine, N-(phenylmethyl)-1H-purin-6-amine, ethephon, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

C. Methods of Detection

Methods for detecting a GLYAT polypeptide or an active variant or fragment thereof are provided. Such methods comprise analyzing host cells, plant tissues or plant cells to detect such polypeptides or the polynucleotides encoding the same. The detection methods can directly assay for the presence of the GLYAT polypeptide or polynucleotide or the detection methods can indirectly assay for the sequences by assaying the phenotype of the host cell, plant, plant cell or plant explant expressing the sequence.

In one embodiment, the GLYAT polypeptide is detected in the plant tissue using an immunoassay comprising an antibody or antibodies that specifically recognizes the GLYAT polypeptide or active variant or fragment thereof. In specific embodiments, the antibody or antibodies which are used are raised to a GLYAT polypeptide or active variant or fragment thereof as disclosed herein.

By "specifically or selectively binds" is intended that the binding agent has a binding affinity for a given GLYAT polypeptide or fragment or variant disclosed herein, which is greater than 10%, 9%, 8%, 7%, 6%, 5%, 4%, 3%, 2% or 1% of the binding affinity for a known GLYAT sequence. One of skill will be aware of the proper controls that are needed to carry out such a determination By "antibodies that specifically bind" is intended that the antibodies will not substantially cross react with another polypeptide. By "not substantially cross react" is intended that the antibody or fragment thereof has a binding affinity for the other polypeptide which is less than 10%, less than 5%, or less than 1%, of the binding affinity for the GLYAT polypeptide or active fragment or variant thereof.

In still other embodiments, the GLYAT polypeptide or active variant or fragment thereof can be detected in a host cell or plant tissue by detecting the various GLYAT polypeptides or active variants and fragments thereof using mass spectrometry. By "detecting" is intended determining the presence or amount of an analyte of interest (i.e., the GLYAT polypeptide) in a test sample. The method of detection is not restricted and may be either qualitative or quantitative. The term "mass spectrometry" or "MS" as used herein generally refer to methods of filtering, detecting, and measuring ions based on their mass-to-charge ratio, or "m/z." In MS techniques, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,107,623, entitled "Methods and Apparatus for Tandem Mass Spectrometry," which is hereby incorporated by reference in its entirety.

In still other embodiments, the GLYAT polypeptide or active variant or fragment thereof can be detected in a host cell or plant tissue by detecting the presence of a polynucleotide encoding any of the various GLYAT polypeptides or active variants and fragments thereof. In one embodiment, the detection method comprises assaying plant tissue using PCR amplification.

As used herein, "primers" are isolated polynucleotides that are annealed to a complementary target DNA strand by nucleic acid hybridization to form a hybrid between the primer and the target DNA strand, then extended along the target DNA strand by a polymerase, e.g., a DNA polymerase. Primer pairs of the disclosure refer to their use for amplification of a target polynucleotide, e.g., by the polymerase chain reaction (PCR) or other conventional nucleic-acid amplification methods. "PCR" or "polymerase chain reaction" is a technique used for the amplification of specific DNA segments (see, U.S. Pat. Nos. 4,683,195 and 4,800,159; herein incorporated by reference).

Probes and primers are of sufficient nucleotide length to bind to the target DNA sequence and specifically detect and/or identify a polynucleotide encoding a GLYAT polypeptide or active variant or fragment thereof as describe elsewhere herein. It is recognized that the hybridization conditions or reaction conditions can be determined by the operator to achieve this result. This length may be of any length that is of sufficient length to be useful in a detection method of choice. Such probes and primers can hybridize specifically to a target sequence under high stringency hybridization conditions. Probes and primers according to embodiments of the present disclosure may have complete DNA sequence identity of contiguous nucleotides with the target sequence, although probes differing from the target DNA sequence and that retain the ability to specifically detect and/or identify a target DNA sequence may be designed by conventional methods. Accordingly, probes and primers can share about 80%, 85%, 90%, 91%, 92%, 93%, 94%, 95%, 96%, 97%, 98%, 99% or greater sequence identity or complementarity to the target polynucleotide.

Methods for preparing and using probes and primers are described, for example, in *Molecular Cloning: A Laboratory Manual*, 2.sup.nd ed, vol. 1-3, ed. Sambrook et al., Cold Spring Harbor Laboratory Press, Cold Spring Harbor, N.Y. 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990.

PCR primer pairs can be derived from a known sequence, for example, by using computer programs intended for that purpose such as the PCR primer analysis tool in Vector NTI version 10 (Invitrogen); PrimerSelect (DNASTAR Inc., Madison, Wis.); and Primer (Version 0.5.COPYRGT., 1991, Whitehead Institute for Biomedical Research, Cambridge, Mass.). Additionally, the sequence can be visually scanned and primers manually identified using guidelines known to one of skill in the art.

EXPERIMENTAL

Example 1

Obtaining GLYAT Amino Acid Sequence Diversity

Family shuffling of a variant with high catalytic activity toward glyphosate (SEQ ID NO:1) and one with low activity toward aspartate (SEQ ID NO:2) was initially performed to obtain a library of variants where those properties were combined in improved proportions in at least a few of the individual members. Those variants selected as hits became the parental genes for the next library, and so on. Other methods for introducing amino acid diversity were also employed such as site specific mutagenesis. In one method, sequences related to GLYAT that were available in public databases were aligned, and statistical algorithms were used to prioritize the diversity available at each position. The selected diversity was then randomly toggled into the most advanced sequence available with the technique of semi-synthetic shuffling (Ness et al, *Nature Biotech* 20:1251, 2002). SEQ ID NOs 3-26 were thus derived.

In another method, saturation mutagenesis was performed at each position by the technique of 'NNK coding'. NNK is a reduced genetic code of 32 codons where N represents a 25% mix each of ATGC and K represents a 50% mix each of T and G. By this method, each of the 20 amino acids was encoded and 2 of 3 stop codons eliminated. The individual substitutions were combined in recombinant libraries using synthetic or semisynthetic methods. SEQ ID NOs 27-172 were thus derived.

Example 2

Screen for Variants with Increased Specificity Based on Enzyme Activity Assays

This screen was designed to identify variants with greater specificity for glyphosate relative to other specific substrates and was based on activity measurements with crude lysates and with purified proteins. Plasmids containing glyat genes were initially transformed into Top 10 *E. coli* cells (Invitrogen) for plasmid propagation. The plasmids were then isolated and transformed into BL21(DE3) cells (Invitrogen) for screening and protein production. Transformed cells were plated onto M9 agar containing 1 to 10 mM glyphosate, where only those cells expressing a functional GLYAT enzyme were able to grow. Colonies were picked and arrayed in 96-well or 384-well format for further screening.

Activity with glyphosate and other putative substrates was initially measured with crude supernatants of lysates of *E. coli* cells expressing a GLYAT variant. Cells were grown in 96-well plates in LB medium containing the inducer, isopropyl β-D-1-thiogalactopyranoside (IPTG). Cells were spun down and lysed with BPER (Pierce). Using a 96-well liquid handling system, 15 ul of the lysate supernatant were dispensed to each of three 96-well assay plates (Greiner BioOne UV-Star). Reactions were initiated by the addition of 185 ul of reaction mixture containing 25 mM Hepes, pH 7.0, 100 mM KCl (when the substrate was glyphosate) or 20 mM KCl (when the substrate was aspartate or other substrate), 10% ethylene glycol, 167 uM acetyl CoA and the amino substrate. The rate of utilization of acetyl coenzyme A (AcCoA) supported by each substrate was measured by recording the absorbance during a two minute reaction with a Spectramax 384 Plus plate reader (Molecular Devices). If the amino acid present at position 30 (29 if alanine is absent at position 2) was cysteine, absorbance was monitored at 235 nM, which directly detects cleavage of the sulfoester bond of acetyl CoA. If the amino acid present at position 30 (29 if alanine is absent at position 2) was isoleucine, 0.5 mM 5,5'-dithiobis-(2-nitrobenzoic acid), which reacts with the coenzyme A thiol generated in the enzyme catalyzed reaction, was included in the reaction mix and absorbance was monitored at 412 nm. Three separate reactions were run with each lysate, in which the amino substrate was 3 mM glyphosate, 0.5 mM glyphosate or 20 mM aspartate. Hits were picked on the basis of highest activity with 3 mM glyphosate as an indication of $k_{cat}$, highest value for the ratio of activity at 0.5 mM glyphosate to that at 3 mM glyphosate as an indicator of $K_{M\,glyph}$, and highest values for the ratio of activity with 3 mM glyphosate to that with aspartate as an indicator of specificity.

To broaden the range of substrates against which to select for activity, substrates with differing structural and chemical properties can be combined. In this example, 20 mM threonine, which has a hydroxyethyl side chain, was combined with 20 mM aspartate, which has a carboxymethyl side chain, in the screen with crude lysates. The results in Table 2 show the improvement in specificity (in this case, reduced activity with L-serine, O-phospho-L-serine and L-threonine) obtained when threonine was included in the crude lysate activity screen.

The data from the crude lysate activity screen were used to select approximately 5 to 10% of the variants that were able to grow on minimal medium containing glyphosate as potentially having the desired kinetic properties. The final stage of screening was to obtain purified proteins and perform substrate saturation kinetic analysis.

TABLE 2

Selection of greater specificity of GLYATs using multiple substrate assay. The data are micromolar product formed in 30 minutes in reaction mixtures containing 10 mM amino substrate, 0.167 mM AcCoA and 0.1 uM enzyme.

Selected against activity with aspartate.

| | SEQ ID NO: | | | |
|---|---|---|---|---|
| | 24 | 25 | 11 | 26 |
| Serine | 7.02 | 6.76 | 9.78 | 4.82 |
| P-Serine | 6.66 | 9.15 | 2.81 | 1.62 |
| Threo | 9.66 | 10.75 | 9.70 | 4.73 |

Selected against activity with aspartate and threonine

| | SEQ ID NO: | | | | | |
|---|---|---|---|---|---|---|
| | 65 | 29 | 36 | 37 | 83 | 99 |
| Serine | 0.44 | 1.10 | 0.65 | −0.04 | 1.29 | 0.11 |
| P-Serine | 0.08 | 0.97 | 0.27 | 0.47 | 0.65 | 0.37 |
| Threo | 0.35 | 0.60 | 0.42 | −0.09 | 1.12 | 0.03 |

Example 3

Production, Purification and Kinetic Analysis of GLYAT Proteins

*E. coli* cultures in LB or 2×YT were grown overnight at 37° C. to saturation. The cells were used as a 2% inoculum into fresh media. When OD reached 0.6, IPTG was added to 0.2 mM and growth was continued for at least 6 hours. Cells were harvested by centrifugation and stored at −80° C. Cells were lysed with BPER (Pierce) containing 1 mM dithiothreitol, 0.2 mg/ml lysozyme, 2 mg/ml protease inhibitor cocktail (Sigma bacterial cell cocktail, P8465) and endonuclease. Lysate supernatants were passed through a column of NHS-activated Agarose (Thermo, #26197) derivatized with coenzyme A. Columns were washed with 25 mM Hepes, pH 7, containing progressively higher concentrations of KCl, then eluted with 25 mM Hepes, 100 mM KCl, 10% ethylene glycol and 1 mM acetyl CoA. Purity as evaluated by polyacrylamide gel electrophoresis was deemed consistently high enough to be assumed to be 100%. Protein concentration was determined with the Bradford assay using a large-scale lot of produced GLYAT protein as standard.

Kinetic parameters for various substrates were obtained using a range of seven substrate concentrations plus a blank containing none of the varied substrate. The non-varied substrate was present at a saturating concentration. Six-microliter aliquots of 50-fold concentrated stock solutions of the varied substrate were placed in a 96-well assay plate (Greiner BioOne UV-Star). Reactions were started with the addition of 294 ul of 25 mM Hepes, pH 7.0, 100 mM KCL, 10% ethylene glycol, the non-varied substrate and 10 to 200 nM enzyme. Absorbance was monitored for one minute with a Spectramax 384 Plus plate reader (Molecular Devices). If the amino acid present at position 30 (29 if alanine is absent at position 2) was cysteine, absorbance was monitored at 235 nM, which directly detects cleavage of the sulfoester bond of acetyl CoA. If the amino acid present at position 30 (29 if alanine is absent at position 2) was isoleucine, 0.5 mM 5,5'-dithiobis-(2-nitrobenzoic acid), which reacts with the coenzyme A thiol generated in the enzyme catalyzed reaction, was included in the reaction mix and absorbance was monitored at 412 nm. Initial rates were processed by the Softmax software to obtain kinetic parameters, using the double-reciprocal transformation.

Kinetic parameters of GLYAT variants identified by the procedures described in Examples 1-2 are shown in Table 3. $k_{cat}/K_M$ with aspartate was reduced from 13.7 min$^{-1}$ mM$^{-1}$ in SEQ ID NO:1 to as low as 0.1 in novel variants, while specificity ($k_{cat}/K_M$ asp/$k_{cat}/K_{M\,glyph}$) improved from 1.3% to as low as 0.014%.

TABLE 3

Kinetic analysis of high specificity glyphosate acetyltransferase enzymes derived from SEQ ID NO: 1 and 2.

| | Kinetic parameters, glyphosate | | | Kinetic parameters, aspartate | | | Asp as |
|---|---|---|---|---|---|---|---|
| SEQ ID NO: | $k_{cat}$, min$^{-1}$ | $K_M$, mM | $k_{cat}/K_M$ | $k_{cat}$, min$^{-1}$ | $K_M$, mM | $k_{cat}/K_M$ | % of glyph |
| 1 | 1454 | 1.36 | 1080 | 438 | 32.9 | 13.74 | 1.273 |
| 2 | 271 | 1.38 | 196 | 53.2 | 47.6 | 1.12 | 0.574 |
| 3 | 696 | 0.60 | 1159 | 163 | 35.1 | 4.67 | 0.403 |
| 4 | 1613 | 1.96 | 827 | 136 | 78.3 | 1.74 | 0.210 |
| 5 | 1019 | 0.23 | 4588 | 215 | 79.1 | 2.72 | 0.059 |
| 6 | 673 | 2.24 | 308 | 11 | 66.8 | 0.16 | 0.052 |

TABLE 3-continued

Kinetic analysis of high specificity glyphosate acetyltransferase enzymes derived from SEQ ID NO: 1 and 2.

| SEQ ID NO: | Kinetic parameters, glyphosate | | | Kinetic parameters, aspartate | | | Asp as % of glyph |
|---|---|---|---|---|---|---|---|
| | $k_{cat}$, min$^{-1}$ | $K_M$, mM | $k_{cat}/K_M$ | $k_{cat}$, min$^{-1}$ | $K_M$, mM | $k_{cat}/K_M$ | |
| 7 | 428 | 0.80 | 532 | 91 | 112 | 0.82 | 0.154 |
| 8 | 687 | 0.39 | 1779 | 85 | 60.0 | 1.41 | 0.079 |
| 9 | 694 | 0.25 | 2726 | 155 | 78.7 | 2.00 | 0.073 |
| 10 | 699 | 0.37 | 1901 | 149 | 89.3 | 1.69 | 0.091 |
| 11 | 734 | 0.44 | 1684 | 138 | 95.9 | 1.45 | 0.086 |
| 12 | 425 | 0.28 | 1560 | 82 | 53.9 | 1.51 | 0.097 |
| 13 | 516 | 0.51 | 1092 | 87 | 82.1 | 1.09 | 0.100 |
| 14 | 945 | 0.37 | 2580 | 189 | 69.2 | 2.78 | 0.108 |
| 15 | 435 | 0.32 | 1391 | 103 | 72.3 | 1.43 | 0.103 |
| 16 | 393 | 0.69 | 574 | 56 | 65.2 | 0.90 | 0.157 |
| 17 | 530 | 0.83 | 639 | 95 | 89.7 | 1.06 | 0.165 |
| 18 | 1217 | 0.73 | 1714 | 157 | 53.0 | 2.96 | 0.173 |
| 19 | 1016 | 0.80 | 1272 | 148 | 65.1 | 2.27 | 0.178 |
| 20 | 946 | 0.64 | 1485 | 165 | 52.9 | 3.11 | 0.209 |
| 21 | 2411 | 2.59 | 930 | 151 | 72.4 | 2.08 | 0.223 |
| 22 | 2527 | 5.24 | 485 | 123 | 104 | 1.20 | 0.247 |
| 23 | 427 | 0.70 | 613 | 83.0 | 80.6 | 1.03 | 0.168 |
| 24 | 708 | 1.31 | 540 | 65.2 | 62.6 | 1.04 | 0.193 |
| 25 | 678 | 0.83 | 832 | 67.1 | 112.2 | 0.60 | 0.072 |
| 26 | 560 | 0.22 | 2505 | 90 | 104 | 0.96 | 0.038 |
| 27 | 563 | 0.46 | 1225 | 72.6 | 125.7 | 0.58 | 0.047 |
| 28 | 520 | 0.54 | 959 | 34.5 | 164.2 | 0.21 | 0.022 |
| 29 | 1000 | 0.28 | 3831 | 56.8 | 116.7 | 0.48 | 0.014 |
| 30 | 255 | 0.23 | 1089 | 17.9 | 84.5 | 0.21 | 0.019 |
| 31 | 530 | 0.59 | 904 | 15 | 72.9 | 0.21 | 0.023 |
| 32 | 782 | 0.45 | 1756 | 46 | 103.3 | 0.44 | 0.025 |
| 33 | 1222 | 0.46 | 2674 | 78 | 97.6 | 0.80 | 0.030 |
| 34 | 990 | 0.68 | 1458 | 36 | 105.1 | 0.34 | 0.024 |
| 35 | 544 | 0.60 | 904 | 18 | 84.4 | 0.21 | 0.023 |
| 36 | 719 | 0.49 | 1480 | 38 | 146.4 | 0.26 | 0.018 |
| 37 | 619 | 0.68 | 908 | 17 | 88.8 | 0.19 | 0.021 |
| 38 | 388 | 0.58 | 665 | 10 | 109.2 | 0.09 | 0.014 |
| 39 | 637 | 0.49 | 1289 | 31 | 105.0 | 0.30 | 0.023 |
| 40 | 443 | 0.17 | 2686 | 55 | 101.7 | 0.54 | 0.020 |
| 41 | 356 | 0.438 | 812 | 18.7 | 92.9 | 0.202 | 0.025 |
| 42 | 290 | 0.374 | 776 | 16.6 | 81.4 | 0.204 | 0.026 |
| 43 | 702 | 0.883 | 795 | 26.8 | 100.0 | 0.268 | 0.034 |
| 44 | 671 | 0.741 | 906 | 40.2 | 113.7 | 0.353 | 0.039 |
| 45 | 546 | 0.588 | 928 | 26.9 | 132.1 | 0.204 | 0.022 |
| 46 | 654 | 0.952 | 687 | 25.3 | 155.1 | 0.163 | 0.024 |
| 47 | 643 | 0.727 | 885 | 22.4 | 126.7 | 0.177 | 0.020 |
| 48 | 962 | 1.600 | 601 | 24.1 | 141.5 | 0.170 | 0.028 |
| 49 | 566 | 0.890 | 636 | 22.6 | 97.6 | 0.232 | 0.036 |
| 50 | 461 | 0.405 | 1142 | 39.5 | 100.5 | 0.424 | 0.038 |
| 51 | 360 | 0.580 | 620 | 17.3 | 95.2 | 0.182 | 0.029 |
| 52 | 709 | 0.664 | 1067 | 40 | 129.9 | 0.309 | 0.029 |
| 53 | 867 | 0.912 | 951 | 33 | 135.0 | 0.242 | 0.025 |
| 54 | 481 | 1.292 | 373 | 10 | 98.5 | 0.104 | 0.028 |
| 55 | 895 | 0.890 | 1006 | 34 | 102.6 | 0.330 | 0.033 |
| 56 | 763 | 0.629 | 1213 | 46 | 129.5 | 0.355 | 0.029 |
| 57 | 1131 | 0.932 | 1214 | 47.2 | 152.1 | 0.311 | 0.026 |
| 58 | 654 | 0.569 | 1138 | 55.1 | 143.8 | 0.388 | 0.034 |
| 59 | 737 | 0.833 | 885 | 25.7 | 96.0 | 0.268 | 0.030 |
| 60 | 2735 | 0.593 | 4613 | 168.5 | 100.3 | 1.680 | 0.036 |
| 61 | 962 | 1.147 | 838 | 30.7 | 127.3 | 0.241 | 0.029 |
| 62 | 934 | 0.930 | 1004 | 28.5 | 107.3 | 0.266 | 0.026 |
| 63 | 1418 | 1.024 | 1385 | 51.8 | 152.4 | 0.340 | 0.025 |
| 64 | 793 | 0.747 | 1062 | 46.2 | 113.0 | 0.409 | 0.039 |
| 65 | 1093 | 0.971 | 1125 | 161.7 | 1237 | 0.131 | 0.012 |
| 66 | 718 | 0.443 | 1620 | 51 | 108.4 | 0.47 | 0.029 |
| 67 | 702 | 0.750 | 936 | 36 | 104.4 | 0.34 | 0.037 |
| 68 | 1095 | 1.026 | 1067 | 49 | 230.6 | 0.21 | 0.020 |
| 69 | 986 | 0.611 | 1614 | 43 | 115.6 | 0.37 | 0.023 |
| 70 | 985 | 0.974 | 1012 | 33 | 90.3 | 0.37 | 0.036 |
| 71 | 685 | 1.217 | 563 | 15 | 72.2 | 0.21 | 0.038 |
| 72 | 465 | 0.751 | 619 | 20 | 128.3 | 0.16 | 0.025 |
| 73 | 519 | 0.790 | 657 | 24 | 102.5 | 0.24 | 0.036 |
| 74 | 715 | 0.797 | 897 | 40 | 157.5 | 0.25 | 0.028 |
| 75 | 464 | 0.636 | 730 | 17 | 99.1 | 0.17 | 0.023 |
| 76 | 487 | 0.778 | 626 | 22 | 135.1 | 0.16 | 0.026 |
| 77 | 513 | 0.703 | 729 | 20 | 127 | 0.16 | 0.022 |
| 78 | 560 | 0.598 | 937 | 32 | 105 | 0.31 | 0.033 |
| 79 | 424 | 0.473 | 896 | 32 | 112 | 0.28 | 0.032 |
| 80 | 481 | 0.783 | 614 | 13 | 91 | 0.14 | 0.023 |
| 81 | 459 | 0.550 | 834 | 25 | 110 | 0.23 | 0.027 |
| 82 | 359 | 0.465 | 772 | 19 | 100 | 0.19 | 0.025 |
| 83 | 511 | 0.417 | 1227 | 40 | 111 | 0.36 | 0.030 |
| 84 | 300 | 0.28 | 1079 | 18.1 | 67.2 | 0.27 | 0.025 |
| 85 | 446 | 0.564 | 792 | 18 | 97 | 0.18 | 0.023 |
| 86 | 472 | 0.519 | 909 | 12 | 86 | 0.14 | 0.015 |
| 87 | 555 | 0.604 | 919 | 44 | 112 | 0.39 | 0.042 |
| 88 | 351 | 0.434 | 808 | 28 | 82 | 0.34 | 0.042 |
| 89 | 531 | 1.031 | 515 | 15 | 83 | 0.18 | 0.035 |
| 90 | 490 | 0.872 | 562 | 12 | 82 | 0.15 | 0.027 |
| 91 | 436 | 0.831 | 525 | 13 | 82 | 0.16 | 0.031 |
| 92 | 406 | 0.479 | 847 | 32 | 108 | 0.30 | 0.035 |
| 93 | 500 | 0.661 | 757 | 31 | 105 | 0.29 | 0.039 |
| 94 | 419 | 0.583 | 719 | 22 | 76 | 0.28 | 0.040 |
| 95 | 519 | 0.609 | 853 | 33 | 112 | 0.29 | 0.034 |
| 96 | 384 | 0.642 | 598 | 24 | 101 | 0.24 | 0.040 |
| 97 | 531 | 0.461 | 1151 | 36 | 94 | 0.38 | 0.033 |
| 98 | 523 | 0.845 | 618 | 19 | 96 | 0.19 | 0.031 |
| 99 | 684 | 0.692 | 988 | 34 | 107 | 0.32 | 0.032 |
| 100 | 313 | 0.465 | 673 | 12 | 58 | 0.21 | 0.031 |
| 101 | 447 | 0.621 | 719 | 14 | 112 | 0.13 | 0.018 |
| 102 | 481 | 0.205 | 2346 | 78.5 | 94.9 | 0.83 | 0.035 |
| 103 | 543 | 0.191 | 2844 | 95.3 | 102.5 | 0.93 | 0.033 |
| 104 | 505 | 0.211 | 2391 | 89.9 | 103.0 | 0.87 | 0.036 |
| 105 | 797 | 0.438 | 1820 | 65.6 | 98.7 | 0.66 | 0.037 |
| 106 | 534 | 0.323 | 1654 | 82.5 | 108.1 | 0.76 | 0.046 |
| 107 | 536 | 0.313 | 1714 | 77.9 | 114.8 | 0.68 | 0.040 |
| 108 | 513 | 0.305 | 1682 | 87.3 | 106.8 | 0.82 | 0.049 |
| 109 | 475 | 0.28 | 1696 | 82.8 | 117.4 | 0.71 | 0.042 |
| 110 | 513 | 0.329 | 1560 | 82.0 | 99.5 | 0.82 | 0.053 |
| 111 | 537 | 0.221 | 2428 | 76.0 | 95.8 | 0.79 | 0.033 |
| 112 | 517 | 0.23 | 2249 | 78.0 | 97.9 | 0.80 | 0.035 |
| 113 | 594 | 0.245 | 2422 | 94.1 | 109.8 | 0.86 | 0.035 |
| 114 | 599 | 0.225 | 2668 | 90.5 | 103.3 | 0.88 | 0.033 |
| 115 | 529 | 0.220 | 2402 | 73.9 | 86.0 | 0.86 | 0.036 |
| 116 | 559 | 0.779 | 718 | 72.1 | 93.7 | 0.77 | 0.107 |
| 117 | 630 | 0.536 | 1176 | 73.2 | 94.7 | 0.77 | 0.066 |
| 118 | 710 | 0.299 | 2373 | 110.9 | 62.3 | 1.78 | 0.075 |
| 119 | 574 | 0.393 | 1461 | 86.2 | 111.8 | 0.77 | 0.053 |
| 120 | 382 | 0.331 | 1154 | 60.4 | 115.6 | 0.52 | 0.045 |
| 121 | 544 | 0.161 | 3431 | 95 | 122 | 0.78 | 0.024 |
| 122 | 523 | 0.311 | 1681 | 91.2 | 121.7 | 0.75 | 0.045 |
| 123 | 454 | 0.226 | 2009 | 64.4 | 109.6 | 0.59 | 0.029 |
| 124 | 461 | 0.409 | 1128 | 59.4 | 120.4 | 0.49 | 0.044 |
| 125 | 454 | 0.216 | 2102 | 81.6 | 128.0 | 0.64 | 0.030 |
| 126 | 475 | 0.206 | 2306 | 75.8 | 96.6 | 0.78 | 0.034 |
| 127 | 562 | 0.202 | 2784 | 94.1 | 96.2 | 0.98 | 0.035 |
| 128 | 536 | 0.198 | 2706 | 89.4 | 88.9 | 1.01 | 0.037 |
| 129 | 346 | 0.313 | 1106 | 60.3 | 103.7 | 0.58 | 0.053 |
| 130 | 642 | 0.284 | 2261 | 138.1 | 172.0 | 0.80 | 0.036 |
| 131 | 754 | 0.434 | 1737 | 77.9 | 137.0 | 0.57 | 0.033 |
| 132 | 474 | 0.314 | 1510 | 46.1 | 92.9 | 0.50 | 0.033 |
| 133 | 620 | 0.354 | 1751 | 64.8 | 103.0 | 0.63 | 0.036 |
| 134 | 911 | 0.376 | 2423 | 74.5 | 100.2 | 0.74 | 0.031 |
| 135 | 703 | 0.382 | 1841 | 49.5 | 90.1 | 0.55 | 0.030 |
| 136 | 1034 | 0.503 | 2055 | 54.6 | 78.0 | 0.70 | 0.034 |
| 137 | 547 | 0.297 | 1841 | 60.3 | 96.6 | 0.62 | 0.034 |
| 138 | 312 | 0.286 | 1090 | 45.4 | 101.2 | 0.45 | 0.041 |
| 139 | 624 | 0.681 | 916 | 38.9 | 104.4 | 0.37 | 0.041 |
| 140 | 508 | 0.204 | 2491 | 99.9 | 105.5 | 0.95 | 0.038 |
| 141 | 473 | 0.348 | 1360 | 60.7 | 114.1 | 0.53 | 0.039 |
| 142 | 402 | 0.347 | 1158 | 61.8 | 122.4 | 0.50 | 0.044 |
| 143 | 501 | 0.309 | 1621 | 83.2 | 119.9 | 0.69 | 0.043 |
| 144 | 485 | 0.223 | 2335 | 80.4 | 125.4 | 0.64 | 0.030 |
| 145 | 517 | 0.303 | 1706 | 75.4 | 104.8 | 0.72 | 0.042 |
| 146 | 570 | 0.396 | 1440 | 60.3 | 80.3 | 0.75 | 0.052 |
| 147 | 563 | 0.46 | 1225 | 72.6 | 125.7 | 0.58 | 0.047 |
| 148 | 609 | 0.436 | 1396 | 68.7 | 91.6 | 0.75 | 0.054 |

TABLE 3-continued

Kinetic analysis of high specificity glyphosate acetyltransferase enzymes derived from SEQ ID NO: 1 and 2.

| SEQ ID NO: | Kinetic parameters, glyphosate | | | Kinetic parameters, aspartate | | | Asp as % of glyph |
|---|---|---|---|---|---|---|---|
| | $k_{cat}$ min$^{-1}$ | $K_M$, mM | $k_{cat}/K_M$ | $k_{cat}$ min$^{-1}$ | $K_M$, mM | $k_{cat}/K_M$ | |
| 149 | 855 | 0.293 | 2919 | 121.6 | 83.7 | 1.45 | 0.050 |
| 150 | 562 | 0.331 | 1696 | 69.6 | 93.7 | 0.74 | 0.044 |
| 151 | 612 | 0.301 | 2026 | 80.6 | 95.5 | 0.85 | 0.042 |
| 152 | 600 | 0.406 | 1477 | 65 | 116 | 0.56 | 0.038 |
| 153 | 750 | 0.461 | 1628 | 75.7 | 108.0 | 0.70 | 0.043 |
| 154 | 485 | 0.350 | 1377 | 61.4 | 136 | 0.45 | 0.033 |
| 155 | 709 | 0.294 | 2410 | 121.6 | 94.8 | 1.28 | 0.053 |
| 156 | 867 | 0.327 | 2650 | 155.2 | 105.7 | 1.47 | 0.055 |
| 157 | 602 | 0.329 | 1829 | 92.1 | 89.1 | 1.03 | 0.056 |
| 158 | 556 | 0.376 | 1480 | 78.5 | 88.0 | 0.89 | 0.060 |
| 159 | 521 | 0.344 | 1513 | 81.8 | 106.3 | 0.77 | 0.051 |
| 160 | 497 | 0.342 | 1454 | 72.2 | 89.5 | 0.81 | 0.056 |
| 161 | 676 | 0.362 | 1869 | 104.0 | 99.7 | 1.04 | 0.056 |
| 162 | 532 | 0.528 | 1008 | 72.2 | 77.3 | 0.93 | 0.093 |
| 163 | 775 | 0.415 | 1867 | 92.6 | 80.3 | 1.15 | 0.062 |
| 164 | 678 | 0.731 | 928 | 123.0 | 93.2 | 1.32 | 0.142 |
| 165 | 4726 | 2.228 | 2121 | 234.8 | 83.0 | 2.83 | 0.133 |
| 166 | 668 | 0.478 | 1404 | 232 | 159 | 1.46 | 0.104 |
| 167 | 511 | 0.462 | 1107 | 93.6 | 112.3 | 0.83 | 0.075 |
| 168 | 724 | 0.497 | 1456 | 126.5 | 118.1 | 1.07 | 0.074 |
| 169 | 685 | 0.693 | 988 | 174.3 | 93.0 | 1.87 | 0.190 |
| 170 | 410 | 0.376 | 1091 | 51.4 | 86.0 | 0.60 | 0.055 |
| 171 | 644 | 0.409 | 1573 | 73.1 | 108.5 | 0.67 | 0.043 |
| 172 | 404 | 0.376 | 1074 | 42.6 | 89.7 | 0.47 | 0.044 |

Example 4

Novel Amino Acid Diversity

Amino acid substitutions unique to the high specificity GLYAT proteins are shown in Table 4. The sequences with the new substitutions were derived through a combination of saturation mutagenesis of an already fit protein (SEQ ID NO:26) and an effective screening cascade as a means of identifying the improved genes (Examples 1-2). Regions in which novel changes are concentrated include helix H2a (positions 23 and 25-29) and the hairpin formed by strands B6 and B7 (positions 124-144). These two structures are components of the amino substrate binding site. Helix H3, the backbone to which the central beta sheet is anchored, is a region where 24% of the novel substitutions (17 out of 71) disclosed in Table 4 are concentrated into 11% of the positions (16 out of 146). None of those are near enough to the active site to influence substrate specificity directly. In three cases, multiple novel substitutions were discovered immediately or nearly adjacent to conserved amino acids shown previously to contribute to the catalytic mechanism (Siehl D L et. al., *J Biol Chem*, 282:11446, 2007). The catalytic amino acids for which this is the case are R21, R111, H138 and the nearby positions with multiple substitutions are 23, 112 and 137. The diverse amino acids at these positions may influence the orientation of the neighboring catalytic amino acids so as to selectively optimize catalysis with the preferred substrate, glyphosate.

Figure 2:
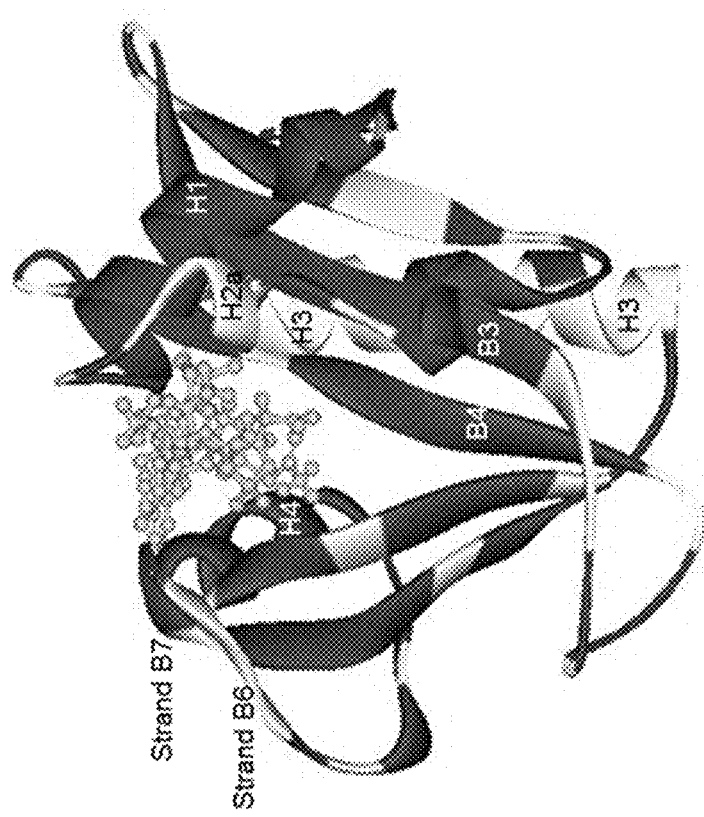
FIG. 2 shows the structure of glyphosate acetyltransferase. Light color on ribbon model indicates where substitutions occur in high specificity variants. Stick model of AcetylCoA and substrate are shown in the active site cleft. Helices (H) and beta strands (B) mentioned in the text are labeled.

Helix H1 (positions 9-19), strand B3 (positions 50-58) and helix H4 (positions 113-120) are regions where screening for substrate specificity resulted in the elimination of most of the diversity discovered earlier, with most amino acids reverting to those present in native GLYAT. See FIG. 2 for structural details.

In comparing the amino acid sequences of native GLYAT (SEQ ID NO:173), SEQ ID NO:1 and one of the highest specificity variants (SEQ ID NO:29), a motif is revealed as shown in Table 5; this motif is represented by SEQ ID NO:174. In reducing activity with aspartate from 13.7 min$^{-1}$ mM$^{-1}$ with SEQ ID NO:1 to 0.48 with SEQ ID NO:29, five amino acids in helix H2a-H2b are changed to ones with larger, mostly aliphatic side chains. Most significantly, C291 and F31Y fill a spatial vacancy that molecular models suggest could be occupied by the amino group of L-amino acids and other branched compounds, thus improving specificity for the linear glyphosate molecule. The other up-sizing mutations may function to restrict access of water molecules into the active site, which may increase specificity by disallowing formation of water wires between unwanted substrates and the catalytic base, H138. Additionally, according to the Columbus equation (the attractive force of opposite charges is inversely related to the dielectric constant of the medium), increased hydrophobicity in the active site would strengthen the charge interactions between glyphosate and the side chains that ligate it (R21, R73, R111 and H138). Thus, in some embodiments, the motif VIMY-ETDLL (SEQ ID NO:174) is a determinant for highest-specificity GLYAT proteins. SEQ ID NOs:26-115 and 119-172 contain the motif (SEQ ID NO:174).

TABLE 4

New sequence diversity generated in high specificity GLYAT variants.
Numbering is based on SEQ ID NO: 2.

| Position | New Substitution |
|---|---|
| 1 | |
| 2 | |
| 3 | SC |
| 4 | |
| 5 | |
| 6 | M |
| 7 | |
| 8 | G |
| 9 | |
| 10 | |
| 11 | |
| 12 | |
| 13 | |
| 14 | |
| 15 | |

TABLE 4-continued

New sequence diversity generated in high specificity GLYAT variants.
Numbering is based on SEQ ID NO: 2.

| Position | New Substitution |
|---|---|
| 16 | |
| 17 | |
| 18 | |
| 19 | |
| 20 | |
| 21 | |
| 22 | |
| 23 | GRK |
| 24 | |
| 25 | S |
| 26 | F |
| 27 | SR |
| 28 | RK |
| 29 | I |
| 30 | |
| 31 | W |
| 32 | |
| 33 | |
| 34 | |
| 35 | |
| 36 | |
| 37 | |
| 38 | |
| 39 | C |
| 40 | |
| 41 | S |
| 42 | H |
| 43 | |
| 44 | |
| 45 | |
| 46 | C |
| 47 | |
| 48 | A |
| 49 | |
| 50 | |
| 51 | |
| 52 | |
| 53 | |
| 54 | |
| 55 | |
| 56 | |
| 57 | |
| 58 | G |
| 59 | C |
| 60 | L |
| 61 | |
| 62 | |
| 63 | SR |
| 64 | |
| 65 | |
| 66 | |
| 67 | C |
| 68 | V |
| 69 | |
| 70 | |
| 71 | |
| 72 | |
| 73 | |
| 74 | |
| 75 | A |
| 76 | |
| 77 | |
| 78 | |
| 79 | G |
| 80 | |
| 81 | |
| 82 | |
| 83 | N |
| 84 | |
| 85 | R |
| 86 | |
| 87 | A |
| 88 | R |

TABLE 4-continued

New sequence diversity generated in high specificity GLYAT variants.
Numbering is based on SEQ ID NO: 2.

| Position | New Substitution |
|----------|------------------|
| 89  | RN |
| 90  | V |
| 91  | M |
| 92  |  |
| 93  |  |
| 94  |  |
| 95  | Q |
| 96  | D |
| 97  |  |
| 98  | M |
| 99  | VAK |
| 100 | A |
| 101 | ACLI |
| 102 |  |
| 103 |  |
| 104 |  |
| 105 | T |
| 106 |  |
| 107 |  |
| 108 |  |
| 109 | FQ |
| 110 |  |
| 111 |  |
| 112 | VLM |
| 113 |  |
| 114 |  |
| 115 |  |
| 116 |  |
| 117 |  |
| 118 |  |
| 119 |  |
| 120 |  |
| 121 |  |
| 122 |  |
| 123 |  |
| 124 |  |
| 125 | S |
| 126 |  |
| 127 |  |
| 128 | GTARC |
| 129 |  |
| 130 | W |
| 131 | QR |
| 132 | Y |
| 133 | K |
| 134 |  |
| 135 |  |
| 136 |  |
| 137 | EARS |
| 138 |  |
| 139 |  |
| 140 |  |
| 141 |  |
| 142 | VC |
| 143 |  |
| 144 |  |
| 145 |  |
| 146 |  |

TABLE 5

Generation of a motif for high activity and specificity in GLYAT enzymes.

| Variant | 28 | 29 | 30 | 31 | 32 | 33 | 34 | 35 | 36 | kcat/Km glyph | asp | asp, % glyph |
|---|---|---|---|---|---|---|---|---|---|---|---|---|
| SEQ ID NO: 173 | A | C | M | Y | E | T | D | L | L | 0.27 | 0.15 | 55.6 |
| SEQ ID NO: 29 | V | I | M | Y | E | T | D | L | L | 3830 | 0.48 | 0.013 |
| SEQ ID NO: 1 | A | C | M | F | E | S | D | L | T | 1080 | 13.7 | 1.27 |

Example 5

Efficacy of High Specificity Glyat Genes in Multiple Crops

Glyphosate acetyltransferase (glyat) genes selected for high specificity to glyphosate were introduced into multiple plant species and evaluated for both efficacy and phenotype in the greenhouse and field. *Agrobacterium*-mediated transformation of maize was performed using well-known transformation procedures. All T0 plants are transplanted to soil and grown in a greenhouse under standard conditions. T0 plants are typically sprayed about 2 weeks after transplanting with 1680 g ae/ha (2×) commercial glyphosate formulation such as Touchdown™ or RoundUp WeatherMax™. T1 plants are often evaluated after a 3360 g ae/ha (4×) glyphosate application. Rates of glyphosate for canola were 1350 g ae/ha (2×) for both T0 and T1. Field rates ranged from 0× to 8× glyphosate treatment at stages from V3 to reproductive stage. All applications typically included ammonium sulfate. As listed in Table 6, transformed events in all crops showed excellent efficacy with the glyat genes when expressed with Ubiquitin promoters for moderate constitutive expression in all tissues. No deviations in phenotype from untransformed plants were observed in advanced events.

TABLE 6

High specificity glyphosate acetyltransferase genes confer robust glyphosate tolerance in multiple crop species.

| glyat Gene | Crop | % T0 events with low/no herbicide response (2X rate) | % T1 events with low/no herbicide response (4X rate) | Tested Field efficacy with <10% herbicide response |
|---|---|---|---|---|
| SEQ ID NO: 3 | Maize | 86% | ND | 4X glyphosate at V4 |
| SEQ ID NO: 19 | Maize | 86% | 100% | ND |
| SEQ ID NO: 11 | Maize | 70% | 99% | 4X glyphosate at V4 |
| SEQ ID NO: 26 | Maize | 52% | 100% | ND |
| SEQ ID NO: 25 | Maize | 64% | ND | ND |
| SEQ ID NO: 132 | Maize | 54% | ND | ND |
| SEQ ID NO: 134 | Maize | 58% | ND | ND |
| SEQ ID NO: 3 | Soy | 65% | 34% | 4X glyphosate at V3 |
| SEQ ID NO: 4 | Soy | 50% | 13% | 4X glyphosate at V3 |
| SEQ ID NO: 19 | Soy | 75% | 54% | 4X glyphosate at V3 |
| SEQ ID NO: 11 | Soy | 69% | 46% | 4X glyphosate at V3 |
| SEQ ID NO: 9 | Soy | 89% | 30% | ND |
| SEQ ID NO: 6 | Soy | 85% | 23% | ND |
| SEQ ID NO: 26 | Soy | 100% | ND | ND |
| SEQ ID NO: 25 | Soy | 82% | ND | ND |
| SEQ ID NO: 132 | Soy | 100% | ND | ND |
| SEQ ID NO: 3 | Canola | 93% | 98% | 8X at 3-5 leaf stage |
| SEQ ID NO: 19 | Canola | 95% | 97% | ND |
| SEQ ID NO: 11 | Canola | 92% | 98% | 4X at 3-5 leaf stage |
| SEQ ID NO: 3 | Rice | 100% | 100% | 8X at V6 |
| SEQ ID NO: 11 | Rice | 100% | 100% | ND |

ND; No data to date

Example 6

Reduced Accumulation of N-Acetyl Amino Acids in Transgenic Plants Expressing High-Specificity Glyat Genes Some amino acids, primarily aspartate (Asp) and glutamate (Glu), can act as substrate for glyphosate acetyltransferase enzymes and become acetylated, resulting in in planta accumulation of N-acetyl amino acids. While accumulation of N-acetyl amino acids has not been reported to pose a safety concern (see e.g., Delaney et al. 2008. *Food Chem Toxicol* 46:2023-2034; Harper et al. 2009. *Food Chem Toxicol* 47:2723-2729), increased glyphosate acetyltransferase enzyme specificity will improve efficiency. Tissue samples from plants expressing glyat genes were prepared and analyzed for N-acetyl amino acids by the method described in Hession A O, Esrey E G, Croes R A, Maxwell C A (2008) N-Acetylglutamate and N-Acetylaspartate in Soybeans (*Glycine max* L.), Maize (*Zea maize* L.), and Other Foodstuffs. *Journal of Agricultural and Food Chemistry* 56:9121-9126. Plants expressing high-specificity GLYAT enzymes, e.g. SEQ ID NO: 11 accumulated substantially lower levels of NA-Asp than plants expressing SEQ ID NO:1 as shown in Table 7. This reduction of acetylated amino acids is an indication of the improved substrate specificity of the enzyme, and is consistent with in vitro enzyme analysis.

TABLE 7

Crop plants expressing high-specificity GLYAT enzymes accumulate reduced average levels of NA-Asp in leaf and seed tissue as compared to SEQ ID NO: 1 when both genes are driven by the same promoter combination.

| glyat Gene | Sample type | NA-Asp (ug/g) | Fold reduction | Crop |
|---|---|---|---|---|
| SEQ ID NO: 1 | Leaf (Tn) | 303 | Control | maize |
| SEQ ID NO: 11 | leaf (T0) | 13 | 23X | maize |
| SEQ ID NO: 1 | Leaf (bulk) T3 | 23,575 | Control | canola |
| SEQ ID NO: 3 | Leaf (bulk) T3 | 7,061 | 3.3X | canola |
| SEQ ID NO: 11 | Leaf (bulk) T1 | 1,954 | 12.0X | canola |
| SEQ ID NO: 1 | Seed (bulk) T3 | 2,034 | Control | canola |
| SEQ ID NO: 3 | Seed (bulk) T3 | 767 | 2.6X | canola |
| SEQ ID NO: 1 | Leaf (T0) | 879 | Control | rice |
| SEQ ID NO: 3 | Leaf (T0) | 45 | 19.5X | rice |
| SEQ ID NO: 11 | Leaf (T0) | 6 | 147X | rice |

Example 7

Glyphosate and Glufosinate Tolerance of Shuffled GLYAT Variants in Molecular Stacks with moPAT in Corn

*Maize* hybrids containing events with different GLYAT shuffled variants in a molecular stack with moPAT were planted at five midwest USA regulated transgenic research locations. The plots were sprayed with glyphosate at 3.0 lb ae/a (4×) at the V4 and V8 growth stages and with glufosinate at 0.8 lb ae/a (2×) at the V4 growth stage. Plots were evaluated for crop response at 7 and 14 days after treatment (DAT) on a 0-100 scale, where 0=no difference between treated and untreated control plots and 100=complete plant death. Data represent the crop response averaged over location, replication, and events within a construct (Table 8).

TABLE 8

Crop response to glyphosate or glufosinate averaged over location, replication, and events

| Construct | SEQ ID NO: | Dev gene | Gly 4X V4 | | Gly 4X V8 | | Glu 2X V4 | |
|---|---|---|---|---|---|---|---|---|
| | | | 7 DAT | 14 DAT | 7 DAT | 14 DAT | 7 DAT | 14 DAT |
| A | 6 | 3 | 49 | 52 | 52 | 56 | 6 | 3 |
| B | 5 | 3 | 12 | 7 | 11 | 12 | 5 | 3 |
| C | 5 | 4 | 12 | 8 | 11 | 12 | 5 | 4 |
| D | 11 | 3 | 11 | 6 | 10 | 10 | 4 | 2 |
| E | 11 | 4 | 30 | 21 | 33 | 52 | 10 | 7 |
| F | 3 | 3 | 28 | 21 | 29 | 29 | 4 | 4 |
| G | 3 | 4 | 27 | 18 | 26 | 25 | 6 | 3 |
| H | 3 | 5 | 27 | 18 | 25 | 25 | 5 | 3 |

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this disclosure pertains. All publications and patent applications are herein incorporated by reference to the same extent as if each individual publication or patent application was specifically and individually indicated to be incorporated by reference.

Although the disclosure has been described in some detail by way of illustration and example for purposes of clarity of understanding, it will be obvious that certain changes and modifications may be practiced within the scope of the appended claims.

What is claimed is:

1. A nucleic acid construct comprising an isolated or a recombinant polynucleotide comprising a nucleotide sequence encoding a polypeptide comprising an amino acid sequence having at least 95% sequence identity across the full length of SEQ ID NO: 26, wherein said polypeptide has glyphosate-N-acetyltransferase (GLYAT) activity and comprises an amino acid sequence comprising SEQ ID NO:174.

2. The nucleic acid construct of claim 1, further comprising a promoter operably linked to said polynucleotide.

3. The nucleic acid construct of claim 2, further comprising the 35S enhancer or an active variant or fragment thereof operably linked to said promoter.

4. A cell comprising the nucleic acid construct of claim 1, wherein said polynucleotide is heterologous to the cell.

5. The cell of claim 4, wherein said cell is a plant cell.

6. The plant cell of claim 5, wherein said polynucleotide or said nucleic acid construct is stably incorporated into the genome of said plant cell.

7. The plant cell of claim 5, wherein said plant cell is from a monocot.

8. The monocot plant cell of claim 7, wherein said monocot is maize, wheat, rice, barley, sugarcane, sorghum, turf grass, or rye.

9. The plant cell of claim 5, wherein said plant cell is from a dicot.

10. The dicot plant cell of claim 9, wherein the dicot is soybean, Brassica, sunflower, cotton, canola, or alfalfa.

11. A plant comprising the plant cell of claim 5.

12. An explant comprising the plant cell of claim 5.

13. The plant of claim 11, the explant of claim 12, or the plant cell of claim 5, wherein the plant, explant or plant cell further comprises at least one additional polypeptide imparting herbicide tolerance, wherein said additional polypeptide is different from GLYAT.

14. The plant, explant, or plant cell of claim 13, wherein said at least one polypeptide imparting tolerance to an additional herbicide comprises:
(a) a sulfonylurea-tolerant acetolactate synthase;
(b) an imidazolinone-tolerant acetolactate synthase;
(c) a 4-hydroxyphenylpyruvate dioxygenase;
(d) a phosphinothricin acetyl transferase;
(e) a protoporphyrinogen oxidase;
(f) a methyl transferase that provides tolerance to auxin herbicides;
(g) a P450 polypeptide;
(h) an acetyl coenzyme A carboxylase;
(i) a dicamba monooxygenase; or
(j) an aryloxyalkanoate dioxygenase.

15. The plant, explant, or plant cell of claim 13, wherein said at least one polypeptide imparting herbicide tolerance comprises an herbicide tolerant acetolactate synthase.

16. The plant, explant, or plant cell of claim 13, wherein said at least one additional polypeptide imparts tolerance to glyphosate.

17. The plant, explant or plant cell of claim 16, wherein said at least one polypeptide comprises a glyphosate-tolerant 5-enolpyruvylshikimate-3-phosphate synthase or a glyphosate-tolerant glyphosate oxido-reductase.

18. A transgenic seed produced by the plant of claim 11 wherein said transgenic seed comprises said nucleic acid construct.

19. A method of producing a glyphosate tolerant plant cell comprising, transforming a plant cell with the nucleic acid construct of claim 1.

20. The method of claim 19, wherein said method further comprises regenerating a transgenic plant from said transformed plant cell.

21. The method of claim 19, wherein said transforming the plant cell results in the stable integration of the polynucleotide into the genome of the plant cell.

22. A method for controlling weeds in a field, comprising:
(a) planting, in said field, a crop, wherein said crop comprises the transgenic seed of claim 18 or the plant of claim 11; and
(b) applying to said field a sufficient amount of glyphosate or a combination of herbicides that comprises glyphosate, to control weeds without significantly affecting the crop.

23. The plant of claim 11, the explant of claim 12, or the plant cell of claim 5, wherein the plant, explant or plant cell further comprises at least one polypeptide having pesticidal and/or insecticidal activity.

* * * * *

SEQUENCE LISTING

```
<160> NUMBER OF SEQ ID NOS: 174

<210> SEQ ID NO 1
<211> LENGTH: 147
<212> TYPE: PRT
<213> ORGANISM: Artificial Sequence
<220> FEATURE:
<223> OTHER INFORMATION: GLYAT variant

<400> SEQUENCE: 1

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Ala Cys Met Phe
                20                  25                  30

Glu Ser Asp Leu Thr Arg Ser Ala Phe His Leu Gly Gly Phe Tyr Gly
            35                  40                  45

Gly Lys Leu Ile Ser Val Ala Ser Phe His Gln Ala Glu His Ser Glu
        50                  55                  60

Leu Gln Gly Lys Lys Gln Tyr Gln Leu Arg Gly Val Ala Thr Leu Glu
65                  70                  75                  80

Gly Tyr Arg Glu Gln Lys Ala Gly Ser Ser Leu Val Lys His Ala Glu
                85                  90                  95

Glu Ile Leu Arg Lys Arg Gly Ala Asp Met Ile Trp Cys Asn Ala Arg
                100                 105                 110

Thr Ser Ala Ser Gly Tyr Tyr Arg Lys Leu Gly Phe Ser Glu Gln Gly
```

```
                    115                 120                 125
Glu Val Phe Asp Thr Pro Pro Val Gly Pro His Ile Leu Met Tyr Lys
            130                 135                 140
Arg Ile Thr
145

<210> SEQ ID NO 2
<211> LENGTH: 146
<212> TYPE: PRT
<213> ORGANISM: Artificial Sequence
<220> FEATURE:
<223> OTHER INFORMATION: GLYAT variant

<400> SEQUENCE: 2

Met Leu Glu Val Lys Pro Ile Asn Ala Glu Asp Thr Tyr Glu Leu Arg
1               5                   10                  15

His Lys Ile Leu Arg Pro Asn Gln Pro Leu Glu Val Cys Met Tyr Glu
            20                  25                  30

Thr Asp Leu Leu Arg Gly Ala Phe His Leu Gly Gly Phe Tyr Arg Gly
        35                  40                  45

Lys Leu Ile Ser Ile Ala Ser Phe His Gln Ala Glu His Ser Asp Leu
    50                  55                  60

Gln Gly Gln Lys Gln Tyr Gln Leu Arg Gly Met Ala Thr Leu Glu Gly
65                  70                  75                  80

Tyr Arg Asp Gln Lys Ala Gly Ser Ser Leu Ile Arg His Ala Glu Gln
                85                  90                  95

Ile Leu Arg Lys Arg Gly Ala Asp Met Leu Trp Cys Asn Ala Arg Thr
            100                 105                 110

Ser Ala Ser Gly Tyr Tyr Lys Lys Leu Gly Phe Ser Glu Gln Gly Glu
        115                 120                 125

Val Phe Glu Thr Pro Pro Val Gly Pro His Ile Leu Met Tyr Lys Arg
    130                 135                 140

Leu Thr
145

<210> SEQ ID NO 3
<211> LENGTH: 146
<212> TYPE: PRT
<213> ORGANISM: Artificial Sequence
<220> FEATURE:
<223> OTHER INFORMATION: GLYAT variant

<400> SEQUENCE: 3

Met Leu Glu Val Lys Pro Ile Asn Ala Glu Asp Thr Tyr Asp Leu Arg
1               5                   10                  15

His Arg Val Leu Arg Pro Asn Gln Pro Ile Glu Val Cys Met Tyr Glu
            20                  25                  30

Thr Asp Leu Leu Arg Gly Ala Phe His Leu Gly Gly Phe Tyr Gly Gly
        35                  40                  45

Lys Leu Ile Ser Val Ala Ser Phe His Gln Ala Glu His Ser Glu Leu
    50                  55                  60

Gln Gly Lys Lys Gln Tyr Gln Leu Arg Gly Val Ala Thr Leu Glu Gly
65                  70                  75                  80

Tyr Arg Asp Gln Lys Ala Gly Ser Ser Leu Val Lys His Ala Glu Glu
                85                  90                  95

Ile Leu Arg Lys Arg Gly Ala Asp Met Ile Trp Cys Asn Ala Arg Thr
            100                 105                 110
```

Ser Ala Ser Gly Tyr Tyr Lys Lys Leu Gly Phe Ser Glu Gln Gly Glu
            115                 120                 125

Val Phe Glu Thr Pro Pro Val Gly Pro His Ile Leu Met Tyr Lys Arg
130                 135                 140

Leu Thr
145

<210> SEQ ID NO 4
<211> LENGTH: 147
<212> TYPE: PRT
<213> ORGANISM: Artificial Sequence
<220> FEATURE:
<223> OTHER INFORMATION: GLYAT variant

<400> SEQUENCE: 4

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Ala Cys Met Phe
            20                  25                  30

Glu Ser Asp Leu Thr Arg Ser Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Glu Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 5
<211> LENGTH: 147
<212> TYPE: PRT
<213> ORGANISM: Artificial Sequence
<220> FEATURE:
<223> OTHER INFORMATION: GLYAT variant

<400> SEQUENCE: 5

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Cys Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Glu Gln Lys Ala Gly Ser Ser Leu Val Lys His Ala Glu
                85                  90                  95

Glu Ile Leu Arg Lys Arg Gly Ala Asp Met Ile Trp Cys Asn Ala Arg
            100                 105                 110

```
Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 6
<211> LENGTH: 147
<212> TYPE: PRT
<213> ORGANISM: Artificial Sequence
<220> FEATURE:
<223> OTHER INFORMATION: GLYAT variant

<400> SEQUENCE: 6

Met Ala Ile Glu Ile Lys Pro Ile Asn Ala Glu Asp Thr Tyr Asp Leu
1               5                   10                  15

Arg His Arg Val Leu Arg Pro Asn Gln Pro Ile Glu Val Cys Met Tyr
            20                  25                  30

Glu Thr Asp Leu Thr Arg Gly Ala Phe His Leu Gly Gly Phe Cys Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Ala Ala Thr Leu Glu
65                  70                  75                  80

Gly Tyr Arg Glu Gln Lys Ala Gly Ser Ser Leu Val Lys His Ala Glu
                85                  90                  95

Glu Ile Leu Arg Lys Arg Gly Ala Asp Met Ile Trp Cys Asn Ala Arg
            100                 105                 110

Thr Ser Ala Ser Gly Tyr Tyr Lys Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 7
<211> LENGTH: 146
<212> TYPE: PRT
<213> ORGANISM: Artificial Sequence
<220> FEATURE:
<223> OTHER INFORMATION: GLYAT variant

<400> SEQUENCE: 7

Met Leu Glu Val Lys Pro Ile Asn Ala Glu Asp Thr Tyr Asp Leu Arg
1               5                   10                  15

His Arg Val Leu Arg Pro Asn Gln Pro Ile Glu Val Cys Met Trp Glu
            20                  25                  30

Ser Asp Leu Thr Arg Ser Ala Phe His Leu Gly Gly Phe Tyr Gly Ala
        35                  40                  45

Lys Leu Ile Ser Val Ala Ser Phe His Gln Ala Glu His Ser Glu Leu
    50                  55                  60

Gln Gly Lys Lys Gln Tyr Gln Leu Arg Gly Val Ala Thr Leu Gly Gly
65                  70                  75                  80

Tyr Arg Asp Gln Lys Ala Gly Ser Ser Leu Val Lys His Ala Glu Glu
                85                  90                  95

Ile Leu Arg Lys Arg Gly Ala Asp Met Ile Trp Cys Phe Ala Arg Thr
```

```
            100                 105                 110
Ser Ala Ser Gly Tyr Tyr Lys Lys Leu Gly Phe Ser Glu Gln Gly Glu
        115                 120                 125

Val Phe Glu Leu Pro Pro Ala Gly Pro His Ile Leu Met Tyr Lys Arg
    130                 135                 140

Leu Thr
145

<210> SEQ ID NO 8
<211> LENGTH: 147
<212> TYPE: PRT
<213> ORGANISM: Artificial Sequence
<220> FEATURE:
<223> OTHER INFORMATION: GLYAT variant

<400> SEQUENCE: 8

Met Ala Ile Glu Val Lys Pro Ile Ser Ala Glu Asp Thr Tyr Asp Leu
1               5                   10                  15

Arg His Arg Ile Leu Arg Pro Asn Gln Pro Ile Glu Val Cys Met Tyr
            20                  25                  30

Glu Thr Asp Leu Thr Arg Ser Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Ile Trp Cys Asn Ala Arg
            100                 105                 110

Thr Ser Ala Ser Gly Tyr Tyr Lys Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 9
<211> LENGTH: 147
<212> TYPE: PRT
<213> ORGANISM: Artificial Sequence
<220> FEATURE:
<223> OTHER INFORMATION: GLYAT variant

<400> SEQUENCE: 9

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Cys Met Tyr
            20                  25                  30

Glu Thr Asp Leu Leu Arg Ser Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Glu Gln Lys Ala Gly Ser Ser Leu Val Lys His Ala Glu
                85                  90                  95
```

```
Glu Ile Leu Arg Lys Arg Gly Ala Asp Met Leu Trp Cys Asn Ala Arg
                100                 105                 110

Thr Ser Ala Ser Gly Tyr Tyr Lys Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145

<210> SEQ ID NO 10
<211> LENGTH: 147
<212> TYPE: PRT
<213> ORGANISM: Artificial Sequence
<220> FEATURE:
<223> OTHER INFORMATION: GLYAT variant

<400> SEQUENCE: 10

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Cys Met Tyr
            20                  25                  30

Glu Thr Asp Leu Leu Arg Ser Ala Phe His Leu Gly Gly Phe Tyr Gly
        35                  40                  45

Gly Lys Leu Ile Ser Val Ala Ser Phe His Gln Ala Glu Arg Ser Glu
    50                  55                  60

Leu Gln Gly Lys Lys Gln Tyr Gln Leu Arg Gly Val Ala Thr Leu Glu
65                  70                  75                  80

Gly Tyr Arg Glu Gln Lys Ala Gly Ser Ser Leu Val Lys His Ala Glu
                85                  90                  95

Glu Ile Leu Arg Lys Arg Gly Ala Asp Met Ile Trp Cys Asn Ala Arg
                100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145

<210> SEQ ID NO 11
<211> LENGTH: 147
<212> TYPE: PRT
<213> ORGANISM: Artificial Sequence
<220> FEATURE:
<223> OTHER INFORMATION: GLYAT variant

<400> SEQUENCE: 11

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Cys Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95
```

```
Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
130                 135                 140

Arg Leu Thr
145

<210> SEQ ID NO 12
<211> LENGTH: 146
<212> TYPE: PRT
<213> ORGANISM: Artificial Sequence
<220> FEATURE:
<223> OTHER INFORMATION: GLYAT variant

<400> SEQUENCE: 12

Met Leu Glu Val Lys Pro Ile Asn Ala Glu Asp Thr Tyr Asp Leu Arg
1               5                   10                  15

His Arg Val Leu Arg Pro Asn Gln Pro Ile Glu Val Cys Met Tyr Glu
            20                  25                  30

Thr Asp Leu Leu Arg Gly Ala Phe His Leu Gly Gly Phe Tyr Gly Gly
        35                  40                  45

Lys Leu Ile Ser Val Ala Ser Phe His Gln Ala Glu His Pro Glu Leu
50                  55                  60

Gln Gly Lys Lys Gln Tyr Gln Leu Arg Gly Val Ala Thr Leu Glu Gly
65                  70                  75                  80

Tyr Arg Asp Gln Lys Ala Gly Ser Ser Leu Val Lys His Ala Glu Glu
                85                  90                  95

Ile Leu Arg Lys Arg Gly Ala Asp Met Ile Trp Cys Asn Ala Arg Thr
            100                 105                 110

Ser Ala Ser Gly Tyr Tyr Lys Lys Leu Gly Phe Ser Glu Gln Gly Glu
        115                 120                 125

Ala Phe Glu Thr Pro Pro Ala Gly Pro His Ile Leu Met Tyr Lys Arg
130                 135                 140

Leu Thr
145

<210> SEQ ID NO 13
<211> LENGTH: 146
<212> TYPE: PRT
<213> ORGANISM: Artificial Sequence
<220> FEATURE:
<223> OTHER INFORMATION: GLYAT variant

<400> SEQUENCE: 13

Met Leu Glu Val Lys Pro Ile Asn Ala Glu Asp Thr Tyr Asp Leu Arg
1               5                   10                  15

His Arg Val Leu Arg Pro Asn Gln Pro Ile Glu Val Cys Met Tyr Glu
            20                  25                  30

Ser Asp Leu Thr Arg Ser Ala Phe His Leu Gly Gly Phe Tyr Gly Ala
        35                  40                  45

Lys Leu Ile Ser Val Ala Ser Phe His Gln Ala Glu His Ser Glu Leu
50                  55                  60

Gln Gly Lys Lys Gln Tyr Gln Leu Arg Gly Val Ala Thr Leu Gly Gly
65                  70                  75                  80

Tyr Arg Asp Gln Lys Ala Gly Ser Ser Leu Val Lys His Ala Glu Glu
```

```
            85                  90                  95
Ile Leu Arg Lys Arg Gly Ala Asp Met Ile Trp Cys Asn Ala Arg Thr
                100                 105                 110

Ser Ala Ser Gly Tyr Tyr Lys Lys Leu Gly Phe Ser Glu Gln Gly Glu
            115                 120                 125

Val Phe Glu Thr Pro Pro Ala Gly Pro His Ile Leu Met Tyr Lys Arg
        130                 135                 140

Leu Thr
145

<210> SEQ ID NO 14
<211> LENGTH: 146
<212> TYPE: PRT
<213> ORGANISM: Artificial Sequence
<220> FEATURE:
<223> OTHER INFORMATION: GLYAT variant

<400> SEQUENCE: 14

Met Leu Glu Val Lys Pro Ile Asn Ala Glu Asp Thr Tyr Asp Leu Arg
1               5                   10                  15

His Arg Val Leu Arg Pro Asn Gln Pro Ile Glu Val Cys Met Trp Glu
            20                  25                  30

Ser Asp Leu Thr Arg Ser Ala Phe His Leu Gly Gly Phe Tyr Gly Ala
        35                  40                  45

Lys Leu Ile Ser Val Ala Ser Phe His Gln Ala Glu His Ser Glu Leu
    50                  55                  60

Gln Gly Lys Lys Gln Tyr Gln Leu Arg Gly Val Ala Thr Leu Gly Gly
65                  70                  75                  80

Tyr Arg Gly Gln Lys Ala Gly Ser Ser Leu Val Lys His Ala Glu Glu
                85                  90                  95

Ile Leu Arg Lys Arg Gly Ala Asp Met Ile Trp Cys Asn Ala Arg Thr
                100                 105                 110

Ser Ala Ser Gly Tyr Tyr Lys Lys Leu Gly Phe Ser Glu Gln Gly Glu
            115                 120                 125

Val Phe Glu Thr Pro Pro Ala Gly Pro His Ile Leu Met Tyr Lys Arg
        130                 135                 140

Leu Thr
145

<210> SEQ ID NO 15
<211> LENGTH: 147
<212> TYPE: PRT
<213> ORGANISM: Artificial Sequence
<220> FEATURE:
<223> OTHER INFORMATION: GLYAT variant

<400> SEQUENCE: 15

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Cys Met Tyr
            20                  25                  30

Glu Ser Asp Leu Thr Arg Ser Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80
```

-continued

Gly Tyr Arg Glu Gln Lys Ala Gly Ser Ser Leu Val Lys His Ala Glu
                85                  90                  95

Glu Ile Leu Arg Lys Arg Gly Ala Asp Met Ile Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 16
<211> LENGTH: 146
<212> TYPE: PRT
<213> ORGANISM: Artificial Sequence
<220> FEATURE:
<223> OTHER INFORMATION: GLYAT variant

<400> SEQUENCE: 16

Met Leu Glu Val Lys Pro Ile Asn Ala Glu Asp Thr Tyr Asp Leu Arg
1               5                   10                  15

His Arg Val Leu Arg Pro Asn Gln Pro Ile Glu Val Cys Met Trp Glu
            20                  25                  30

Ser Asp Leu Thr Arg Ser Ala Phe His Leu Gly Gly Phe Tyr Gly Ala
        35                  40                  45

Lys Leu Ile Ser Val Ala Ser Phe His Gln Ala Glu His Ser Glu Leu
    50                  55                  60

Gln Gly Lys Lys Gln Tyr Gln Leu Arg Gly Val Ala Thr Leu Gly Gly
65                  70                  75                  80

Tyr Arg Asp Gln Lys Ala Gly Ser Ser Leu Val Lys His Ala Glu Glu
                85                  90                  95

Ile Leu Arg Lys Arg Gly Ala Asp Met Ile Trp Cys Asn Ala Arg Thr
            100                 105                 110

Ser Ala Ser Gly Tyr Tyr Lys Lys Leu Gly Phe Ser Glu Gln Gly Glu
        115                 120                 125

Val Phe Glu Tyr Pro Pro Ala Gly Pro His Ile Leu Met Tyr Lys Arg
    130                 135                 140

Leu Thr
145

<210> SEQ ID NO 17
<211> LENGTH: 146
<212> TYPE: PRT
<213> ORGANISM: Artificial Sequence
<220> FEATURE:
<223> OTHER INFORMATION: GLYAT variant

<400> SEQUENCE: 17

Met Leu Glu Val Lys Pro Ile Asn Ala Glu Asp Thr Tyr Asp Leu Arg
1               5                   10                  15

His Arg Val Leu Arg Pro Asn Gln Pro Phe Glu Val Cys Met Phe Glu
            20                  25                  30

Ser Asp Leu Thr Glu Ser Ala Phe His Leu Gly Gly Phe Tyr Gly Ala
        35                  40                  45

Glu Leu Ile Ser Val Ala Ser Phe His Gln Ala Glu His Ser Glu Leu
    50                  55                  60

Gln Gly Lys Lys Gln Tyr Gln Leu Arg Gly Val Ala Thr Leu Gly Gly
65                  70                  75                  80

```
Tyr Arg Asn Gln Lys Ala Gly Ser Ser Leu Val Lys His Ala Glu Glu
                85                  90                  95

Ile Leu Arg Ala Arg Gly Ala Asp Met Ile Trp Cys Asn Ala Arg Thr
            100                 105                 110

Ser Ala Ser Gly Tyr Tyr Lys Lys Leu Gly Phe Ser Glu Gln Gly Glu
        115                 120                 125

Val Phe Glu Thr Lys Pro Ala Gly Pro His Ile Leu Met Tyr Lys Arg
    130                 135                 140

Leu Thr
145

<210> SEQ ID NO 18
<211> LENGTH: 146
<212> TYPE: PRT
<213> ORGANISM: Artificial Sequence
<220> FEATURE:
<223> OTHER INFORMATION: GLYAT variant

<400> SEQUENCE: 18

Met Leu Glu Val Lys Pro Ile Asn Ala Glu Asp Thr Tyr Asp Leu Arg
1               5                   10                  15

His Arg Val Leu Arg Pro Asn Gln Pro Ile Glu Val Cys Met Trp Glu
            20                  25                  30

Ser Asp Leu Thr Arg Ser Ala Phe His Leu Gly Gly Phe Tyr Gly Ala
        35                  40                  45

Lys Leu Ile Ser Val Ala Ser Phe His Gln Ala Glu His Ser Glu Leu
    50                  55                  60

Gln Gly Lys Lys Gln Tyr Gln Leu Arg Gly Val Ala Thr Leu Gly Gly
65                  70                  75                  80

Tyr Arg Asp Gln Lys Ala Gly Ser Ser Leu Val Lys His Ala Glu Glu
                85                  90                  95

Ile Leu Arg Lys Arg Gly Ala Asp Met Ile Trp Cys Asn Ala Arg Thr
            100                 105                 110

Ser Ala Ser Gly Tyr Tyr Lys Lys Leu Gly Phe Ser Glu Gln Gly Glu
        115                 120                 125

Val Phe Glu Thr Pro Pro Ala Gly Pro His Ile Leu Met Tyr Lys Arg
    130                 135                 140

Leu Thr
145

<210> SEQ ID NO 19
<211> LENGTH: 147
<212> TYPE: PRT
<213> ORGANISM: Artificial Sequence
<220> FEATURE:
<223> OTHER INFORMATION: GLYAT variant

<400> SEQUENCE: 19

Met Ala Leu Glu Val Lys Pro Ile Asn Ala Glu Asp Thr Tyr Asp Leu
1               5                   10                  15

Arg His Arg Val Leu Arg Pro Asn Gln Pro Ile Glu Val Cys Met Phe
            20                  25                  30

Glu Ser Asp Leu Thr Arg Ser Ala Phe His Leu Gly Gly Phe Tyr Gly
        35                  40                  45

Ala Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Gly
```

```
                65                  70                  75                  80
Gly Tyr Arg Asp Gln Lys Ala Gly Ser Ser Leu Val Lys His Ala Glu
                    85                  90                  95

Glu Ile Leu Arg Lys Arg Gly Ala Asp Met Ile Trp Cys Asn Ala Arg
                100                 105                 110

Thr Ser Ala Ser Gly Tyr Tyr Lys Lys Leu Gly Phe Ser Glu Gln Gly
                115                 120                 125

Glu Val Phe Glu Thr Pro Pro Ala Gly Pro His Ile Leu Met Tyr Lys
    130                 135                 140

Arg Leu Thr
145

<210> SEQ ID NO 20
<211> LENGTH: 146
<212> TYPE: PRT
<213> ORGANISM: Artificial Sequence
<220> FEATURE:
<223> OTHER INFORMATION: GLYAT variant

<400> SEQUENCE: 20

Met Leu Glu Val Lys Pro Ile Asn Ala Glu Asp Thr Tyr Asp Leu Arg
1               5                   10                  15

His Arg Val Leu Arg Pro Asn Gln Pro Ile Glu Val Cys Met Trp Glu
                20                  25                  30

Ser Asp Leu Thr Arg Ser Ala Phe His Leu Gly Gly Phe Tyr Gly Ala
            35                  40                  45

Lys Leu Ile Ser Val Ala Ser Phe His Gln Ala Glu His Ser Glu Leu
    50                  55                  60

Gln Gly Lys Lys Gln Tyr Gln Leu Arg Gly Val Ala Thr Leu Gly Gly
65                  70                  75                  80

Tyr Arg Asp Gln Lys Ala Gly Ser Ser Leu Val Lys His Ala Glu Glu
                85                  90                  95

Ile Leu Arg Lys Arg Gly Ala Asp Met Ile Trp Cys Gln Ala Arg Thr
                100                 105                 110

Ser Ala Ser Gly Tyr Tyr Lys Lys Leu Gly Phe Ser Glu Gln Gly Glu
            115                 120                 125

Val Phe Glu Thr Pro Pro Ala Gly Pro His Ile Leu Met Tyr Lys Arg
    130                 135                 140

Leu Thr
145

<210> SEQ ID NO 21
<211> LENGTH: 147
<212> TYPE: PRT
<213> ORGANISM: Artificial Sequence
<220> FEATURE:
<223> OTHER INFORMATION: GLYAT variant

<400> SEQUENCE: 21

Met Ala Ile Glu Val Lys Pro Ile Ser Ala Glu Asp Thr Tyr Asp Leu
1               5                   10                  15

Arg His Arg Val Leu Arg Pro Asn Gln Pro Ile Glu Ala Cys Met Phe
                20                  25                  30

Glu Ser Asp Leu Thr Arg Ser Ala Phe His Leu Gly Gly Phe Tyr Gly
            35                  40                  45

Gly Lys Leu Ile Ser Val Ala Ser Phe His Gln Ala Glu Arg Ser Glu
    50                  55                  60
```

```
Leu Gln Gly Lys Lys Gln Tyr Gln Leu Arg Gly Val Ala Thr Leu Glu
 65                  70                  75                  80

Gly Tyr Arg Asp Gln Lys Ala Gly Ser Ser Leu Val His Ala Glu
                 85                  90                  95

Glu Ile Leu Arg Lys Arg Gly Ala Asp Met Ile Trp Cys Asn Ala Arg
                100                 105                 110

Thr Ser Ala Ser Gly Tyr Tyr Arg Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145
```

```
<210> SEQ ID NO 22
<211> LENGTH: 147
<212> TYPE: PRT
<213> ORGANISM: Artificial Sequence
<220> FEATURE:
<223> OTHER INFORMATION: GLYAT variant

<400> SEQUENCE: 22

Met Ala Ile Glu Val Lys Pro Ile Asn Ala Glu Asp Thr Tyr Asp Leu
  1               5                  10                  15

Arg His Arg Val Leu Arg Pro Asn Gln Ser Ile Glu Val Cys Met Phe
                 20                  25                  30

Glu Thr Asp Leu Leu Arg Ser Ala Phe His Leu Gly Gly Phe Tyr Gly
             35                  40                  45

Gly Lys Leu Ile Ser Val Ala Ser Phe His Gln Ala Glu His Ser Glu
         50                  55                  60

Leu Gln Gly Lys Lys Gln Tyr Gln Leu Arg Gly Val Ala Thr Leu Gly
 65                  70                  75                  80

Gly Tyr Arg Asp Gln Lys Ala Gly Ser Ser Leu Val Arg His Ala Glu
                 85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145
```

```
<210> SEQ ID NO 23
<211> LENGTH: 146
<212> TYPE: PRT
<213> ORGANISM: Artificial Sequence
<220> FEATURE:
<223> OTHER INFORMATION: GLYAT variant

<400> SEQUENCE: 23

Met Leu Glu Val Lys Pro Ile Asn Ala Glu Asp Thr Tyr Asp Leu Arg
  1               5                  10                  15

His Arg Val Leu Arg Pro Asn Gln Pro Phe Glu Val Cys Met Phe Glu
                 20                  25                  30

Ser Asp Leu Thr Arg Ser Ala Phe His Leu Gly Gly Phe Tyr Gly Ala
             35                  40                  45

Lys Leu Ile Ser Val Ala Ser Phe His Gln Ala Glu His Ser Glu Leu
         50                  55                  60
```

```
Gln Gly Lys Lys Gln Tyr Gln Leu Arg Gly Val Ala Thr Leu Glu Gly
 65                  70                  75                  80

Tyr Arg Asp Gln Lys Ala Gly Ser Ser Leu Val Lys His Ala Glu Glu
                 85                  90                  95

Ile Leu Arg Ala Arg Gly Ala Asp Met Leu Trp Cys Asn Ala Arg Thr
            100                 105                 110

Ser Ala Ser Gly Tyr Tyr Glu Lys Leu Gly Phe Ser Glu Gln Gly Glu
        115                 120                 125

Val Phe Glu Thr Pro Pro Ala Gly Pro His Ile Leu Met Tyr Lys Arg
    130                 135                 140

Leu Thr
145

<210> SEQ ID NO 24
<211> LENGTH: 146
<212> TYPE: PRT
<213> ORGANISM: Artificial Sequence
<220> FEATURE:
<223> OTHER INFORMATION: GLYAT variant

<400> SEQUENCE: 24

Met Leu Glu Val Lys Pro Ile Ser Ala Glu Asp Thr Tyr Asp Leu Arg
  1               5                  10                  15

His Arg Val Leu Arg Pro Asn Gln Pro Phe Glu Val Cys Met Phe Glu
                 20                  25                  30

Thr Asp Leu Leu Arg Ser Ala Phe His Leu Gly Gly Phe Tyr Gly Gly
             35                  40                  45

Lys Leu Ile Ser Val Ala Ser Phe His Gln Ala Glu His Ser Glu Leu
 50                  55                  60

Gln Gly Lys Lys Gln Tyr Gln Leu Arg Gly Val Ala Thr Leu Gly Gly
 65                  70                  75                  80

Tyr Arg Gly Gln Lys Ala Gly Ser Ser Leu Val Arg His Ala Glu Glu
                 85                  90                  95

Ile Leu Arg Lys Arg Gly Ala Asp Met Ile Trp Cys Asn Ala Arg Thr
            100                 105                 110

Ser Ala Ser Gly Tyr Tyr Glu Lys Leu Gly Phe Ser Glu Gln Gly Glu
        115                 120                 125

Val Phe Glu Tyr Pro Pro Ala Gly Pro His Ile Leu Met Tyr Lys Arg
    130                 135                 140

Leu Thr
145

<210> SEQ ID NO 25
<211> LENGTH: 147
<212> TYPE: PRT
<213> ORGANISM: Artificial Sequence
<220> FEATURE:
<223> OTHER INFORMATION: GLYAT variant

<400> SEQUENCE: 25

Met Ala Leu Glu Val Lys Pro Ile Ser Ala Glu Asp Thr Tyr Asp Leu
  1               5                  10                  15

Arg His Arg Val Leu Arg Pro Asn Gln Pro Phe Glu Val Ile Met Phe
                 20                  25                  30

Glu Thr Asp Leu Leu Arg Ser Ala Phe His Leu Gly Gly Phe Tyr Gly
             35                  40                  45

Gly Lys Leu Ile Ser Val Ala Ser Phe His Gln Ala Glu His Ser Glu
```

```
Leu Gln Gly Lys Lys Gln Tyr Gln Leu Arg Gly Val Ala Thr Leu Gly
 65                  70                  75                  80

Gly Tyr Arg Gly Gln Lys Ala Gly Ser Ser Leu Val Arg His Ala Glu
             85                  90                  95

Glu Ile Leu Arg Lys Arg Gly Ala Asp Met Ile Trp Cys Asn Ala Arg
            100                 105                 110

Thr Ser Ala Ser Gly Tyr Tyr Glu Lys Leu Gly Phe Ser Glu Gln Gly
            115                 120                 125

Glu Val Phe Glu Tyr Pro Pro Ala Gly Pro His Ile Leu Met Tyr Lys
        130                 135                 140

Arg Leu Thr
145
```

<210> SEQ ID NO 26
<211> LENGTH: 147
<212> TYPE: PRT
<213> ORGANISM: Artificial Sequence
<220> FEATURE:
<223> OTHER INFORMATION: GLYAT variant

<400> SEQUENCE: 26

```
Met Ala Ile Glu Val Lys Pro Ile Asn Ala Glu Asp Thr Tyr Asp Leu
 1               5                  10                  15

Arg His Arg Val Leu Arg Pro Asn Gln Pro Ile Glu Val Ile Met Tyr
             20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
         50                  55                  60

Leu Gln Gly Lys Lys Gln Tyr Gln Leu Arg Gly Val Ala Thr Leu Glu
 65                  70                  75                  80

Gly Tyr Arg Asp Gln Lys Ala Gly Ser Ser Leu Val Lys His Ala Glu
             85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145
```

<210> SEQ ID NO 27
<211> LENGTH: 147
<212> TYPE: PRT
<213> ORGANISM: Artificial Sequence
<220> FEATURE:
<223> OTHER INFORMATION: GLYAT variant

<400> SEQUENCE: 27

```
Met Ala Ile Glu Val Lys Pro Ile Asn Ala Glu Asp Thr Tyr Asp Leu
 1               5                  10                  15

Arg His Arg Val Leu Arg Pro Asn Gln Pro Ile Glu Val Ile Met Tyr
             20                  25                  30

Glu Thr Asp Leu Leu Arg Gly Ala Phe His Leu Gly Gly Phe Tyr Gly
            35                  40                  45
```

Gly Lys Leu Ile Ser Val Ala Ser Phe His Gln Ala Glu His Ser Glu
        50                  55                  60

Leu Gln Gly Lys Gln Tyr Gln Leu Arg Gly Val Ala Thr Leu Glu
 65                  70                  75                  80

Gly Tyr Arg Asp Gln Lys Ala Gly Ser Ser Leu Val Lys His Ala Glu
                    85                  90                  95

Glu Ile Leu Arg Lys Leu Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
        130                 135                 140

Arg Leu Thr
145

<210> SEQ ID NO 28
<211> LENGTH: 147
<212> TYPE: PRT
<213> ORGANISM: Artificial Sequence
<220> FEATURE:
<223> OTHER INFORMATION: GLYAT variant

<400> SEQUENCE: 28

Met Ala Ile Glu Val Lys Pro Ile Asn Ala Glu Asp Thr Tyr Asp Leu
 1               5                  10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Phe Tyr Gly
            35                  40                  45

Gly Lys Leu Ile Ser Val Ala Ser Phe His Gln Ala Glu His Ser Glu
        50                  55                  60

Leu Gln Gly Lys Val Gln Tyr Gln Leu Arg Gly Val Ala Thr Leu Glu
 65                  70                  75                  80

Gly Tyr Arg Asp Gln Arg Ala Ala Ser Thr Val Met Lys His Ala Glu
                    85                  90                  95

Glu Ile Leu Ala Arg Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
        130                 135                 140

Arg Leu Thr
145

<210> SEQ ID NO 29
<211> LENGTH: 147
<212> TYPE: PRT
<213> ORGANISM: Artificial Sequence
<220> FEATURE:
<223> OTHER INFORMATION: GLYAT variant

<400> SEQUENCE: 29

Met Ala Ile Glu Val Lys Pro Ile Asn Ala Glu Asp Thr Tyr Asp Leu
 1               5                  10                  15

Arg His Arg Val Leu Arg Pro Asn Gln Pro Ile Glu Val Ile Met Tyr
                20                  25                  30

Glu Thr Asp Leu Leu Arg Gly Ala Phe Ser Leu Gly Gly Phe Tyr Gly
            35                  40                  45

Gly Lys Leu Ile Ser Val Ala Ser Phe His Gln Ala Glu His Ser Glu
        50                  55                  60

Leu Gln Gly Lys Val Gln Tyr Gln Leu Arg Gly Val Ala Thr Leu Glu
65                  70                  75                  80

Gly Tyr Arg Asp Gln Arg Ala Gly Ser Thr Val Met Lys His Ala Glu
                85                  90                  95

Glu Ile Leu Arg Lys Leu Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
            130                 135                 140

Arg Leu Thr
145

<210> SEQ ID NO 30
<211> LENGTH: 147
<212> TYPE: PRT
<213> ORGANISM: Artificial Sequence
<220> FEATURE:
<223> OTHER INFORMATION: GLYAT variant

<400> SEQUENCE: 30

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
        50                  55                  60

Leu Gln Gly Lys Val Gln Tyr Gln Leu Arg Gly Val Ala Thr Leu Glu
65                  70                  75                  80

Gly Tyr Arg Asp Gln Lys Ala Ala Ser Ser Val Met Lys His Ala Glu
                85                  90                  95

Glu Ile Leu Ala Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Cys Lys
            130                 135                 140

Arg Leu Thr
145

<210> SEQ ID NO 31
<211> LENGTH: 147
<212> TYPE: PRT
<213> ORGANISM: Artificial Sequence
<220> FEATURE:
<223> OTHER INFORMATION: GLYAT variant

<400> SEQUENCE: 31

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly

```
                35                  40                  45
Gly Lys Leu Ile Ser Val Ala Ser Phe His Gly Ala Leu His Ser Glu
 50                  55                  60

Leu Gln Gly Lys Lys Gln Tyr Gln Leu Arg Gly Val Ala Thr Leu Glu
 65                  70                  75                  80

Gly Tyr Arg Asp Gln Arg Ala Ala Ser Thr Val Met Lys His Ala Glu
                 85                  90                  95

Glu Ile Leu Arg Lys Leu Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
                130                 135                 140

Arg Leu Thr
145

<210> SEQ ID NO 32
<211> LENGTH: 147
<212> TYPE: PRT
<213> ORGANISM: Artificial Sequence
<220> FEATURE:
<223> OTHER INFORMATION: GLYAT variant

<400> SEQUENCE: 32

Met Ala Ile Glu Val Lys Pro Ile Asn Ala Glu Asp Thr Tyr Asp Leu
  1               5                  10                  15

Arg His Arg Val Leu Arg Pro Asn Gln Pro Ile Glu Val Ile Met Tyr
                 20                  25                  30

Glu Thr Asp Leu Leu Arg Gly Ala Phe His Leu Gly Gly Phe Tyr Gly
                 35                  40                  45

Gly Lys Leu Ile Ser Val Ala Ser Phe His Gln Ala Glu His Ser Glu
 50                  55                  60

Leu Gln Gly Lys Lys Gln Tyr Gln Leu Arg Gly Val Ala Thr Leu Glu
 65                  70                  75                  80

Gly Tyr Arg Asp Gln Lys Ala Gly Ser Ser Leu Met Lys His Ala Glu
                 85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Cys Lys
                130                 135                 140

Arg Leu Thr
145

<210> SEQ ID NO 33
<211> LENGTH: 147
<212> TYPE: PRT
<213> ORGANISM: Artificial Sequence
<220> FEATURE:
<223> OTHER INFORMATION: GLYAT variant

<400> SEQUENCE: 33

Met Ala Ile Glu Val Lys Pro Ile Asn Ala Glu Asp Thr Tyr Asp Leu
  1               5                  10                  15

Arg His Arg Val Leu Arg Pro Asn Gln Pro Ile Glu Val Ile Met Tyr
                 20                  25                  30
```

```
Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Leu His Ser Glu
 50                      55                  60

Leu Gln Gly Lys Val Gln Tyr Gln Leu Arg Gly Val Ala Thr Leu Glu
 65                  70                  75                  80

Gly Tyr Arg Asp Gln Lys Ala Gly Ser Thr Leu Val Lys His Ala Glu
                 85                  90                  95

Glu Ile Leu Arg Lys Leu Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
            130                 135                 140

Arg Leu Thr
145
```

<210> SEQ ID NO 34
<211> LENGTH: 147
<212> TYPE: PRT
<213> ORGANISM: Artificial Sequence
<220> FEATURE:
<223> OTHER INFORMATION: GLYAT variant

<400> SEQUENCE: 34

```
Met Ala Ile Glu Val Lys Pro Ile Asn Ala Glu Asp Thr Tyr Asp Leu
 1               5                  10                  15

Arg His Arg Val Leu Arg Pro Asn Gln Pro Ile Glu Val Ile Met Tyr
                 20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Leu His Ser Glu
 50                      55                  60

Leu Gln Gly Lys Val Gln Tyr Gln Leu Arg Gly Val Ala Thr Leu Glu
 65                  70                  75                  80

Gly Tyr Arg Asp Gln Lys Ala Gly Ser Thr Leu Met Lys His Ala Glu
                 85                  90                  95

Glu Ile Leu Arg Lys Leu Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Cys Lys
            130                 135                 140

Arg Leu Thr
145
```

<210> SEQ ID NO 35
<211> LENGTH: 147
<212> TYPE: PRT
<213> ORGANISM: Artificial Sequence
<220> FEATURE:
<223> OTHER INFORMATION: GLYAT variant

<400> SEQUENCE: 35

```
Met Ala Ile Glu Val Lys Pro Ile Asn Ala Glu Asp Thr Tyr Asp Leu
 1               5                  10                  15

Arg His Arg Val Leu Arg Pro Asn Gln Pro Ile Glu Val Ile Met Tyr
                 20                  25                  30
```

```
Glu Thr Asp Leu Leu Arg Gly Ala Phe His Leu Gly Phe Tyr Gly
        35                  40                  45

Gly Lys Leu Ile Ser Val Ala Ser Phe His Gly Ala Leu His Ser Glu
 50                  55                  60

Leu Gln Gly Lys Val Gln Tyr Gln Leu Arg Gly Val Ala Thr Leu Glu
 65                  70                  75                  80

Gly Tyr Arg Asp Gln Arg Ala Ala Ser Thr Val Met Lys His Ala Glu
                 85                  90                  95

Glu Ile Leu Arg Lys Leu Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
                130                 135                 140

Arg Leu Thr
145
```

<210> SEQ ID NO 36
<211> LENGTH: 147
<212> TYPE: PRT
<213> ORGANISM: Artificial Sequence
<220> FEATURE:
<223> OTHER INFORMATION: GLYAT variant

<400> SEQUENCE: 36

```
Met Ala Ile Glu Val Lys Pro Ile Asn Ala Glu Asp Thr Tyr Asp Leu
 1               5                  10                  15

Arg His Arg Val Leu Arg Pro Asn Gln Pro Ile Glu Val Ile Met Tyr
                 20                  25                  30

Glu Thr Asp Leu Leu Arg Gly Ala Phe His Leu Gly Gly Phe Tyr Gly
                 35                  40                  45

Gly Lys Leu Ile Ser Val Ala Ser Phe His Gln Ala Glu His Ser Glu
 50                  55                  60

Leu Gln Gly Lys Lys Gln Tyr Gln Leu Arg Gly Val Ala Thr Leu Glu
 65                  70                  75                  80

Gly Tyr Arg Asp Gln Arg Ala Ala Ser Thr Val Val Lys His Ala Glu
                 85                  90                  95

Glu Ile Leu Ala Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
                130                 135                 140

Arg Leu Thr
145
```

<210> SEQ ID NO 37
<211> LENGTH: 147
<212> TYPE: PRT
<213> ORGANISM: Artificial Sequence
<220> FEATURE:
<223> OTHER INFORMATION: GLYAT variant

<400> SEQUENCE: 37

```
Met Ala Ile Glu Val Lys Pro Ile Asn Ala Glu Asp Thr Tyr Asp Leu
 1               5                  10                  15

Arg His Arg Val Leu Arg Pro Asn Gln Pro Ile Glu Val Ile Met Tyr
```

```
            20                  25                  30
Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
        50                  55                  60

Leu Gln Gly Lys Val Gln Tyr Gln Leu Arg Gly Val Ala Thr Leu Glu
 65                  70                  75                  80

Gly Tyr Arg Asp Gln Lys Ala Ala Ser Thr Leu Met Lys His Ala Glu
                85                  90                  95

Glu Ile Met Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
            130                 135                 140

Arg Leu Thr
145

<210> SEQ ID NO 38
<211> LENGTH: 147
<212> TYPE: PRT
<213> ORGANISM: Artificial Sequence
<220> FEATURE:
<223> OTHER INFORMATION: GLYAT variant

<400> SEQUENCE: 38

Met Ala Ile Glu Val Lys Pro Ile Asn Ala Glu Asp Thr Tyr Asp Leu
 1               5                  10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gly Ala Leu His Ser Glu
        50                  55                  60

Leu Gln Gly Lys Lys Gln Tyr Gln Leu Arg Gly Val Ala Thr Leu Glu
 65                  70                  75                  80

Gly Tyr Arg Asp Gln Lys Ala Ala Ser Ser Val Met Lys His Ala Glu
                85                  90                  95

Glu Ile Leu Val Lys Leu Gly Ala Asp Met Leu Trp Cys Asn Ala Arg
            100                 105                 110

Met Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
            130                 135                 140

Arg Leu Thr
145

<210> SEQ ID NO 39
<211> LENGTH: 147
<212> TYPE: PRT
<213> ORGANISM: Artificial Sequence
<220> FEATURE:
<223> OTHER INFORMATION: GLYAT variant

<400> SEQUENCE: 39

Met Ala Ile Glu Val Lys Pro Ile Asn Ala Glu Asp Thr Tyr Asp Leu
 1               5                  10                  15
```

```
Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Val Gln Tyr Gln Leu Arg Gly Val Ala Thr Leu Glu
 65                  70                  75                  80

Gly Tyr Arg Asp Gln Lys Ala Gly Ser Ser Val Met Lys His Ala Glu
            85                  90                  95

Glu Ile Leu Arg Lys Leu Gly Ala Asp Met Leu Trp Cys Asn Ala Arg
            100                 105                 110

Met Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
        130                 135                 140

Arg Leu Thr
145

<210> SEQ ID NO 40
<211> LENGTH: 147
<212> TYPE: PRT
<213> ORGANISM: Artificial Sequence
<220> FEATURE:
<223> OTHER INFORMATION: GLYAT variant

<400> SEQUENCE: 40

Met Ala Ile Glu Val Lys Pro Ile Asn Ala Glu Asp Thr Tyr Asp Leu
 1               5                  10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
 65                  70                  75                  80

Gly Tyr Arg Asp Gln Lys Ala Gly Ser Thr Val Met Lys His Ala Gln
            85                  90                  95

Glu Ile Leu Ala Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
        130                 135                 140

Arg Leu Thr
145

<210> SEQ ID NO 41
<211> LENGTH: 147
<212> TYPE: PRT
<213> ORGANISM: Artificial Sequence
<220> FEATURE:
<223> OTHER INFORMATION: GLYAT variant

<400> SEQUENCE: 41

Met Ala Ile Glu Val Lys Pro Ile Asn Ala Glu Asp Thr Tyr Asp Leu
 1               5                  10                  15
```

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
         35                  40                  45

Gly Lys Leu Ile Ser Val Ala Ser Phe His Gln Ala Leu His Ser Glu
     50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Ala Ser Asn Val Met Lys His Ala Glu
                 85                  90                  95

Glu Ile Leu Arg Lys Arg Gly Ala Asp Met Leu Trp Cys Asn Ala Arg
             100                 105                 110

Thr Ser Ala Ser Gly Tyr Tyr Glu Lys Leu Gly Phe Ser Glu Gln Gly
         115                 120                 125

Glu Val Phe Glu Thr Pro Pro Ala Gly Pro His Ile Leu Met Tyr Lys
     130                 135                 140

Arg Leu Thr
145

<210> SEQ ID NO 42
<211> LENGTH: 147
<212> TYPE: PRT
<213> ORGANISM: Artificial Sequence
<220> FEATURE:
<223> OTHER INFORMATION: GLYAT variant

<400> SEQUENCE: 42

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
         35                  40                  45

Gly Lys Leu Ile Ser Val Ala Ser Phe His Gln Ala Glu His Ser Glu
     50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Ala Ser Asn Val Met Lys His Ala Glu
                 85                  90                  95

Glu Ile Leu Ala Lys Arg Gly Ala Asp Met Leu Trp Cys Asn Ala Arg
             100                 105                 110

Thr Ser Ala Ser Gly Tyr Tyr Glu Lys Leu Gly Phe Ser Glu Gln Gly
         115                 120                 125

Glu Val Phe Glu Thr Pro Pro Ala Gly Pro His Ile Leu Met Tyr Lys
     130                 135                 140

Arg Leu Thr
145

<210> SEQ ID NO 43
<211> LENGTH: 147
<212> TYPE: PRT
<213> ORGANISM: Artificial Sequence
<220> FEATURE:
<223> OTHER INFORMATION: GLYAT variant

<400> SEQUENCE: 43

Met Ala Ile Glu Val Lys Pro Ile Asn Ala Glu Asp Thr Tyr Asp Leu

```
                1               5                  10                  15
Arg His Arg Val Leu Arg Pro Asn Gln Pro Ile Glu Val Ile Met Tyr
                20                  25                  30

Glu Thr Asp Leu Leu Arg Gly Ala Phe His Leu Gly Phe Tyr Gly
                35                  40                  45

Gly Lys Leu Ile Ser Val Ala Ser Phe His Gln Ala Glu His Ser Glu
         50                  55                  60

Leu Gln Gly Lys Lys Gln Tyr Gln Leu Arg Gly Val Ala Thr Leu Glu
65                   70                  75                  80

Gly Tyr Arg Asp Gln Lys Ala Ala Ser Thr Leu Val Lys His Ala Glu
                85                  90                  95

Glu Ile Leu Ala Lys Leu Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
                130                 135                 140

Arg Leu Thr
145
```

<210> SEQ ID NO 44
<211> LENGTH: 147
<212> TYPE: PRT
<213> ORGANISM: Artificial Sequence
<220> FEATURE:
<223> OTHER INFORMATION: GLYAT variant

<400> SEQUENCE: 44

```
Met Ala Ile Glu Val Lys Pro Ile Asn Ala Glu Asp Thr Tyr Asp Leu
1               5                  10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Phe Tyr Gly
                35                  40                  45

Gly Lys Leu Ile Ser Val Ala Ser Phe His Gln Ala Leu His Ser Glu
         50                  55                  60

Leu Gln Gly Lys Lys Gln Tyr Gln Leu Arg Gly Val Ala Thr Leu Glu
65                   70                  75                  80

Gly Tyr Arg Asp Gln Arg Ala Gly Ser Thr Val Met Lys His Ala Glu
                85                  90                  95

Glu Ile Leu Ala Lys Leu Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
                130                 135                 140

Arg Leu Thr
145
```

<210> SEQ ID NO 45
<211> LENGTH: 147
<212> TYPE: PRT
<213> ORGANISM: Artificial Sequence
<220> FEATURE:
<223> OTHER INFORMATION: GLYAT variant

<400> SEQUENCE: 45

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Leu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Lys Ala Ala Ser Thr Val Val Lys His Ala Glu
                85                  90                  95

Glu Ile Leu Ala Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 46
<211> LENGTH: 147
<212> TYPE: PRT
<213> ORGANISM: Artificial Sequence
<220> FEATURE:
<223> OTHER INFORMATION: GLYAT variant

<400> SEQUENCE: 46

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gly Ala Glu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Arg Ala Gly Ser Thr Leu Met Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 47
<211> LENGTH: 147
<212> TYPE: PRT
<213> ORGANISM: Artificial Sequence
<220> FEATURE:
<223> OTHER INFORMATION: GLYAT variant

<400> SEQUENCE: 47

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
        50                  55                  60

Leu Gln Gly Lys Lys Gln Tyr Gln Leu Arg Gly Val Ala Thr Leu Glu
65                  70                  75                  80

Gly Tyr Arg Asp Gln Arg Ala Ala Ser Ser Val Val Lys His Ala Glu
                85                  90                  95

Glu Ile Leu Ala Lys Leu Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 48
<211> LENGTH: 147
<212> TYPE: PRT
<213> ORGANISM: Artificial Sequence
<220> FEATURE:
<223> OTHER INFORMATION: GLYAT variant

<400> SEQUENCE: 48

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
        50                  55                  60

Leu Gln Gly Lys Val Gln Tyr Gln Leu Arg Gly Val Ala Thr Leu Glu
65                  70                  75                  80

Gly Tyr Arg Asp Gln Arg Ala Gly Ser Thr Leu Met Lys His Ala Glu
                85                  90                  95

Glu Ile Leu Val Lys Leu Gly Ala Asp Met Leu Trp Cys Asn Ala Arg
            100                 105                 110

Met Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 49
<211> LENGTH: 147
<212> TYPE: PRT
<213> ORGANISM: Artificial Sequence
<220> FEATURE:
<223> OTHER INFORMATION: GLYAT variant

<400> SEQUENCE: 49

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Arg Ala Gly Ser Thr Val Lys His Ala Glu
            85                  90                  95

Glu Ile Leu Val Lys Leu Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145

<210> SEQ ID NO 50
<211> LENGTH: 147
<212> TYPE: PRT
<213> ORGANISM: Artificial Sequence
<220> FEATURE:
<223> OTHER INFORMATION: GLYAT variant

<400> SEQUENCE: 50

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Leu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Thr Val Met Lys His Ala Glu
            85                  90                  95

Glu Ile Leu Val Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145

<210> SEQ ID NO 51
<211> LENGTH: 147
<212> TYPE: PRT
<213> ORGANISM: Artificial Sequence
<220> FEATURE:
<223> OTHER INFORMATION: GLYAT variant -continued

<400> SEQUENCE: 51

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Arg Ala Ala Ser Ser Val Met Lys His Ala Glu
                85                  90                  95

Glu Ile Leu Val Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 52
<211> LENGTH: 147
<212> TYPE: PRT
<213> ORGANISM: Artificial Sequence
<220> FEATURE:
<223> OTHER INFORMATION: GLYAT variant

<400> SEQUENCE: 52

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Leu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Arg Ala Gly Ser Thr Val Met Lys His Ala Glu
                85                  90                  95

Glu Ile Leu Val Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 53
<211> LENGTH: 147
<212> TYPE: PRT
<213> ORGANISM: Artificial Sequence
<220> FEATURE:

<223> OTHER INFORMATION: GLYAT variant

<400> SEQUENCE: 53

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Arg Ala Gly Ser Ser Val Met Lys His Ala Glu
                85                  90                  95

Glu Ile Leu Ala Lys Leu Gly Ala Asp Met Leu Trp Cys Asn Ala Arg
            100                 105                 110

Met Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 54
<211> LENGTH: 147
<212> TYPE: PRT
<213> ORGANISM: Artificial Sequence
<220> FEATURE:
<223> OTHER INFORMATION: GLYAT variant

<400> SEQUENCE: 54

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Arg Ala Ala Ser Thr Val Met Lys His Ala Glu
                85                  90                  95

Glu Ile Leu Arg Lys Leu Gly Ala Asp Met Leu Trp Cys Asn Ala Arg
            100                 105                 110

Met Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 55
<211> LENGTH: 147
<212> TYPE: PRT
<213> ORGANISM: Artificial Sequence
<220> FEATURE:
<223> OTHER INFORMATION: GLYAT variant

<400> SEQUENCE: 55

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Arg Ala Gly Ser Ser Leu Met Lys His Ala Glu
            85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145

<210> SEQ ID NO 56
<211> LENGTH: 147
<212> TYPE: PRT
<213> ORGANISM: Artificial Sequence
<220> FEATURE:
<223> OTHER INFORMATION: GLYAT variant

<400> SEQUENCE: 56

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Leu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Lys Ala Gly Ser Thr Val Met Lys His Ala Glu
            85                  90                  95

Glu Ile Leu Ala Lys Leu Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Cys Lys
        130                 135                 140

Arg Leu Thr
145

<210> SEQ ID NO 57
<211> LENGTH: 147
<212> TYPE: PRT

<213> ORGANISM: Artificial Sequence
<220> FEATURE:
<223> OTHER INFORMATION: GLYAT variant

<400> SEQUENCE: 57

```
Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Lys Ala Gly Ser Ser Leu Met Lys His Ala Glu
                85                  90                  95

Glu Ile Leu Arg Lys Leu Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145
```

<210> SEQ ID NO 58
<211> LENGTH: 147
<212> TYPE: PRT
<213> ORGANISM: Artificial Sequence
<220> FEATURE:
<223> OTHER INFORMATION: GLYAT variant

<400> SEQUENCE: 58

```
Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Thr Val Met Lys His Ala Glu
                85                  90                  95

Glu Ile Leu Val Lys Leu Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Cys Lys
    130                 135                 140

Arg Leu Thr
145
```

<210> SEQ ID NO 59
<211> LENGTH: 147

```
<212> TYPE: PRT
<213> ORGANISM: Artificial Sequence
<220> FEATURE:
<223> OTHER INFORMATION: GLYAT variant

<400> SEQUENCE: 59

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Lys Ala Ala Ser Ser Leu Met Lys His Ala Glu
                85                  90                  95

Glu Ile Leu Arg Lys Leu Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 60
<211> LENGTH: 147
<212> TYPE: PRT
<213> ORGANISM: Artificial Sequence
<220> FEATURE:
<223> OTHER INFORMATION: GLYAT variant

<400> SEQUENCE: 60

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Lys Ala Gly Ser Asn Val Met Lys His Ala Glu
                85                  90                  95

Glu Ile Leu Val Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Cys Lys
    130                 135                 140

Arg Leu Thr
145

<210> SEQ ID NO 61
```

```
<211> LENGTH: 147
<212> TYPE: PRT
<213> ORGANISM: Artificial Sequence
<220> FEATURE:
<223> OTHER INFORMATION: GLYAT variant

<400> SEQUENCE: 61

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gly Ala Leu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Arg Ala Gly Ser Thr Val Met Lys His Ala Glu
                85                  90                  95

Glu Ile Leu Arg Lys Leu Gly Ala Asp Met Leu Trp Cys Asn Ala Arg
            100                 105                 110

Met Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 62
<211> LENGTH: 147
<212> TYPE: PRT
<213> ORGANISM: Artificial Sequence
<220> FEATURE:
<223> OTHER INFORMATION: GLYAT variant

<400> SEQUENCE: 62

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Lys Ala Ala Ser Thr Leu Met Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Cys Lys
    130                 135                 140

Arg Leu Thr
145
```

```
<210> SEQ ID NO 63
<211> LENGTH: 147
<212> TYPE: PRT
<213> ORGANISM: Artificial Sequence
<220> FEATURE:
<223> OTHER INFORMATION: GLYAT variant

<400> SEQUENCE: 63

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Leu His Ser Glu
        50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Thr Leu Val Lys His Ala Glu
                85                  90                  95

Glu Ile Leu Val Lys Leu Gly Ala Asp Met Leu Trp Cys Asn Ala Arg
                100                 105                 110

Met Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145

<210> SEQ ID NO 64
<211> LENGTH: 147
<212> TYPE: PRT
<213> ORGANISM: Artificial Sequence
<220> FEATURE:
<223> OTHER INFORMATION: GLYAT variant

<400> SEQUENCE: 64

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
        50                  55                  60

Leu Gln Gly Lys Val Gln Tyr Gln Leu Arg Gly Val Ala Thr Leu Glu
65                  70                  75                  80

Gly Tyr Arg Asp Gln Arg Ala Gly Ser Thr Val Met Lys His Ala Glu
                85                  90                  95

Glu Ile Leu Arg Lys Leu Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145
```

<210> SEQ ID NO 65
<211> LENGTH: 147
<212> TYPE: PRT
<213> ORGANISM: Artificial Sequence
<220> FEATURE:
<223> OTHER INFORMATION: GLYAT variant

<400> SEQUENCE: 65

```
Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Ala Ser Thr Leu Val Lys His Ala Glu
                85                  90                  95

Glu Ile Leu Val Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145
```

<210> SEQ ID NO 66
<211> LENGTH: 147
<212> TYPE: PRT
<213> ORGANISM: Artificial Sequence
<220> FEATURE:
<223> OTHER INFORMATION: GLYAT variant

<400> SEQUENCE: 66

```
Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Lys Ala Gly Ser Ser Val Met Lys His Ala Glu
                85                  90                  95

Glu Ile Leu Val Lys Leu Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145
```

<210> SEQ ID NO 67
<211> LENGTH: 147
<212> TYPE: PRT
<213> ORGANISM: Artificial Sequence
<220> FEATURE:
<223> OTHER INFORMATION: GLYAT variant

<400> SEQUENCE: 67

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
        50                  55                  60

Leu Gln Gly Lys Val Gln Tyr Gln Leu Arg Gly Val Ala Thr Leu Glu
65                  70                  75                  80

Gly Tyr Arg Asp Gln Arg Ala Gly Ser Ser Val Met Lys His Ala Glu
                85                  90                  95

Glu Ile Leu Val Lys Leu Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145

<210> SEQ ID NO 68
<211> LENGTH: 147
<212> TYPE: PRT
<213> ORGANISM: Artificial Sequence
<220> FEATURE:
<223> OTHER INFORMATION: GLYAT variant

<400> SEQUENCE: 68

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Leu His Ser Glu
        50                  55                  60

Leu Gln Gly Lys Val Gln Tyr Gln Leu Arg Gly Val Ala Thr Leu Glu
65                  70                  75                  80

Gly Tyr Arg Asp Gln Arg Ala Gly Ser Thr Val Val Lys His Ala Glu
                85                  90                  95

Glu Ile Leu Arg Lys Arg Gly Ala Asp Met Leu Trp Cys Asn Ala Arg
                100                 105                 110

Met Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr

-continued

<210> SEQ ID NO 69
<211> LENGTH: 147
<212> TYPE: PRT
<213> ORGANISM: Artificial Sequence
<220> FEATURE:
<223> OTHER INFORMATION: GLYAT variant

<400> SEQUENCE: 69

```
Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Leu His Ser Glu
    50                  55                  60

Leu Gln Gly Lys Gln Tyr Gln Leu Arg Gly Val Ala Thr Leu Glu
65                  70                  75                  80

Gly Tyr Arg Asp Gln Lys Ala Gly Ser Thr Leu Met Lys His Ala Glu
                85                  90                  95

Glu Ile Leu Ala Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145
```

<210> SEQ ID NO 70
<211> LENGTH: 147
<212> TYPE: PRT
<213> ORGANISM: Artificial Sequence
<220> FEATURE:
<223> OTHER INFORMATION: GLYAT variant

<400> SEQUENCE: 70

```
Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Phe Tyr Gly
        35                  40                  45

Gly Lys Leu Ile Ser Val Ala Ser Phe His Gln Ala Leu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Arg Ala Gly Ser Thr Leu Met Lys His Ala Glu
                85                  90                  95

Glu Ile Leu Val Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140
```

Arg Leu Thr
145

<210> SEQ ID NO 71
<211> LENGTH: 147
<212> TYPE: PRT
<213> ORGANISM: Artificial Sequence
<220> FEATURE:
<223> OTHER INFORMATION: GLYAT variant

<400> SEQUENCE: 71

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Leu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Arg Ala Ala Ser Thr Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 72
<211> LENGTH: 147
<212> TYPE: PRT
<213> ORGANISM: Artificial Sequence
<220> FEATURE:
<223> OTHER INFORMATION: GLYAT variant

<400> SEQUENCE: 72

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Arg Ala Ala Ser Ser Val Met Lys His Ala Glu
                85                  90                  95

Glu Ile Leu Ala Lys Leu Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Cys Lys
    130                 135                 140

Arg Leu Thr
145

<210> SEQ ID NO 73
<211> LENGTH: 147
<212> TYPE: PRT
<213> ORGANISM: Artificial Sequence
<220> FEATURE:
<223> OTHER INFORMATION: GLYAT variant

<400> SEQUENCE: 73

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gly Ala Glu His Ser Glu
50                  55                  60

Leu Gln Gly Lys Lys Gln Tyr Gln Leu Arg Gly Val Ala Thr Leu Glu
65                  70                  75                  80

Gly Tyr Arg Asp Gln Arg Ala Gly Ser Ser Val Met Lys His Ala Glu
                85                  90                  95

Glu Ile Leu Val Lys Leu Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 74
<211> LENGTH: 147
<212> TYPE: PRT
<213> ORGANISM: Artificial Sequence
<220> FEATURE:
<223> OTHER INFORMATION: GLYAT variant

<400> SEQUENCE: 74

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Leu His Ser Glu
50                  55                  60

Leu Gln Gly Lys Lys Gln Tyr Gln Leu Arg Gly Val Ala Thr Leu Glu
65                  70                  75                  80

Gly Tyr Arg Asp Gln Arg Ala Gly Ser Asn Val Met Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys

Arg Leu Thr
145

<210> SEQ ID NO 75
<211> LENGTH: 147
<212> TYPE: PRT
<213> ORGANISM: Artificial Sequence
<220> FEATURE:
<223> OTHER INFORMATION: GLYAT variant

<400> SEQUENCE: 75

Met Ala Ile Glu Val Lys Pro Ile Asn Ala Glu Asp Thr Tyr Asp Leu
1               5                   10                  15

Arg His Arg Val Leu Arg Pro Asn Gln Pro Met Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gly Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Ala Ser Asn Val Met Lys His Ala Glu
                85                  90                  95

Glu Ile Leu Arg Lys Leu Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 76
<211> LENGTH: 147
<212> TYPE: PRT
<213> ORGANISM: Artificial Sequence
<220> FEATURE:
<223> OTHER INFORMATION: GLYAT variant

<400> SEQUENCE: 76

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gly Ala Glu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Lys Ala Gly Ser Ser Val Met Lys His Ala Glu
                85                  90                  95

Glu Ile Leu Val Lys Leu Gly Ala Asp Met Leu Trp Cys Asn Ala Arg
            100                 105                 110

Met Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
            130                 135                 140

Arg Leu Thr
145

<210> SEQ ID NO 77
<211> LENGTH: 147
<212> TYPE: PRT
<213> ORGANISM: Artificial Sequence
<220> FEATURE:
<223> OTHER INFORMATION: GLYAT variant

<400> SEQUENCE: 77

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Leu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Arg Ala Gly Ser Thr Val Met Lys His Ala Glu
                85                  90                  95

Glu Ile Leu Arg Lys Arg Gly Ala Asp Met Leu Trp Cys Asn Ala Arg
            100                 105                 110

Met Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 78
<211> LENGTH: 147
<212> TYPE: PRT
<213> ORGANISM: Artificial Sequence
<220> FEATURE:
<223> OTHER INFORMATION: GLYAT variant

<400> SEQUENCE: 78

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Met Lys His Ala Glu
                85                  90                  95

Glu Ile Leu Val Lys Leu Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

```
Glu Val Phe Glu Thr Pro Pro Ala Gly Pro His Ile Leu Met Tyr Lys
        130                 135                 140

Arg Leu Thr
145

<210> SEQ ID NO 79
<211> LENGTH: 147
<212> TYPE: PRT
<213> ORGANISM: Artificial Sequence
<220> FEATURE:
<223> OTHER INFORMATION: GLYAT variant

<400> SEQUENCE: 79

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
50                  55                  60

Leu Gln Gly Lys Lys Gln Tyr Gln Leu Arg Gly Val Ala Thr Leu Glu
65                  70                  75                  80

Gly Tyr Arg Asp Gln Arg Ala Gly Ser Ser Val Met Lys His Ala Glu
                85                  90                  95

Glu Ile Leu Val Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
        130                 135                 140

Arg Leu Thr
145

<210> SEQ ID NO 80
<211> LENGTH: 147
<212> TYPE: PRT
<213> ORGANISM: Artificial Sequence
<220> FEATURE:
<223> OTHER INFORMATION: GLYAT variant

<400> SEQUENCE: 80

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Ala Ser Asn Leu Met Lys His Ala Glu
                85                  90                  95

Glu Ile Leu Ala Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
```

```
                115                 120                 125
Glu Val Phe Glu Thr Pro Pro Ala Gly Pro His Ile Leu Met Tyr Lys
        130                 135                 140

Arg Leu Thr
145

<210> SEQ ID NO 81
<211> LENGTH: 147
<212> TYPE: PRT
<213> ORGANISM: Artificial Sequence
<220> FEATURE:
<223> OTHER INFORMATION: GLYAT variant

<400> SEQUENCE: 81

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Leu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Lys Ala Gly Ser Asn Val Met Lys His Ala Glu
                85                  90                  95

Glu Ile Leu Val Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 82
<211> LENGTH: 147
<212> TYPE: PRT
<213> ORGANISM: Artificial Sequence
<220> FEATURE:
<223> OTHER INFORMATION: GLYAT variant

<400> SEQUENCE: 82

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Lys Ala Gly Ser Asn Val Met Lys His Ala Glu
                85                  90                  95

Glu Ile Leu Ala Lys Arg Gly Ala Asp Met Leu Trp Cys Asn Ala Arg
            100                 105                 110
```

```
Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Cys Lys
    130                 135                 140

Arg Leu Thr
145

<210> SEQ ID NO 83
<211> LENGTH: 147
<212> TYPE: PRT
<213> ORGANISM: Artificial Sequence
<220> FEATURE:
<223> OTHER INFORMATION: GLYAT variant

<400> SEQUENCE: 83

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gly Ala Glu His Ser Glu
50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Thr Val Met Lys His Ala Glu
                85                  90                  95

Glu Ile Leu Arg Lys Leu Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
    130                 135                 140

Arg Leu Thr
145

<210> SEQ ID NO 84
<211> LENGTH: 147
<212> TYPE: PRT
<213> ORGANISM: Artificial Sequence
<220> FEATURE:
<223> OTHER INFORMATION: GLYAT variant

<400> SEQUENCE: 84

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Ala Ser Thr Val Met Lys His Ala Glu
                85                  90                  95

Glu Ile Leu Ala Lys Arg Gly Ala Asp Met Leu Trp Cys Asn Ala Arg
            100                 105                 110
```

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
130                 135                 140

Arg Leu Thr
145

<210> SEQ ID NO 85
<211> LENGTH: 147
<212> TYPE: PRT
<213> ORGANISM: Artificial Sequence
<220> FEATURE:
<223> OTHER INFORMATION: GLYAT variant

<400> SEQUENCE: 85

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
50                  55                  60

Leu Gln Gly Lys Val Gln Tyr Gln Leu Arg Gly Val Ala Thr Leu Glu
65                  70                  75                  80

Gly Tyr Arg Asp Gln Lys Ala Ala Ser Asn Val Met Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Cys Lys
130                 135                 140

Arg Leu Thr
145

<210> SEQ ID NO 86
<211> LENGTH: 147
<212> TYPE: PRT
<213> ORGANISM: Artificial Sequence
<220> FEATURE:
<223> OTHER INFORMATION: GLYAT variant

<400> SEQUENCE: 86

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Leu His Ser Glu
50                  55                  60

Leu Gln Gly Lys Lys Gln Tyr Gln Leu Arg Gly Val Ala Thr Leu Glu
65                  70                  75                  80

Gly Tyr Arg Asp Gln Arg Ala Gly Ser Ser Val Met Lys His Ala Glu
                85                  90                  95

Glu Ile Leu Ala Lys Arg Gly Ala Asp Met Leu Trp Cys Asn Ala Arg

```
                100             105             110
Thr Ser Ala Ser Gly Tyr Tyr Glu Lys Leu Gly Phe Ser Glu Gln Gly
        115                 120                 125
Glu Val Phe Glu Thr Pro Pro Ala Gly Pro His Ile Leu Met Tyr Lys
    130                 135                 140
Arg Leu Thr
145
```

<210> SEQ ID NO 87
<211> LENGTH: 147
<212> TYPE: PRT
<213> ORGANISM: Artificial Sequence
<220> FEATURE:
<223> OTHER INFORMATION: GLYAT variant

<400> SEQUENCE: 87

```
Met Ala Ile Glu Val Lys Pro Ile Asn Ala Glu Asp Thr Tyr Asp Leu
1               5                   10                  15
Arg His Arg Val Leu Arg Pro Asn Gln Pro Ile Glu Val Ile Met Tyr
            20                  25                  30
Glu Thr Asp Leu Leu Arg Gly Ala Phe His Leu Gly Gly Phe Tyr Gly
        35                  40                  45
Gly Lys Leu Ile Ser Val Ala Ser Phe His Gln Ala Glu His Ser Glu
    50                  55                  60
Leu Gln Gly Lys Val Gln Tyr Gln Leu Arg Gly Val Ala Thr Leu Glu
65                  70                  75                  80
Gly Tyr Arg Asp Gln Lys Ala Gly Ser Thr Val Met Lys His Ala Glu
                85                  90                  95
Glu Ile Leu Ala Lys Leu Gly Ala Asp Met Leu Trp Cys Asn Ala Arg
            100                 105                 110
Met Ser Ala Ser Gly Tyr Tyr Glu Lys Leu Gly Phe Ser Glu Gln Gly
        115                 120                 125
Glu Val Phe Glu Thr Pro Pro Ala Gly Pro His Ile Leu Met Tyr Lys
    130                 135                 140
Arg Leu Thr
145
```

<210> SEQ ID NO 88
<211> LENGTH: 147
<212> TYPE: PRT
<213> ORGANISM: Artificial Sequence
<220> FEATURE:
<223> OTHER INFORMATION: GLYAT variant

<400> SEQUENCE: 88

```
Met Ala Ile Glu Val Lys Pro Ile Asn Ala Glu Asp Thr Tyr Asp Leu
1               5                   10                  15
Arg His Arg Val Leu Arg Pro Asn Gln Pro Ile Glu Val Ile Met Tyr
            20                  25                  30
Glu Thr Asp Leu Leu Arg Gly Ala Phe His Leu Gly Gly Phe Tyr Gly
        35                  40                  45
Gly Lys Leu Ile Ser Val Ala Ser Phe His Gln Ala Glu His Ser Glu
    50                  55                  60
Leu Gln Gly Lys Val Gln Tyr Gln Leu Arg Gly Val Ala Thr Leu Glu
65                  70                  75                  80
Gly Tyr Arg Asp Gln Lys Ala Gly Ser Ser Val Met Lys His Ala Glu
                85                  90                  95
```

```
Glu Ile Leu Arg Lys Leu Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
130                 135                 140

Arg Leu Thr
145

<210> SEQ ID NO 89
<211> LENGTH: 147
<212> TYPE: PRT
<213> ORGANISM: Artificial Sequence
<220> FEATURE:
<223> OTHER INFORMATION: GLYAT variant

<400> SEQUENCE: 89

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
50                  55                  60

Leu Gln Gly Lys Lys Gln Tyr Gln Leu Arg Gly Val Ala Thr Leu Glu
65                  70                  75                  80

Gly Tyr Arg Asp Gln Arg Ala Ala Ser Thr Leu Val Lys His Ala Glu
                85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
130                 135                 140

Arg Leu Thr
145

<210> SEQ ID NO 90
<211> LENGTH: 147
<212> TYPE: PRT
<213> ORGANISM: Artificial Sequence
<220> FEATURE:
<223> OTHER INFORMATION: GLYAT variant

<400> SEQUENCE: 90

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
50                  55                  60

Leu Gln Gly Lys Val Gln Tyr Gln Leu Arg Gly Val Ala Thr Leu Glu
65                  70                  75                  80

Gly Tyr Arg Asp Gln Arg Ala Ala Ser Asn Val Met Lys His Ala Glu
                85                  90                  95
```

```
Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
130                 135                 140

Arg Leu Thr
145

<210> SEQ ID NO 91
<211> LENGTH: 147
<212> TYPE: PRT
<213> ORGANISM: Artificial Sequence
<220> FEATURE:
<223> OTHER INFORMATION: GLYAT variant

<400> SEQUENCE: 91

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Phe Tyr Gly
            35                  40                  45

Gly Lys Leu Ile Ser Val Ala Ser Phe His Gln Ala Glu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Arg Ala Ala Ser Thr Val Met Lys His Ala Glu
                85                  90                  95

Glu Ile Leu Val Lys Leu Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
130                 135                 140

Arg Leu Thr
145

<210> SEQ ID NO 92
<211> LENGTH: 147
<212> TYPE: PRT
<213> ORGANISM: Artificial Sequence
<220> FEATURE:
<223> OTHER INFORMATION: GLYAT variant

<400> SEQUENCE: 92

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Phe Tyr Gly
            35                  40                  45

Gly Lys Leu Ile Ser Val Ala Ser Phe His Gly Ala Glu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Lys Ala Gly Ser Thr Val Met Lys His Ala Glu
```

```
                     85                  90                  95
Glu Ile Leu Arg Lys Leu Gly Ala Asp Met Leu Trp Cys Asn Ala Arg
            100                 105                 110
Thr Ser Ala Ser Gly Tyr Tyr Glu Lys Leu Gly Phe Ser Glu Gln Gly
        115                 120                 125
Glu Val Phe Glu Thr Pro Pro Ala Gly Pro His Ile Leu Met Tyr Lys
    130                 135                 140
Arg Leu Thr
145

<210> SEQ ID NO 93
<211> LENGTH: 147
<212> TYPE: PRT
<213> ORGANISM: Artificial Sequence
<220> FEATURE:
<223> OTHER INFORMATION: GLYAT variant

<400> SEQUENCE: 93

Met Ala Ile Glu Val Lys Pro Ile Asn Ala Glu Asp Thr Tyr Asp Leu
1               5                   10                  15
Arg His Arg Val Leu Arg Pro Asn Gln Pro Ile Glu Val Ile Met Tyr
            20                  25                  30
Glu Thr Asp Leu Leu Arg Gly Ala Phe His Leu Gly Gly Phe Tyr Gly
        35                  40                  45
Gly Lys Leu Ile Ser Val Ala Ser Phe His Gln Ala Leu His Ser Glu
    50                  55                  60
Leu Gln Gly Lys Lys Gln Tyr Gln Leu Arg Gly Val Ala Thr Leu Glu
65                  70                  75                  80
Gly Tyr Arg Asp Gln Arg Ala Gly Ser Ser Val Met Lys His Ala Glu
                85                  90                  95
Glu Ile Leu Arg Lys Leu Gly Ala Asp Met Leu Trp Cys Asn Ala Arg
            100                 105                 110
Thr Ser Ala Ser Gly Tyr Tyr Glu Lys Leu Gly Phe Ser Glu Gln Gly
        115                 120                 125
Glu Val Phe Glu Thr Pro Pro Ala Gly Pro His Ile Leu Met Tyr Lys
    130                 135                 140
Arg Leu Thr
145

<210> SEQ ID NO 94
<211> LENGTH: 147
<212> TYPE: PRT
<213> ORGANISM: Artificial Sequence
<220> FEATURE:
<223> OTHER INFORMATION: GLYAT variant

<400> SEQUENCE: 94

Met Ala Ile Glu Val Lys Pro Ile Asn Ala Glu Asp Thr Tyr Asp Leu
1               5                   10                  15
Arg His Arg Val Leu Arg Pro Asn Gln Pro Ile Glu Val Ile Met Tyr
            20                  25                  30
Glu Thr Asp Leu Leu Arg Gly Ala Phe His Leu Gly Gly Phe Tyr Gly
        35                  40                  45
Gly Lys Leu Ile Ser Val Ala Ser Phe His Gln Ala Leu His Ser Glu
    50                  55                  60
Leu Gln Gly Lys Lys Gln Tyr Gln Leu Arg Gly Val Ala Thr Leu Glu
65                  70                  75                  80
```

Gly Tyr Arg Asp Gln Arg Ala Gly Ser Ser Val Met Lys His Ala Glu
            85                  90                  95

Glu Ile Leu Arg Lys Arg Gly Ala Asp Met Leu Trp Cys Asn Ala Arg
        100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
    130                 135                 140

Arg Leu Thr
145

<210> SEQ ID NO 95
<211> LENGTH: 147
<212> TYPE: PRT
<213> ORGANISM: Artificial Sequence
<220> FEATURE:
<223> OTHER INFORMATION: GLYAT variant

<400> SEQUENCE: 95

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Arg Ala Gly Ser Ser Val Met Lys His Ala Glu
            85                  90                  95

Glu Ile Leu Arg Lys Arg Gly Ala Asp Met Leu Trp Cys Asn Ala Arg
        100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Cys Lys
    130                 135                 140

Arg Leu Thr
145

<210> SEQ ID NO 96
<211> LENGTH: 147
<212> TYPE: PRT
<213> ORGANISM: Artificial Sequence
<220> FEATURE:
<223> OTHER INFORMATION: GLYAT variant

<400> SEQUENCE: 96

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

-continued

```
Gly Tyr Arg Asp Gln Lys Ala Gly Ser Thr Val Met Lys His Ala Glu
                85                  90                  95

Glu Ile Met Ala Lys Leu Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 97
<211> LENGTH: 147
<212> TYPE: PRT
<213> ORGANISM: Artificial Sequence
<220> FEATURE:
<223> OTHER INFORMATION: GLYAT variant

<400> SEQUENCE: 97

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Leu His Ser Glu
    50                  55                  60

Leu Gln Gly Lys Val Gln Tyr Gln Leu Arg Gly Val Ala Thr Leu Glu
65                  70                  75                  80

Gly Tyr Arg Asp Gln Lys Ala Gly Ser Thr Val Met Lys His Ala Glu
                85                  90                  95

Glu Ile Leu Arg Lys Leu Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 98
<211> LENGTH: 147
<212> TYPE: PRT
<213> ORGANISM: Artificial Sequence
<220> FEATURE:
<223> OTHER INFORMATION: GLYAT variant

<400> SEQUENCE: 98

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
```

```
                65                  70                  75                  80
Gly Tyr Arg Asp Gln Arg Ala Ala Ser Thr Val Val Lys His Ala Glu
                    85                  90                  95

Glu Ile Leu Arg Lys Leu Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
            130                 135                 140

Arg Leu Thr
145

<210> SEQ ID NO 99
<211> LENGTH: 147
<212> TYPE: PRT
<213> ORGANISM: Artificial Sequence
<220> FEATURE:
<223> OTHER INFORMATION: GLYAT variant

<400> SEQUENCE: 99

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Phe Tyr Gly
            35                  40                  45

Gly Lys Leu Ile Ser Val Ala Ser Phe His Gln Ala Glu His Ser Glu
        50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Thr Leu Val Lys His Ala Glu
                    85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Cys Lys
            130                 135                 140

Arg Leu Thr
145

<210> SEQ ID NO 100
<211> LENGTH: 147
<212> TYPE: PRT
<213> ORGANISM: Artificial Sequence
<220> FEATURE:
<223> OTHER INFORMATION: GLYAT variant

<400> SEQUENCE: 100

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Phe Tyr Gly
            35                  40                  45

Gly Lys Leu Ile Ser Val Ala Ser Phe His Gln Ala Leu His Ser Glu
        50                  55                  60
```

```
Leu Gln Gly Lys Val Gln Tyr Gln Leu Arg Gly Val Ala Thr Leu Glu
 65                  70                  75                  80

Gly Tyr Arg Asp Gln Lys Ala Ala Ser Thr Val Met Lys His Ala Glu
                 85                  90                  95

Glu Ile Leu Arg Lys Leu Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145

<210> SEQ ID NO 101
<211> LENGTH: 147
<212> TYPE: PRT
<213> ORGANISM: Artificial Sequence
<220> FEATURE:
<223> OTHER INFORMATION: GLYAT variant

<400> SEQUENCE: 101

Met Ala Ile Glu Val Lys Pro Ile Asn Ala Glu Asp Thr Tyr Asp Leu
 1               5                  10                  15

Arg His Arg Val Leu Arg Pro Asn Gln Pro Ile Glu Val Ile Met Tyr
                 20                  25                  30

Glu Thr Asp Leu Leu Arg Gly Ala Phe His Leu Gly Gly Phe Tyr Gly
             35                  40                  45

Gly Lys Leu Ile Ser Val Ala Ser Phe His Gly Ala Glu His Ser Glu
         50                  55                  60

Leu Gln Gly Lys Lys Gln Tyr Gln Leu Arg Gly Val Ala Thr Leu Glu
 65                  70                  75                  80

Gly Tyr Arg Asp Gln Arg Ala Gly Ser Ser Val Met Lys His Ala Glu
                 85                  90                  95

Glu Ile Leu Ala Lys Leu Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145

<210> SEQ ID NO 102
<211> LENGTH: 147
<212> TYPE: PRT
<213> ORGANISM: Artificial Sequence
<220> FEATURE:
<223> OTHER INFORMATION: GLYAT variant

<400> SEQUENCE: 102

Met Ala Ile Asp Val Lys Pro Ile Asn Ala Glu Asp Thr Tyr Asp Leu
 1               5                  10                  15

Arg His Arg Val Leu Arg Pro Asn Gln Pro Ile Glu Val Ile Met Tyr
                 20                  25                  30

Glu Thr Asp Leu Leu Arg Gly Ala Phe His Leu Gly Gly Phe Tyr Gly
             35                  40                  45

Gly Lys Leu Ile Ser Val Ala Ser Phe His Gln Ala Glu His Ser Glu
         50                  55                  60
```

```
Leu Gln Gly Lys Lys Gln Tyr Gln Leu Arg Gly Val Ala Thr Leu Glu
 65                  70                  75                  80

Gly Tyr Arg Asp Gln Lys Ala Gly Ser Ser Leu Val Lys His Ala Glu
                 85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 103
<211> LENGTH: 147
<212> TYPE: PRT
<213> ORGANISM: Artificial Sequence
<220> FEATURE:
<223> OTHER INFORMATION: GLYAT variant

<400> SEQUENCE: 103

Met Ala Ile Ser Val Lys Pro Ile Asn Ala Glu Asp Thr Tyr Asp Leu
  1               5                  10                  15

Arg His Arg Val Leu Arg Pro Asn Gln Pro Ile Glu Val Ile Met Tyr
                 20                  25                  30

Glu Thr Asp Leu Leu Arg Gly Ala Phe His Leu Gly Gly Phe Tyr Gly
             35                  40                  45

Gly Lys Leu Ile Ser Val Ala Ser Phe His Gln Ala Glu His Ser Glu
         50                  55                  60

Leu Gln Gly Lys Lys Gln Tyr Gln Leu Arg Gly Val Ala Thr Leu Glu
 65                  70                  75                  80

Gly Tyr Arg Asp Gln Lys Ala Gly Ser Ser Leu Val Lys His Ala Glu
                 85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 104
<211> LENGTH: 147
<212> TYPE: PRT
<213> ORGANISM: Artificial Sequence
<220> FEATURE:
<223> OTHER INFORMATION: GLYAT variant

<400> SEQUENCE: 104

Met Ala Ile Cys Val Lys Pro Ile Asn Ala Glu Asp Thr Tyr Asp Leu
  1               5                  10                  15

Arg His Arg Val Leu Arg Pro Asn Gln Pro Ile Glu Val Ile Met Tyr
                 20                  25                  30

Glu Thr Asp Leu Leu Arg Gly Ala Phe His Leu Gly Gly Phe Tyr Gly
             35                  40                  45

Gly Lys Leu Ile Ser Val Ala Ser Phe His Gln Ala Glu His Ser Glu
```

```
Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145
```

<210> SEQ ID NO 105
<211> LENGTH: 147
<212> TYPE: PRT
<213> ORGANISM: Artificial Sequence
<220> FEATURE:
<223> OTHER INFORMATION: GLYAT variant

<400> SEQUENCE: 105

```
Met Ala Ile Glu Ile Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
        50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145
```

<210> SEQ ID NO 106
<211> LENGTH: 147
<212> TYPE: PRT
<213> ORGANISM: Artificial Sequence
<220> FEATURE:
<223> OTHER INFORMATION: GLYAT variant

<400> SEQUENCE: 106

```
Met Ala Ile Glu Val Lys Met Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45
```

```
Gly Lys Leu Ile Ser Val Ala Ser Phe His Gln Ala Glu His Ser Glu
         50                  55                  60

Leu Gln Gly Lys Lys Gln Tyr Gln Leu Arg Gly Val Ala Thr Leu Glu
 65                  70                  75                  80

Gly Tyr Arg Asp Gln Lys Ala Gly Ser Ser Leu Val Lys His Ala Glu
                 85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
            130                 135                 140

Arg Leu Thr
145

<210> SEQ ID NO 107
<211> LENGTH: 147
<212> TYPE: PRT
<213> ORGANISM: Artificial Sequence
<220> FEATURE:
<223> OTHER INFORMATION: GLYAT variant

<400> SEQUENCE: 107

Met Ala Ile Glu Val Lys Pro Ile Gly Ala Glu Asp Thr Tyr Asp Leu
 1               5                  10                  15

Arg His Arg Val Leu Arg Pro Asn Gln Pro Ile Glu Val Ile Met Tyr
                 20                  25                  30

Glu Thr Asp Leu Leu Arg Gly Ala Phe His Leu Gly Gly Phe Tyr Gly
             35                  40                  45

Gly Lys Leu Ile Ser Val Ala Ser Phe His Gln Ala Glu His Ser Glu
         50                  55                  60

Leu Gln Gly Lys Lys Gln Tyr Gln Leu Arg Gly Val Ala Thr Leu Glu
 65                  70                  75                  80

Gly Tyr Arg Asp Gln Lys Ala Gly Ser Ser Leu Val Lys His Ala Glu
                 85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
            130                 135                 140

Arg Leu Thr
145

<210> SEQ ID NO 108
<211> LENGTH: 147
<212> TYPE: PRT
<213> ORGANISM: Artificial Sequence
<220> FEATURE:
<223> OTHER INFORMATION: GLYAT variant

<400> SEQUENCE: 108

Met Ala Ile Glu Val Lys Pro Ile Ser Ala Glu Asp Thr Tyr Asp Leu
 1               5                  10                  15

Arg His Arg Val Leu Arg Pro Asn Gln Pro Ile Glu Val Ile Met Tyr
                 20                  25                  30

Glu Thr Asp Leu Leu Arg Gly Ala Phe His Leu Gly Gly Phe Tyr Gly
             35                  40                  45
```

Gly Lys Leu Ile Ser Val Ala Ser Phe His Gln Ala Glu His Ser Glu
            50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
            130                 135                 140

Arg Leu Thr
145

<210> SEQ ID NO 109
<211> LENGTH: 147
<212> TYPE: PRT
<213> ORGANISM: Artificial Sequence
<220> FEATURE:
<223> OTHER INFORMATION: GLYAT variant

<400> SEQUENCE: 109

Met Ala Ile Glu Val Lys Pro Ile Thr Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
            50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
            130                 135                 140

Arg Leu Thr
145

<210> SEQ ID NO 110
<211> LENGTH: 147
<212> TYPE: PRT
<213> ORGANISM: Artificial Sequence
<220> FEATURE:
<223> OTHER INFORMATION: GLYAT variant

<400> SEQUENCE: 110

Met Ala Ile Glu Val Lys Pro Ile Asn Ala Glu Asp Thr Tyr Asp Leu
1               5                   10                  15

Arg His Arg Val Leu Arg Pro Gly Gln Pro Ile Glu Val Ile Met Tyr
            20                  25                  30

Glu Thr Asp Leu Leu Arg Gly Ala Phe His Leu Gly Gly Phe Tyr Gly 35                  40                  45
Gly Lys Leu Ile Ser Val Ala Ser Phe His Gln Ala Glu His Ser Glu
        50                  55                  60
Leu Gln Gly Lys Lys Gln Tyr Gln Leu Arg Gly Val Ala Thr Leu Glu
65                  70                  75                  80
Gly Tyr Arg Asp Gln Lys Ala Gly Ser Ser Leu Val Lys His Ala Glu
                85                  90                  95
Glu Ile Leu Arg Lys Arg Gly Ala Asp Met Leu Trp Cys Asn Ala Arg
            100                 105                 110
Thr Ser Ala Ser Gly Tyr Tyr Glu Lys Leu Gly Phe Ser Glu Gln Gly
        115                 120                 125
Glu Val Phe Glu Thr Pro Pro Ala Gly Pro His Ile Leu Met Tyr Lys
    130                 135                 140
Arg Leu Thr
145

<210> SEQ ID NO 111
<211> LENGTH: 147
<212> TYPE: PRT
<213> ORGANISM: Artificial Sequence
<220> FEATURE:
<223> OTHER INFORMATION: GLYAT variant

<400> SEQUENCE: 111

Met Ala Ile Glu Val Lys Pro Ile Asn Ala Glu Asp Thr Tyr Asp Leu
1               5                  10                  15
Arg His Arg Val Leu Arg Pro Lys Gln Pro Ile Glu Val Ile Met Tyr
                20                  25                  30
Glu Thr Asp Leu Leu Arg Gly Ala Phe His Leu Gly Gly Phe Tyr Gly
            35                  40                  45
Gly Lys Leu Ile Ser Val Ala Ser Phe His Gln Ala Glu His Ser Glu
        50                  55                  60
Leu Gln Gly Lys Lys Gln Tyr Gln Leu Arg Gly Val Ala Thr Leu Glu
65                  70                  75                  80
Gly Tyr Arg Asp Gln Lys Ala Gly Ser Ser Leu Val Lys His Ala Glu
                85                  90                  95
Glu Ile Leu Arg Lys Arg Gly Ala Asp Met Leu Trp Cys Asn Ala Arg
            100                 105                 110
Thr Ser Ala Ser Gly Tyr Tyr Glu Lys Leu Gly Phe Ser Glu Gln Gly
        115                 120                 125
Glu Val Phe Glu Thr Pro Pro Ala Gly Pro His Ile Leu Met Tyr Lys
    130                 135                 140
Arg Leu Thr
145

<210> SEQ ID NO 112
<211> LENGTH: 147
<212> TYPE: PRT
<213> ORGANISM: Artificial Sequence
<220> FEATURE:
<223> OTHER INFORMATION: GLYAT variant

<400> SEQUENCE: 112

Met Ala Ile Glu Val Lys Pro Ile Asn Ala Glu Asp Thr Tyr Asp Leu
1               5                  10                  15
Arg His Arg Val Leu Arg Pro Arg Gln Pro Ile Glu Val Ile Met Tyr
                20                  25                  30

```
Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
 50                  55                  60

Leu Gln Gly Lys Lys Gln Tyr Gln Leu Arg Gly Val Ala Thr Leu Glu
 65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
                130                 135                 140

Arg Leu Thr
145

<210> SEQ ID NO 113
<211> LENGTH: 147
<212> TYPE: PRT
<213> ORGANISM: Artificial Sequence
<220> FEATURE:
<223> OTHER INFORMATION: GLYAT variant

<400> SEQUENCE: 113

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Arg Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
 50                  55                  60

Leu Gln Gly Lys Lys Gln Tyr Gln Leu Arg Gly Val Ala Thr Leu Glu
 65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
                130                 135                 140

Arg Leu Thr
145

<210> SEQ ID NO 114
<211> LENGTH: 147
<212> TYPE: PRT
<213> ORGANISM: Artificial Sequence
<220> FEATURE:
<223> OTHER INFORMATION: GLYAT variant

<400> SEQUENCE: 114

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Ser Val Ile Met Tyr
                20                  25                  30
```

Glu Thr Asp Leu Leu Arg Gly Ala Phe His Leu Gly Gly Phe Tyr Gly
           35                  40                  45

Gly Lys Leu Ile Ser Val Ala Ser Phe His Gln Ala Glu His Ser Glu
     50                  55                  60

Leu Gln Gly Lys Lys Gln Tyr Gln Leu Arg Gly Val Ala Thr Leu Glu
 65                  70                  75                  80

Gly Tyr Arg Asp Gln Lys Ala Gly Ser Ser Leu Val Lys His Ala Glu
                 85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145

<210> SEQ ID NO 115
<211> LENGTH: 147
<212> TYPE: PRT
<213> ORGANISM: Artificial Sequence
<220> FEATURE:
<223> OTHER INFORMATION: GLYAT variant

<400> SEQUENCE: 115

Met Ala Ile Glu Val Lys Pro Ile Asn Ala Glu Asp Thr Tyr Asp Leu
 1               5                  10                  15

Arg His Arg Val Leu Arg Pro Asn Gln Pro Ile Ala Val Ile Met Tyr
                 20                  25                  30

Glu Thr Asp Leu Leu Arg Gly Ala Phe His Leu Gly Gly Phe Tyr Gly
           35                  40                  45

Gly Lys Leu Ile Ser Val Ala Ser Phe His Gln Ala Glu His Ser Glu
     50                  55                  60

Leu Gln Gly Lys Lys Gln Tyr Gln Leu Arg Gly Val Ala Thr Leu Glu
 65                  70                  75                  80

Gly Tyr Arg Asp Gln Lys Ala Gly Ser Ser Leu Val Lys His Ala Glu
                 85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145

<210> SEQ ID NO 116
<211> LENGTH: 147
<212> TYPE: PRT
<213> ORGANISM: Artificial Sequence
<220> FEATURE:
<223> OTHER INFORMATION: GLYAT variant

<400> SEQUENCE: 116

Met Ala Ile Glu Val Lys Pro Ile Asn Ala Glu Asp Thr Tyr Asp Leu
 1               5                  10                  15

Arg His Arg Val Leu Arg Pro Asn Gln Pro Ile Glu Arg Ile Met Tyr

```
            20                  25                  30
Glu Thr Asp Leu Leu Arg Gly Ala Phe His Leu Gly Gly Phe Tyr Gly
            35                  40                  45
Gly Lys Leu Ile Ser Val Ala Ser Phe His Gln Ala Glu His Ser Glu
        50                  55                  60
Leu Gln Gly Lys Lys Gln Tyr Gln Leu Arg Gly Val Ala Thr Leu Glu
65                  70                  75                  80
Gly Tyr Arg Asp Gln Lys Ala Gly Ser Ser Leu Val Lys His Ala Glu
                85                  90                  95
Glu Ile Leu Arg Lys Arg Gly Ala Asp Met Leu Trp Cys Asn Ala Arg
            100                 105                 110
Thr Ser Ala Ser Gly Tyr Tyr Glu Lys Leu Gly Phe Ser Glu Gln Gly
            115                 120                 125
Glu Val Phe Glu Thr Pro Pro Ala Gly Pro His Ile Leu Met Tyr Lys
        130                 135                 140
Arg Leu Thr
145

<210> SEQ ID NO 117
<211> LENGTH: 147
<212> TYPE: PRT
<213> ORGANISM: Artificial Sequence
<220> FEATURE:
<223> OTHER INFORMATION: GLYAT variant

<400> SEQUENCE: 117

Met Ala Ile Glu Val Lys Pro Ile Asn Ala Glu Asp Thr Tyr Asp Leu
1               5                   10                  15
Arg His Arg Val Leu Arg Pro Asn Gln Pro Ile Glu Lys Ile Met Tyr
            20                  25                  30
Glu Thr Asp Leu Leu Arg Gly Ala Phe His Leu Gly Gly Phe Tyr Gly
        35                  40                  45
Gly Lys Leu Ile Ser Val Ala Ser Phe His Gln Ala Glu His Ser Glu
    50                  55                  60
Leu Gln Gly Lys Lys Gln Tyr Gln Leu Arg Gly Val Ala Thr Leu Glu
65                  70                  75                  80
Gly Tyr Arg Asp Gln Lys Ala Gly Ser Ser Leu Val Lys His Ala Glu
                85                  90                  95
Glu Ile Leu Arg Lys Arg Gly Ala Asp Met Leu Trp Cys Asn Ala Arg
            100                 105                 110
Thr Ser Ala Ser Gly Tyr Tyr Glu Lys Leu Gly Phe Ser Glu Gln Gly
            115                 120                 125
Glu Val Phe Glu Thr Pro Pro Ala Gly Pro His Ile Leu Met Tyr Lys
        130                 135                 140
Arg Leu Thr
145

<210> SEQ ID NO 118
<211> LENGTH: 147
<212> TYPE: PRT
<213> ORGANISM: Artificial Sequence
<220> FEATURE:
<223> OTHER INFORMATION: GLYAT variant

<400> SEQUENCE: 118

Met Ala Ile Glu Val Lys Pro Ile Asn Ala Glu Asp Thr Tyr Asp Leu
1               5                   10                  15
```

```
Arg His Arg Val Leu Arg Pro Asn Gln Pro Ile Glu Val Ile Met Tyr
            20                  25                  30

Glu Gly Asp Leu Leu Arg Gly Ala Phe His Leu Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145

<210> SEQ ID NO 119
<211> LENGTH: 147
<212> TYPE: PRT
<213> ORGANISM: Artificial Sequence
<220> FEATURE:
<223> OTHER INFORMATION: GLYAT variant

<400> SEQUENCE: 119

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ser Phe His Leu Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145

<210> SEQ ID NO 120
<211> LENGTH: 147
<212> TYPE: PRT
<213> ORGANISM: Artificial Sequence
<220> FEATURE:
<223> OTHER INFORMATION: GLYAT variant

<400> SEQUENCE: 120

Met Ala Ile Glu Val Lys Pro Ile Asn Ala Glu Asp Thr Tyr Asp Leu
1               5                   10                  15
```

Arg His Arg Val Leu Arg Pro Asn Gln Pro Ile Glu Val Ile Met Tyr
            20                  25                  30

Glu Thr Asp Leu Leu Arg Gly Cys Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
    130                 135                 140

Arg Leu Thr
145

<210> SEQ ID NO 121
<211> LENGTH: 147
<212> TYPE: PRT
<213> ORGANISM: Artificial Sequence
<220> FEATURE:
<223> OTHER INFORMATION: GLYAT variant

<400> SEQUENCE: 121

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe Ser Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
    130                 135                 140

Arg Leu Thr
145

<210> SEQ ID NO 122
<211> LENGTH: 147
<212> TYPE: PRT
<213> ORGANISM: Artificial Sequence
<220> FEATURE:
<223> OTHER INFORMATION: GLYAT variant

<400> SEQUENCE: 122

Met Ala Ile Glu Val Lys Pro Ile Asn Ala Glu Asp Thr Tyr Asp Leu

```
        1               5                  10                 15
Arg His Arg Val Leu Arg Pro Asn Gln Pro Ile Glu Val Ile Met Tyr
                20                  25                  30

Glu Thr Asp Leu Leu Arg Gly Ala Phe His His Gly Gly Phe Tyr Gly
                35                  40                  45

Gly Lys Leu Ile Ser Val Ala Ser Phe His Gln Ala Glu His Ser Glu
                50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
                130                 135                 140

Arg Leu Thr
145

<210> SEQ ID NO 123
<211> LENGTH: 147
<212> TYPE: PRT
<213> ORGANISM: Artificial Sequence
<220> FEATURE:
<223> OTHER INFORMATION: GLYAT variant

<400> SEQUENCE: 123

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
                35                  40                  45

Gly Lys Leu Ile Ser Val Ala Ser Phe His Gly Ala Glu His Ser Glu
                50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
                130                 135                 140

Arg Leu Thr
145

<210> SEQ ID NO 124
<211> LENGTH: 147
<212> TYPE: PRT
<213> ORGANISM: Artificial Sequence
<220> FEATURE:
<223> OTHER INFORMATION: GLYAT variant

<400> SEQUENCE: 124
```

```
Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Cys Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
    130                 135                 140

Arg Leu Thr
145

<210> SEQ ID NO 125
<211> LENGTH: 147
<212> TYPE: PRT
<213> ORGANISM: Artificial Sequence
<220> FEATURE:
<223> OTHER INFORMATION: GLYAT variant

<400> SEQUENCE: 125

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Leu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
                115                 120                 125

Glu Val Phe Glu Thr Pro Pro Ala Gly Pro His Ile Leu Met Tyr Lys
    130                 135                 140

Arg Leu Thr
145

<210> SEQ ID NO 126
<211> LENGTH: 147
<212> TYPE: PRT
<213> ORGANISM: Artificial Sequence
<220> FEATURE:
<223> OTHER INFORMATION: GLYAT variant

<400> SEQUENCE: 126
```

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Val His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145

<210> SEQ ID NO 127
<211> LENGTH: 147
<212> TYPE: PRT
<213> ORGANISM: Artificial Sequence
<220> FEATURE:
<223> OTHER INFORMATION: GLYAT variant

<400> SEQUENCE: 127

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Ser
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Pro His Ile Leu Met Tyr Lys
        130                 135                 140

Arg Leu Thr
145

<210> SEQ ID NO 128
<211> LENGTH: 147
<212> TYPE: PRT
<213> ORGANISM: Artificial Sequence
<220> FEATURE:
<223> OTHER INFORMATION: GLYAT variant

<400> SEQUENCE: 128

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Arg
50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 129
<211> LENGTH: 147
<212> TYPE: PRT
<213> ORGANISM: Artificial Sequence
<220> FEATURE:
<223> OTHER INFORMATION: GLYAT variant

<400> SEQUENCE: 129

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
50                  55                  60

Leu Gln Gly Cys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 130
<211> LENGTH: 147
<212> TYPE: PRT
<213> ORGANISM: Artificial Sequence
<220> FEATURE:
<223> OTHER INFORMATION: GLYAT variant

<400> SEQUENCE: 130

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
        50                  55                  60

Leu Gln Gly Lys Val Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 131
<211> LENGTH: 147
<212> TYPE: PRT
<213> ORGANISM: Artificial Sequence
<220> FEATURE:
<223> OTHER INFORMATION: GLYAT variant

<400> SEQUENCE: 131

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
        50                  55                  60

Leu Gln Gly Lys Lys Gln Tyr Gln Leu Arg Gly Val Ala Thr Leu Glu
65                  70                  75                  80

Gly Tyr Arg Asp Gln Arg Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 132
<211> LENGTH: 147
<212> TYPE: PRT
<213> ORGANISM: Artificial Sequence
<220> FEATURE:

<223> OTHER INFORMATION: GLYAT variant

<400> SEQUENCE: 132

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Ala Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 133
<211> LENGTH: 147
<212> TYPE: PRT
<213> ORGANISM: Artificial Sequence
<220> FEATURE:
<223> OTHER INFORMATION: GLYAT variant

<400> SEQUENCE: 133

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Arg Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 134
<211> LENGTH: 147
<212> TYPE: PRT
<213> ORGANISM: Artificial Sequence
<220> FEATURE:
<223> OTHER INFORMATION: GLYAT variant

<400> SEQUENCE: 134

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Thr Leu Val Lys His Ala Glu
            85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 135
<211> LENGTH: 147
<212> TYPE: PRT
<213> ORGANISM: Artificial Sequence
<220> FEATURE:
<223> OTHER INFORMATION: GLYAT variant

<400> SEQUENCE: 135

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Asn Leu Val Lys His Ala Glu
            85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 136
<211> LENGTH: 147
<212> TYPE: PRT

<213> ORGANISM: Artificial Sequence
<220> FEATURE:
<223> OTHER INFORMATION: GLYAT variant

<400> SEQUENCE: 136

```
Met Ala Ile Glu Val Lys Pro Ile Asn Ala Glu Asp Thr Tyr Asp Leu
1               5                   10                  15
Arg His Arg Val Leu Arg Pro Asn Gln Pro Ile Glu Val Ile Met Tyr
            20                  25                  30
Glu Thr Asp Leu Leu Arg Gly Ala Phe His Leu Gly Gly Phe Tyr Gly
        35                  40                  45
Gly Lys Leu Ile Ser Val Ala Ser Phe His Gln Ala Glu His Ser Glu
    50                  55                  60
Leu Gln Gly Lys Lys Gln Tyr Gln Leu Arg Gly Val Ala Thr Leu Glu
65                  70                  75                  80
Gly Tyr Arg Asp Gln Lys Ala Gly Ser Arg Leu Val Lys His Ala Glu
                85                  90                  95
Glu Ile Leu Arg Lys Arg Gly Ala Asp Met Leu Trp Cys Asn Ala Arg
            100                 105                 110
Thr Ser Ala Ser Gly Tyr Tyr Glu Lys Leu Gly Phe Ser Glu Gln Gly
        115                 120                 125
Glu Val Phe Glu Thr Pro Pro Ala Gly Pro His Ile Leu Met Tyr Lys
    130                 135                 140
Arg Leu Thr
145
```

<210> SEQ ID NO 137
<211> LENGTH: 147
<212> TYPE: PRT
<213> ORGANISM: Artificial Sequence
<220> FEATURE:
<223> OTHER INFORMATION: GLYAT variant

<400> SEQUENCE: 137

```
Met Ala Ile Glu Val Lys Pro Ile Asn Ala Glu Asp Thr Tyr Asp Leu
1               5                   10                  15
Arg His Arg Val Leu Arg Pro Asn Gln Pro Ile Glu Val Ile Met Tyr
            20                  25                  30
Glu Thr Asp Leu Leu Arg Gly Ala Phe His Leu Gly Gly Phe Tyr Gly
        35                  40                  45
Gly Lys Leu Ile Ser Val Ala Ser Phe His Gln Ala Glu His Ser Glu
    50                  55                  60
Leu Gln Gly Lys Lys Gln Tyr Gln Leu Arg Gly Val Ala Thr Leu Glu
65                  70                  75                  80
Gly Tyr Arg Asp Gln Lys Ala Gly Ser Gly Leu Val Lys His Ala Glu
                85                  90                  95
Glu Ile Leu Arg Lys Arg Gly Ala Asp Met Leu Trp Cys Asn Ala Arg
            100                 105                 110
Thr Ser Ala Ser Gly Tyr Tyr Glu Lys Leu Gly Phe Ser Glu Gln Gly
        115                 120                 125
Glu Val Phe Glu Thr Pro Pro Ala Gly Pro His Ile Leu Met Tyr Lys
    130                 135                 140
Arg Leu Thr
145
```

<210> SEQ ID NO 138
<211> LENGTH: 147

```
<212> TYPE: PRT
<213> ORGANISM: Artificial Sequence
<220> FEATURE:
<223> OTHER INFORMATION: GLYAT variant

<400> SEQUENCE: 138

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Val Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 139
<211> LENGTH: 147
<212> TYPE: PRT
<213> ORGANISM: Artificial Sequence
<220> FEATURE:
<223> OTHER INFORMATION: GLYAT variant

<400> SEQUENCE: 139

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Met Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 140
```

<211> LENGTH: 147
<212> TYPE: PRT
<213> ORGANISM: Artificial Sequence
<220> FEATURE:
<223> OTHER INFORMATION: GLYAT variant

<400> SEQUENCE: 140

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
        50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Asp Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 141
<211> LENGTH: 147
<212> TYPE: PRT
<213> ORGANISM: Artificial Sequence
<220> FEATURE:
<223> OTHER INFORMATION: GLYAT variant

<400> SEQUENCE: 141

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
        50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Met Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

```
<210> SEQ ID NO 142
<211> LENGTH: 147
<212> TYPE: PRT
<213> ORGANISM: Artificial Sequence
<220> FEATURE:
<223> OTHER INFORMATION: GLYAT variant

<400> SEQUENCE: 142
```

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Val Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

```
<210> SEQ ID NO 143
<211> LENGTH: 147
<212> TYPE: PRT
<213> ORGANISM: Artificial Sequence
<220> FEATURE:
<223> OTHER INFORMATION: GLYAT variant

<400> SEQUENCE: 143
```

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Lys Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 144
<211> LENGTH: 147
<212> TYPE: PRT
<213> ORGANISM: Artificial Sequence
<220> FEATURE:
<223> OTHER INFORMATION: GLYAT variant

<400> SEQUENCE: 144

```
Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
        50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Ala Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145
```

<210> SEQ ID NO 145
<211> LENGTH: 147
<212> TYPE: PRT
<213> ORGANISM: Artificial Sequence
<220> FEATURE:
<223> OTHER INFORMATION: GLYAT variant

<400> SEQUENCE: 145

```
Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
        50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Ala Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145
```

<210> SEQ ID NO 146
<211> LENGTH: 147
<212> TYPE: PRT
<213> ORGANISM: Artificial Sequence
<220> FEATURE:
<223> OTHER INFORMATION: GLYAT variant

<400> SEQUENCE: 146

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Ala Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 147
<211> LENGTH: 147
<212> TYPE: PRT
<213> ORGANISM: Artificial Sequence
<220> FEATURE:
<223> OTHER INFORMATION: GLYAT variant

<400> SEQUENCE: 147

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Ile Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr

<210> SEQ ID NO 148
<211> LENGTH: 147
<212> TYPE: PRT
<213> ORGANISM: Artificial Sequence
<220> FEATURE:
<223> OTHER INFORMATION: GLYAT variant

<400> SEQUENCE: 148

```
Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Cys Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145
```

<210> SEQ ID NO 149
<211> LENGTH: 147
<212> TYPE: PRT
<213> ORGANISM: Artificial Sequence
<220> FEATURE:
<223> OTHER INFORMATION: GLYAT variant

<400> SEQUENCE: 149

```
Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Val Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140
```

Arg Leu Thr
145

<210> SEQ ID NO 150
<211> LENGTH: 147
<212> TYPE: PRT
<213> ORGANISM: Artificial Sequence
<220> FEATURE:
<223> OTHER INFORMATION: GLYAT variant

<400> SEQUENCE: 150

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Thr Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 151
<211> LENGTH: 147
<212> TYPE: PRT
<213> ORGANISM: Artificial Sequence
<220> FEATURE:
<223> OTHER INFORMATION: GLYAT variant

<400> SEQUENCE: 151

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Val Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 152
<211> LENGTH: 147
<212> TYPE: PRT
<213> ORGANISM: Artificial Sequence
<220> FEATURE:
<223> OTHER INFORMATION: GLYAT variant

<400> SEQUENCE: 152

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Leu Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 153
<211> LENGTH: 147
<212> TYPE: PRT
<213> ORGANISM: Artificial Sequence
<220> FEATURE:
<223> OTHER INFORMATION: GLYAT variant

<400> SEQUENCE: 153

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Ala Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys

```
                130                 135                 140
Arg Leu Thr
145

<210> SEQ ID NO 154
<211> LENGTH: 147
<212> TYPE: PRT
<213> ORGANISM: Artificial Sequence
<220> FEATURE:
<223> OTHER INFORMATION: GLYAT variant

<400> SEQUENCE: 154

Met Ala Ile Glu Val Lys Pro Ile Asn Ala Glu Asp Thr Tyr Asp Leu
1               5                  10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Met Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Tyr Lys
    130                 135                 140

Arg Leu Thr
145

<210> SEQ ID NO 155
<211> LENGTH: 147
<212> TYPE: PRT
<213> ORGANISM: Artificial Sequence
<220> FEATURE:
<223> OTHER INFORMATION: GLYAT variant

<400> SEQUENCE: 155

Met Ala Ile Glu Val Lys Pro Ile Asn Ala Glu Asp Thr Tyr Asp Leu
1               5                  10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Ser Gln Gly
        115                 120                 125
```

```
Glu Val Phe Glu Thr Pro Pro Ala Gly Pro His Ile Leu Met Tyr Lys
            130                 135                 140

Arg Leu Thr
145

<210> SEQ ID NO 156
<211> LENGTH: 147
<212> TYPE: PRT
<213> ORGANISM: Artificial Sequence
<220> FEATURE:
<223> OTHER INFORMATION: GLYAT variant

<400> SEQUENCE: 156

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Asp Gln Gly
        115                 120                 125

Glu Val Phe Glu Thr Pro Pro Ala Gly His His Ile Leu Met Tyr Lys
            130                 135                 140

Arg Leu Thr
145

<210> SEQ ID NO 157
<211> LENGTH: 147
<212> TYPE: PRT
<213> ORGANISM: Artificial Sequence
<220> FEATURE:
<223> OTHER INFORMATION: GLYAT variant

<400> SEQUENCE: 157

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125
```

```
Thr Val Phe Glu Thr Pro Pro Ala Gly Pro His Ile Leu Met Tyr Lys
    130                 135                 140

Arg Leu Thr
145

<210> SEQ ID NO 158
<211> LENGTH: 147
<212> TYPE: PRT
<213> ORGANISM: Artificial Sequence
<220> FEATURE:
<223> OTHER INFORMATION: GLYAT variant

<400> SEQUENCE: 158

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Gly Val Phe Glu Thr Pro Pro Ala Gly Pro His Ile Leu Met Tyr Lys
    130                 135                 140

Arg Leu Thr
145

<210> SEQ ID NO 159
<211> LENGTH: 147
<212> TYPE: PRT
<213> ORGANISM: Artificial Sequence
<220> FEATURE:
<223> OTHER INFORMATION: GLYAT variant

<400> SEQUENCE: 159

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
```

```
               115                 120                 125
Ala Val Phe Glu Thr Pro Pro Ala Gly Pro His Ile Leu Met Tyr Lys
       130                 135                 140

Arg Leu Thr
145

<210> SEQ ID NO 160
<211> LENGTH: 147
<212> TYPE: PRT
<213> ORGANISM: Artificial Sequence
<220> FEATURE:
<223> OTHER INFORMATION: GLYAT variant

<400> SEQUENCE: 160

Met Ala Ile Glu Val Lys Pro Ile Asn Ala Glu Asp Thr Tyr Asp Leu
1               5                  10                  15

Arg His Arg Val Leu Arg Pro Asn Gln Pro Ile Glu Val Ile Met Tyr
           20                  25                  30

Glu Thr Asp Leu Leu Arg Gly Ala Phe His Leu Gly Gly Phe Tyr Gly
       35                  40                  45

Gly Lys Leu Ile Ser Val Ala Ser Phe His Gln Ala Glu His Ser Glu
50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Arg Val Phe Glu Thr Pro Pro Ala Gly Pro His Ile Leu Met Tyr Lys
    130                 135                 140

Arg Leu Thr
145

<210> SEQ ID NO 161
<211> LENGTH: 147
<212> TYPE: PRT
<213> ORGANISM: Artificial Sequence
<220> FEATURE:
<223> OTHER INFORMATION: GLYAT variant

<400> SEQUENCE: 161

Met Ala Ile Glu Val Lys Pro Ile Asn Ala Glu Asp Thr Tyr Asp Leu
1               5                  10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110
```

```
Thr Ser Ala Ser Gly Tyr Tyr Glu Lys Leu Gly Phe Ser Glu Gln Gly
        115                 120                 125

Cys Val Phe Glu Thr Pro Pro Ala Gly Pro His Ile Leu Met Tyr Lys
130                 135                 140

Arg Leu Thr
145

<210> SEQ ID NO 162
<211> LENGTH: 147
<212> TYPE: PRT
<213> ORGANISM: Artificial Sequence
<220> FEATURE:
<223> OTHER INFORMATION: GLYAT variant

<400> SEQUENCE: 162

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Trp Glu Thr Pro Pro Ala Gly Pro His Ile Leu Met Tyr Lys
130                 135                 140

Arg Leu Thr
145

<210> SEQ ID NO 163
<211> LENGTH: 147
<212> TYPE: PRT
<213> ORGANISM: Artificial Sequence
<220> FEATURE:
<223> OTHER INFORMATION: GLYAT variant

<400> SEQUENCE: 163

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110
```

Thr Ser Ala Ser Gly Tyr Tyr Glu Lys Leu Gly Phe Ser Glu Gln Gly
        115                 120                 125

Glu Val Phe Gln Thr Pro Pro Ala Gly Pro His Ile Leu Met Tyr Lys
130                 135                 140

Arg Leu Thr
145

<210> SEQ ID NO 164
<211> LENGTH: 147
<212> TYPE: PRT
<213> ORGANISM: Artificial Sequence
<220> FEATURE:
<223> OTHER INFORMATION: GLYAT variant

<400> SEQUENCE: 164

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Arg Thr Pro Pro Ala Gly Pro His Ile Leu Met Tyr Lys
130                 135                 140

Arg Leu Thr
145

<210> SEQ ID NO 165
<211> LENGTH: 147
<212> TYPE: PRT
<213> ORGANISM: Artificial Sequence
<220> FEATURE:
<223> OTHER INFORMATION: GLYAT variant

<400> SEQUENCE: 165

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg

```
            100                 105                 110
Thr Ser Ala Ser Gly Tyr Tyr Glu Lys Leu Gly Phe Ser Glu Gln Gly
        115                 120                 125
Glu Val Phe Glu Ala Pro Pro Ala Gly Pro His Ile Leu Met Tyr Lys
    130                 135                 140
Arg Leu Thr
145

<210> SEQ ID NO 166
<211> LENGTH: 147
<212> TYPE: PRT
<213> ORGANISM: Artificial Sequence
<220> FEATURE:
<223> OTHER INFORMATION: GLYAT variant

<400> SEQUENCE: 166

Met Ala Ile Glu Val Lys Pro Ile Asn Ala Glu Asp Thr Tyr Asp Leu
1               5                   10                  15
Arg His Arg Val Leu Arg Pro Asn Gln Pro Ile Glu Val Ile Met Tyr
            20                  25                  30
Glu Thr Asp Leu Leu Arg Gly Ala Phe His Leu Gly Gly Phe Tyr Gly
        35                  40                  45
Gly Lys Leu Ile Ser Val Ala Ser Phe His Gln Ala Glu His Ser Glu
    50                  55                  60
Leu Gln Gly Lys Lys Gln Tyr Gln Leu Arg Gly Val Ala Thr Leu Glu
65                  70                  75                  80
Gly Tyr Arg Asp Gln Lys Ala Gly Ser Ser Leu Val Lys His Ala Glu
                85                  90                  95
Glu Ile Leu Arg Lys Arg Gly Ala Asp Met Leu Trp Cys Asn Ala Arg
            100                 105                 110
Thr Ser Ala Ser Gly Tyr Tyr Glu Lys Leu Gly Phe Ser Glu Gln Gly
        115                 120                 125
Glu Val Phe Glu Thr Pro Pro Ala Gly Glu His Ile Leu Met Tyr Lys
    130                 135                 140
Arg Leu Thr
145

<210> SEQ ID NO 167
<211> LENGTH: 147
<212> TYPE: PRT
<213> ORGANISM: Artificial Sequence
<220> FEATURE:
<223> OTHER INFORMATION: GLYAT variant

<400> SEQUENCE: 167

Met Ala Ile Glu Val Lys Pro Ile Asn Ala Glu Asp Thr Tyr Asp Leu
1               5                   10                  15
Arg His Arg Val Leu Arg Pro Asn Gln Pro Ile Glu Val Ile Met Tyr
            20                  25                  30
Glu Thr Asp Leu Leu Arg Gly Ala Phe His Leu Gly Gly Phe Tyr Gly
        35                  40                  45
Gly Lys Leu Ile Ser Val Ala Ser Phe His Gln Ala Glu His Ser Glu
    50                  55                  60
Leu Gln Gly Lys Lys Gln Tyr Gln Leu Arg Gly Val Ala Thr Leu Glu
65                  70                  75                  80
Gly Tyr Arg Asp Gln Lys Ala Gly Ser Ser Leu Val Lys His Ala Glu
                85                  90                  95
```

```
Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Ser His Ile Leu Met Tyr Lys
130                 135                 140

Arg Leu Thr
145

<210> SEQ ID NO 168
<211> LENGTH: 147
<212> TYPE: PRT
<213> ORGANISM: Artificial Sequence
<220> FEATURE:
<223> OTHER INFORMATION: GLYAT variant

<400> SEQUENCE: 168

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
                100                 105                 110

Thr Ser Ala Ser Gly Tyr Tyr Glu Lys Leu Gly Phe Ser Glu Gln Gly
            115                 120                 125

Glu Val Phe Glu Thr Pro Pro Ala Gly Ala His Ile Leu Met Tyr Lys
130                 135                 140

Arg Leu Thr
145

<210> SEQ ID NO 169
<211> LENGTH: 147
<212> TYPE: PRT
<213> ORGANISM: Artificial Sequence
<220> FEATURE:
<223> OTHER INFORMATION: GLYAT variant

<400> SEQUENCE: 169

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
                20                  25                  30

Glu Thr Asp Leu Leu Arg Gly Ala Phe His Leu Gly Gly Phe Tyr Gly
            35                  40                  45

Gly Lys Leu Ile Ser Val Ala Ser Phe His Gln Ala Glu His Ser Glu
50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95
```

```
Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Arg His Ile Leu Met Tyr Lys
130                 135                 140

Arg Leu Thr
145

<210> SEQ ID NO 170
<211> LENGTH: 147
<212> TYPE: PRT
<213> ORGANISM: Artificial Sequence
<220> FEATURE:
<223> OTHER INFORMATION: GLYAT variant

<400> SEQUENCE: 170

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Val Met Tyr Lys
130                 135                 140

Arg Leu Thr
145

<210> SEQ ID NO 171
<211> LENGTH: 147
<212> TYPE: PRT
<213> ORGANISM: Artificial Sequence
<220> FEATURE:
<223> OTHER INFORMATION: GLYAT variant

<400> SEQUENCE: 171

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95
```

```
                85                  90                  95
Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Val Lys
    130                 135                 140

Arg Leu Thr
145

<210> SEQ ID NO 172
<211> LENGTH: 147
<212> TYPE: PRT
<213> ORGANISM: Artificial Sequence
<220> FEATURE:
<223> OTHER INFORMATION: GLYAT variant

<400> SEQUENCE: 172

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Val Ile Met Tyr
            20                  25                  30

Glu Thr Asp Leu Leu Arg Gly Ala Phe His Leu Gly Gly Phe Tyr Gly
        35                  40                  45

Gly Lys Leu Ile Ser Val Ala Ser Phe His Gln Ala Glu His Ser Glu
    50                  55                  60

Leu Gln Gly Lys Lys Gln Tyr Gln Leu Arg Gly Val Ala Thr Leu Glu
65                  70                  75                  80

Gly Tyr Arg Asp Gln Lys Ala Gly Ser Ser Leu Val Lys His Ala Glu
                85                  90                  95

Glu Ile Leu Arg Lys Arg Gly Ala Asp Met Leu Trp Cys Asn Ala Arg
            100                 105                 110

Thr Ser Ala Ser Gly Tyr Tyr Glu Lys Leu Gly Phe Ser Glu Gln Gly
        115                 120                 125

Glu Val Phe Glu Thr Pro Pro Ala Gly Pro His Ile Leu Met Cys Lys
    130                 135                 140

Arg Leu Thr
145

<210> SEQ ID NO 173
<211> LENGTH: 146
<212> TYPE: PRT
<213> ORGANISM: Bacillus licheniformis

<400> SEQUENCE: 173

Met Ile Glu Val Lys Pro Ile Asn Ala Glu Asp Thr Tyr Glu Ile Arg
1               5                   10                  15

His Arg Ile Leu Arg Pro Asn Gln Pro Leu Glu Ala Cys Met Tyr Glu
            20                  25                  30

Thr Asp Leu Leu Gly Gly Ala Phe His Leu Gly Gly Tyr Tyr Arg Gly
        35                  40                  45

Lys Leu Ile Ser Ile Ala Ser Phe His Lys Ala Glu His Ser Glu Leu
    50                  55                  60

Glu Gly Glu Glu Gln Tyr Gln Leu Arg Gly Met Ala Thr Leu Glu Gly
65                  70                  75                  80

Tyr Arg Glu Gln Lys Ala Gly Ser Thr Leu Ile Arg His Ala Glu Glu
                85                  90                  95
```

```
Leu Leu Arg Lys Lys Gly Ala Asp Leu Leu Trp Cys Asn Ala Arg Thr
            100                 105                 110

Ser Val Ser Gly Tyr Tyr Glu Lys Leu Gly Phe Ser Glu Gln Gly Glu
        115                 120                 125

Val Tyr Asp Ile Pro Pro Ile Gly Pro His Ile Leu Met Tyr Lys Lys
        130                 135                 140

Leu Thr
145

<210> SEQ ID NO 174
<211> LENGTH: 9
<212> TYPE: PRT
<213> ORGANISM: Artificial Sequence
<220> FEATURE:
<223> OTHER INFORMATION: consensus sequence

<400> SEQUENCE: 174

Val Ile Met Tyr Glu Thr Asp Leu Leu
1               5
```